US007285658B2

(12) United States Patent
Cook et al.

(10) Patent No.: US 7,285,658 B2

(45) Date of Patent: Oct. 23, 2007

(54) NUCLEOTIDE MIMICS AND THEIR PRODRUGS

(75) Inventors: Phillip D. Cook, Fallbrook, CA (US); Guangyi Wang, Carlsbad, CA (US); Thomas W. Bruice, Carlsbad, CA (US); Nicholas A. Boyle, Encinitas, CA (US); Janet M. Leeds, Encinitas, CA (US); Jennifer L. Brooks, Encinitas, CA (US); Marija Prhavc, Encinitas, CA (US); Maria Eugenia Ariza, San Marcos, CA (US); Patrick C. Fagan, Escondido, CA (US); Yi Jin, Carlsbad, CA (US); Vivek K. Rajwanshi, Vista, CA (US); Kathleen D. Tucker, Escondido, CA (US)

(73) Assignee: Biota, Inc., Carlsbad, CA (US)

( * ) Notice: Subject to any disclaimer, the term of this patent is extended or adjusted under 35 U.S.C. 154(b) by 499 days.

(21) Appl. No.: 10/376,654

(22) Filed: Feb. 28, 2003

(65) Prior Publication Data

US 2004/0059104 A1 Mar. 25, 2004

Related U.S. Application Data

(60) Provisional application No. 60/360,699, filed on Feb. 28, 2002, provisional application No. 60/360,915, filed on Feb. 28, 2002.

(51) Int. Cl.

| | |
|---|---|
| ***A61K 31/7072*** | (2006.01) |
| ***A61K 31/7076*** | (2006.01) |
| ***C07H 19/167*** | (2006.01) |
| ***C07H 19/173*** | (2006.01) |
| ***C07H 19/19*** | (2006.01) |
| ***C07H 19/20*** | (2006.01) |

(52) U.S. Cl. ............... 536/26.2; 536/26.22; 536/26.26; 514/49; 514/51

(58) Field of Classification Search .................. 514/49, 514/51, 48

See application file for complete search history.

(56) References Cited

U.S. PATENT DOCUMENTS

| | | | | |
|---|---|---|---|---|
| 3,386,402 | A | 6/1968 | Ross et al. | 260/211.5 |
| 4,266,048 | A | 5/1981 | Horwitz et al. | 536/27 |
| 5,118,672 | A | 6/1992 | Schinazi et al. | 514/47 |
| 5,130,302 | A | 7/1992 | Spielvogel et al. | 514/45 |
| 5,177,198 | A | 1/1993 | Spielvogel et al. | 536/25.33 |
| 5,721,219 | A | 2/1998 | Ingels et al. | 514/47 |
| 5,859,231 | A | 1/1999 | Shaw et al. | 536/25.3 |
| 6,004,939 | A | 12/1999 | Chen et al. | 514/43 |
| 6,143,279 | A | 11/2000 | Boucher et al. | 424/45 |
| 6,303,774 | B1 | 10/2001 | Bottaro et al. | 536/26.23 |
| 7,094,770 | B2 * | 8/2006 | Watanabe et al. | 514/49 |

FOREIGN PATENT DOCUMENTS

| | | |
|---|---|---|
| EP | 0 357 571 | 7/1990 |
| WO | WO 96/00733 | 1/1996 |
| WO | WO 98/20017 | 5/1998 |
| WO | WO 01/79246 | 4/2001 |
| WO | WO 01/45691 | 6/2001 |
| WO | WO 01/87913 | 11/2001 |
| WO | WO 03/008432 | 1/2003 |

OTHER PUBLICATIONS

Victorova et al. "Human DNA polymerases and retroviral reverse transcriptases: selectivity in respect to dNTPs modified at triphosphate residues" Nucleosides and Nucleotides (1999) vol. 18, No. 4 and 5, pp. 1031-1032.*

Hřebabecký et al. "Synthesis of 1-[3-azido-2,3-dideoxy-4-C-(hydroxymethyl)-a-L-threo-pentofuranosyl]thymine, 1-[2,3-dideoxy-4-C-(hydroxymethyl)-a-L-glycero-pentofuranosyl]thymine, and 1-[2,3-dideoxy-4-C-(hydroxymethyl)-a-L-glycero-pent-2-enofuranosyl]thymine"Collection of Czechoslovak Chemical Communications (1993) vol. 58, pp. 409-420.*

Kodama et al., "4'-Ethynyl Nucleoside Analogs: Potent Inhibitors of Multidrug-Resistant Human Immunodeficiency Virus Variants In Vitro" Antimicrobial Agents and Chemotherapy (2001) vol. 45, No. 5, pp. 1539-1546.*

Arabshahi et al., Biochemistry 29:6820-6826 (1990).

Arzumanov et al., J. Biol. Chem. 271:24389-24394 (1996).

Bisacchi et al., Bioorg. Med. Chem. Lett. 7:127 (1997).

Blackburn et al., J. Chem. Soc. Chem. Comm. 1188-1190 (1981).

Bonnaffe et al., J. Org. Chem. 61:895-902 (1996).

Bressi et al., J. Med. Chem. 43:4135-4150 (2000).

Buckheit, Jr. et al., Antimicrobial Agents and Chemotherapy 39:2718-2727 (1995).

Dineva, Nucleosides Nucleotides 15:1459-1467 (1996).

Dyatkina et al., Nucleosides Nucleotides 14:91-103 (1995).

Engel, R., Chem. Rev. 77:349-467 (1977).

Freeman et al., J. Med. Chem. 35:3192-3196 (1992).

Furman et al., Proc. Natl. Acad. Sci. USA 83:8333-8337 (1986).

Girardet et al., J. Med. Chem. 43:3704-3713 (2000).

Gunic et al., Bioorg. Med. Chem. 9:163-170 (2000).

Halbfinger et al., J. Med. Chem. 42:5323-5337 (1999).

Hattori et al., J. Med. Chem. 39:5005-5011 (1996).

He et al., J. Org. Chem. 63:5769-5773 (1998).

He et al., Nucleic Acids Res. 27:1788-1794 (1999).

Hong et al., J. Med. Chem. 29:2038-2044 (1986).

(Continued)

*Primary Examiner*—Shaojia Anna Jiang

*Assistant Examiner*—Eric S Olson

(74) *Attorney, Agent, or Firm*—Morrison & Foerster LLP

(57) ABSTRACT

The present invention relates to nucleoside diphosphate mimics and nucleoside triphosphate mimics, which contain diphosphate or triphosphate moiety mimics and optionally sugar-modifications and/or base-modifications. The nucleotide mimics of the present invention, in a form of a pharmaceutically acceptable salt, a pharmaceutically acceptable prodrug, or a pharmaceutical formulation, are useful as antiviral, antimicrobial, and anticancer agents. The present invention provides a method for the treatment of viral infections, microbial infections, and proliferative disorders. The present invention also relates to pharmaceutical compositions comprising the compounds of the present invention optionally in combination with other pharmaceutically active agents.

10 Claims, No Drawings

OTHER PUBLICATIONS

Hong et al., J. Med. Chem. 33:1380-1386 (1990).
Hong et al., J. Med. Chem. 39:1771-1777 (1996).
Hostetler et al., J. Biol. Chem. 265:6112-6117 (1990).
Huynh-Dinh, Curr. Opin. Invest. Drugs 2:905-915 (1993).
Jeong et al., J. Med. Chem. 36:181 (1993).
Jones et al., Antiviral Res. 27:1-17 (1995).
Kim et al., Tetrahedron Lett. 33:6899 (1992).
Lemieux et al., Can. J. Chem. 47:4413 (1969).
Letsinger et al., J. Am. Chem. Soc. 94:292-293 (1972).
Leydier et al., Nucleosides Nucleotides 13:2035-2050 (1994).
Li et al., Bioorg. Chem. 24:251-261 (1996).
Lin et al., J. Med. Chem. 28:1481-1485 (1985).
Ludwig et al., J. Org. Chem. 56:1777-1783 (1991).
Ma et al., Bioorg. Chem. 17:194-206 (1989).
Ma et al., J. Med. Chem. 35:1938-1941 (1992).
Marquez, *In Advances in Antiviral Drug Design* (DeClercq, E. ed.) JAI Press Inc. 2:89-146 (1996).
Meyer et al., EMBO 19:3520-3529 (2000).
Monasterio, O. and Timasheff, S., Biochemistry 26:6091-99 (1987).
Mosmann, T., J. Immunol. Methods 65:55 (1983).
Norbeck et al., Tetrahedron Lett. 33:6263 (1989).
Parker et al., J. Biol. Chem. 266(3):1754-62 (1991).
Perigaud et al., Adv. In Antiviral Drug Des. 2:147-172 (1995).
Rassu et al., J. Med. Chem. 40:168-180 (1997).
Rose et al., J. Med. Chem. 45(20):4505-4512 (2002).
Scheit et al., J. Carbohydr. Nucleosides Nucleotides 1:485-490 (1974).
Sekiyama et al., J. Med. Chem. 41:1284-1298 (1998).
Shipitsin et al., J. Chem. Soc. Perkin Trans 1 1039-1050 (1999).
Slater, T. et al., Biochim. Biophys. Acta 77:383 (1963).
Stock, J. Org. Chem. 44:3997-4000 (1979).
Trowbridge et al., J. Am. Chem. Soc. 94:3816-3824 (1972).
Ugarkar et al., J. Med. Chem. 43:2894-2905 (2000).
Vandecandelaere et al., Biochemistry 38:8179-88 (1999).
Van der Donk et al., Biochemistry 35:8381-91 (1996).
Vorbruggen et al., Chem. Ber. 114:1234-1255 (1981).
Wagner et al., Med. Res. Rev. 20:417-451 (2000).
Wang et al., Tetrahedron Lett. 38:2393-2396 (1997).
Wilson et al., Synthesis pp. 1465-1479 (1995).
Xu et al., Biochemistry 33:11884-90 (1994).
Yanachkov et al., Nucleosides Nucleotides 13:339-350 (1994).
Yount et al., Biochemistry 10:2484-2489 (1971).
Yount, R.G., Adv. In Enzymol. 43:1-56 (1975).

* cited by examiner

NUCLEOTIDE MIMICS AND THEIR PRODRUGS

This application asserts priority to U.S. provisional application Ser. No. 60/360,699 filed Feb. 28, 2002 and U.S. provisional application Ser. No. 60/360,915 filed Feb. 28, 2002, which are incorporated herein by reference in their entirety.

BACKGROUND OF THE INVENTION

Viral infections are a major threat to human health and account for many serious infectious diseases. Hepatitis C virus (HCV), a major cause of viral hepatitis, infects more than 200 million people worldwide. Current treatment for HCV infection is restricted to immunotherapy with interferon-$\alpha$, alone or in combination with Ribavirin, a nucleoside analog. This treatment is effective in only about half of the patients. Hepatitis B virus (HBV) acutely infects almost a third of the world's human population, and about 5% of the infected are chronic carriers of the virus. Chronic HBV infection causes liver damage that frequently progresses to cirrhosis and liver cancer later in life. Despite the availability and widespread use of effective chemotherapy and vaccines, the number of chronic carriers approaches 400 million worldwide.

Human immunodeficiency virus (HIV) causes progressive degeneration of the immune system, leading to the development of AIDS. A number of drugs have been used clinically, including HIV nucleoside and non-nucleoside reverse transcriptase inhibitors and protease inhibitors. Currently, combination therapies are the accepted standard of treatment of AIDS in order to reduce viral load and the emergence of drug resistance. Despite progress in the development of anti-HIV drugs, AIDS is still one of the leading epidemic diseases. Therefore, there is still an urgent need for new, more effective HCV, HBV, and HIV drugs. The treatment of viral infections caused by other viruses such as HSV, CMV, influenza viruses, West Nile virus, small pox, EBV, VZV, and RSV also needs better medicines.

Bacterial infections long have been the sources of many infectious diseases. The widespread use of antibiotics results in the emergence of drug-resistant life-threatening bacteria. Fungal infections are another type of infectious disease, some of which also can be life-threatening. There is an increasing demand for the treatment of bacterial and fungal infections. Antimicrobial drugs based on new mechanisms of action and new chemical classes are especially important.

Cellular proliferative disorders are responsible for numerous diseases resulting in major morbidity and mortality and have been intensively investigated for decades. Cancer now is the second leading cause of death in the United States, and over 500,000 people die annually from this proliferative disorder. All of the various cells types of the body can be transformed into benign or malignant tumor cells. Transformation of normal cells into cancer cells is a complex process and, thus far, is not fully understood. Treatment of cancer normally consists of surgery, radiation, and chemotherapy. While chemotherapy can be used to treat all types of cancer, surgery and radiation therapy are limited to certain cancers at various stages of growth at certain sites of the body. There are a number of anticancer drugs widely used clinically. Among them are alkylating agents such, as cisplatin, and antimetabolites, such as 5-Fluorouracil, Gemcitabine, Cytarabine, Fludarabine, and Cladarabine. Although surgery, radiation, and chemotherapies are available to treat cancer patients, there is no cure for cancer at the present time. Cancer research is still one of the most important endeavors in medical and pharmaceutical organizations.

Nucleoside analogs have been used clinically for the treatment of viral infections and proliferative disorders for decades. Most of the nucleoside drugs are classified as antimetabolites. After they enter cells, nucleoside analogs are successively phosphorylated to nucleoside 5'-monophosphates, 5'-diphosphates, and 5'-triphosphates. In most cases, nucleoside triphosphates, e.g. 3'-azido-3'-deoxythymidine (AZT, an anti-HIV drug) triphosphate and arabinosylcytosine (Cytarabine, an anticancer drug) triphosphate, are the chemical entities that inhibit DNA or RNA synthesis, either through a competitive inhibition of polymerases or through incorporation of modified nucleotides into DNA or RNA sequences. Nucleosides may act also as their diphosphates. For instance, 2'-deoxy-2',2'-difluorocytidine (Gemcitabine, an anticancer drug) 5'-diphosphate has been shown to inhibit human ribonucleotide reductase. Current clinically-used nucleoside drugs primarily depend on cellular activation by nucleoside kinases (nucleoside to nucleotide) and nucleotide kinases (nucleotides to di- and tri-nucleotides). Efficient phosphorylation at each step is required for a nucleoside to be an effective drug.

In order to overcome the usual deficiencies of cellular phosphorylation of unnatural nucleosides, nucleotides, themselves, have been considered as antimetabolite drugs. However, the multiply-charged nucleotides do not effectively penetrate cell membranes and often are hydrolyzed by certain extracellular enzymes. In the last two decades, nucleoside mono-phosphate prodrugs have been intensively investigated as an alternative drug form (Wagner et al., *Med. Res. Rev.* 2000, 20, 417-451; Jones et al., *Antiviral Res.* 1995, 27, 1-17; Perigaud et al. *Adv. in Antiviral Drug Des.* 1995, 2, 147-172; Huynh-Dinh, *Curr. Opin. Invest. Drugs,* 1993, 2, 905-915). It was hoped that nucleoside mono-phosphate prodrugs, which mask the negative charges on the phosphate by reversible chemical modifications, now being much more lipophilic, would transverse cell membranes and liberate the nucleoside mono-phosphate intracellularly. Cleavage of the prodrug moiety from the nucleoside mono-phosphate would proceed enzymatically via a variety of ubiquitous, non-specific enzymes, like esterases or hydrolytically. Having now bypassed the first kinase step, which is often the most difficult of the three steps with unnatural nucleoside, higher concentration of the required, active species, the nucleoside tri-phosphate was expected. Progress in the area of nucleotide phosphate prodrugs has been made. For instance, certain phosphate prodrugs of anti-HIV nucleosides have been explored for their use as antiviral drugs. The di- and tri-phosphates of 3'-deoxy-3'-azidothymidine (AZT) and 2',3'-didehydro-2',3'-dideoxythymidine (D4T) were converted to their acyl prodrugs (Bonnaffe et al. *J. Org. Chem.* 1996, 61, 895-902). AZT di- and tri-phosphate prodrugs demonstrated similar inhibition of HIV-infected cells as AZT itself, while the corresponding D4T di- and tri-phosphate prodrugs exhibited lower, but still significant anti-HIV activity. Since the acylphosphate moiety of the prodrugs is sensitive to chemical hydrolysis, it is assumed that the prodrugs had been converted to AZT and D4T before they enter cells. Phospholipids also have been as the masking moiety of nucleoside mono- and di-phosphates. AZT di-phosphate tethered with a thioether lipid showed potent inhibition of HIV-infected CEM cells (Hong et al. *J. Med. Chem.* 1996, 39, 1771-1777). Other lipid-tethered nucleoside di- and tri-phosphates also have been studied (Hostetler et al., *J. Biol. Chem.* 1990, 265, 6112-6117). Some antitumor nucleosides were also converted to the corresponding nucleotide prodrugs aimed at enhancing antitumor activities. Treatment with lipid-tethered Ara-C diphosphates demonstrated longer life-span of p388-infected mice than that with Ara-C itself (Hong et al., *J. Med. Chem.* 1986, 29, 2038-2044; 1990, 33, 1380-1386). 8-Aza-2-deoxyadenosine and 8-bromo-2-deoxyadenosine, two weakly cytotoxic agents, were converted to their 5'-bis (pivaloxymethyl)phosphate prodrugs, which exhibited significantly improved cytotoxicity (Rose et al., *J. Med. Chem.* 2002, published on web).

Although the prodrugs of nucleotides bearing natural phosphates exhibited certain in vitro and in vivo activities, several major obstacles remain to be overcome. The most obvious barrier is the inherent instability of the natural phosphates to cellular enzymes. Nucleotide prodrugs may, in certain cases, deliver negatively-charged nucleotides into cells better than the parent nucleotides, but are not significantly stabile towards enzymatic and hydrolytic degradation. In addition, nucleoside phosphates bearing natural phosphates when released from their prodrugs intracellularly, may not be anabolized to the required active species (nucleoside di- or tri-phosphates), but may be catabolized back to the inactive parent nucleoside, which is resistant to phosphoylation. In several cases, not only is the active species not formed in sufficient concentrations to elicit effective therapeutic effects, but instead, an intermediate nucleoside phosphate that is formed may be a toxic species. As a case in point, AZT mono-phosphate accumulates in cells because the nucleoside mono-phosphate is a poor substrate for thymidylate kinase and is thought to be responsible for cellular toxicity.

In order to stabilize nucleotides, several nucleoside phosphates bearing di-phosphate or tri-phosphate mimics have been prepared and some of them have been evaluated various biological assays. Many nucleotide mimics or their biological use have been disclosed (Eckstein et al. U.S. Pat. No. 3,846,402 issued November 1974; Horwitz et al., U.S. Pat. No. 4,266,048 issued May 1981; Schinazi et al., U.S. Pat. No. 5,118,672 issued June 1992; Ingels et al., U.S. Pat. No. 5,721,219 February 1998; Bottaro, et al., U.S. Pat. No. 6,303,774 October 2001; Boucher et al. U.S. Pat. No. 6,143,279 issued November 2000; Johansson, EP0357571, 7/1990; Lebeau et al. WO9600733, 1/1996; Vladimirovich et al., WO9820017, 5/1998; Watanabe, WO0179246, 4/2001; Yerxa et al., WO0145691, 6/2001; Peterson, WO0187913, 11/2001). The early work in the chemistry and biological evaluations of nucleotide mimics have been reviewed (Scheit, K. H., *Nucleotide Analogs*, John Wiley & Sons, New York, (1980); Engel, R., *Chem. Rev.* 1977, 77, 349-467; Yount, R. G., *Adv. in Enzymol.* 1975, 43, 1-56).

One type of nucleoside di- and tri-phosphate mimic has modifications at the bridging positions of nucleoside diphosphates and triphosphates (Yount et al., *Biochemistry* 1971, 10, 2484-2489; Ma et al., *J. Med. Chem.* 1992, 35, 1938-1941; Ma et al., *Bioorg. Chem.* 1989, 17, 194-206; Li et al., *Bioorg. Chem.* 1996, 24, 251-261; Trowbridge et al., *J. Am. Chem. Soc.* 1972, 94, 3816-3824; Stock, *J. Org. Chem.* 1979, 44, 3997-4000; Blackburn et al., *J. Chem. Soc. Chem. Comm.* 1981, 1188-1190; Shipitsin et al., *J. Chem. Soc. Perkin Trans* 1, 1999, 1039-1050; Arabshahi et al, *Biochemistry,* 1990, 29, 6820-6826; Yanachkov et al., *Nucleosides Nucleotides* 1994, 13, 339-350). Among these phosphate mimics are the β,γ-imidotriphosphates, β,γ-methylimidotriphosphates, α,β-imidotriphosphates, α,β:β,γ-diimidotriphosphates, α,β-methylenetriphosphates, β,γ-methylenetriphosphates, α,β:β,γ-bismethylenetriphosphates, α,β-dihalomethylenetriphosphates, α,β-dihalomethylenetriphosphates, β,γ-halomethylenetriphosphates, and α,β-halomethylenetriphosphates. These phosphate mimics usually enhance the stability of the nucleotide towards hydrolysis by cellular enzymes. Methylene and halomethylenes render the nucleoside di- and tri-phosphate mimics considerable more stable to both chemical and enzymatic hydrolysis.

Another type of nucleoside di-phosphate and tri-phosphate mimic is the substitution of one or more phosphate non-bridging oxygen with other heteroatoms or functional group (Ludwig et al., *J. Org. Chem.* 1991, 56, 1777-1783; Dineva, Nucleosides Nucleotides 1996, 15, 1459-1467; Dyatkina et al. *Nucleosides Nucleotides* 1995, 14, 91-103; He et al., *J. Org. Chem.* 1998, 63, 5769-5773; He et al, *Nucleic Acids Res.* 1999, 27, 1788-1794; Meyer et al., *EMBO* 2000, 19, 3520-3529; Arzumanov et al., *J. boil Chem.* 1996, 271, 24389-24394). Among these phosphate mimics are α-O-alkyltriphosphate, α-O-aryltriphosphate, α-P-alkyltriphosphate, γ-P-aryltriphosphate, α-P-alkylaminotriphosphate, α-P-thiotriphosphate, α-P-boranotriphosphate, γ-O-alkyltriphosphate, γ-O-aryltriphosphate, γ-P-alkyltriphosphate, γ-P-aryltriphosphate, γ-P-alkylaminotriphosphate, γ-P-thiotriphosphate. This type of modification on α- or β-phosphorus usually produces diastereomers due to the formation of a chiral phosphorus center. These nucleoside phosphate mimics generally are more stable to cellular nucleases than natural nucleoside phosphates.

Other nucleoside di- and tri-phosphate mimics include modifications at the 5'-position of nucleosides. For instance, 3'-azido'-3',5'-dideoxy-5'-methylenethymidine 5'-C-triphosphate in which the 5'-oxygen is replaced with methylene was synthesized and evaluated for anti-HIV activity (Freeman et al., *J. Med. Chem.* 1992, 35, 3192-3196). The nucleotide mimics in which the 5'-oxygen is replaced by sulfur or amino also were reported (Trowbridge et al., *J. Am. Chem. Soc.* 1972, 94, 3816-3824; Letsinger et al., *J. Am. Chem. Soc.* 1972, 94, 292-293; Scheit et al., *J. Carbohydr. Nucleosides Nucleotides* 1974, 1, 485-490). There are very few nucleotide mimics comprising combinations of two or more phosphate modifications. So far, only nucleotide mimics containing α,β:β,γ-diimidotriphosphate, α,β:β,γ-bismethylenetriphosphate, and α-P-borano-α-P-thiotriphosphate were reported, which contain two modifications each. The parent nucleosides for the preparation of nucleotide mimics in the reported work are generally selected from natural nucleosides and a few well known antiviral nucleosides such as AZT, D4T, and 3'-deoxythymidine.

Some of these nucleotide mimics have been evaluated for their biological activity. AZT 5'-α-P-boranotriphosphate and D4T 5'-α-P-boranotriphosphate exhibited very potent inhibition of HIV reverse transcriptase (RT) with Ki values in the low nM range in assays using homopolymer templates. AZT 5'-β,γ-difluoromethylenetriphosphate and AZT 5'-β,γ-imidotriphosphates also exhibited significant inhibition of DNA polymerase or HIV RT. The negatively-charged nucleotide mimics are not likely to be taken up intact by cells, and no meaningful cell-based antiviral data for di- and tri-nucleotide mimics has ever been published. These nucleotide mimics that are active in cell free biochemical assays contain only one modification each, either at the triphosphate bridging position or simply as a substitution of a phosphate oxygen and, thus, are ready substrates for enzymatic hydrolysis. Therefore, the mimics rapidly are degraded extracellularly to provide the parent nucleoside.

Any biological activity would result from the parent nucleoside being taken into cells and anabolized to an active nucleotide.

Nucleotide di- and tri-phosphate mimics that are resistant to cellular enzymes and demonstrate significant biological activities have not been disclosed. The several known nucleotide mimics are constructed from natural nucleosides, such as adenosine, or from known biologically active nucleosides, such as AZT. Furthermore, it is essential that novel nucleoside di- and tri-phosphate mimics that are resistant to enzymatic degradation possess one or more prodrugs to allow effective intracellular transport. Nucleoside di- and tri-phosphate mimics with attached prodrugs have not been disclosed in the literature.

SUMMARY OF THE INVENTION

There is a need for effective nucleotide drugs, which do not require anabolic enzymatic activation. In one aspect, this invention overcomes the need for anabolic enzymatic activation of nucleosides to active nucleotide species by providing the nucleosides as their di- and tri-phosphates. In this case, the di- and tri-phosphate moieties have been modified one or more times to provide novel nucleotide mimics that are resistant to degrading enzymes.

Thus, in this aspect of the invention novel nucleotide mimics are provided that contain a modified di- or triphosphate mimic that is stable to chemical and enzymatic degradation via hydrolysis, phosphorolysis and other possible reaction types. Furthermore, in another aspect of the invention, the novel nucleoside di- and tri-phosphates are converted into prodrugs to enhance drug absorption and/or drug delivery into cells. Another aspect of the present invention is to provide a combination of the first two aspects and provide prodrugs of novel nucleotide mimics to enhance drug absorption and/or drug delivery into cells.

Another aspect of the present invention is to provide novel nucleotide mimics that are a combination of a novel nucleoside and a di- or tri-phosphate mimic.

An additional aspect of the present invention is to provide novel nucleotide mimics as a composition for therapeutic use for treatment of viral infections, microbial infections, parasite infections and cellular proliferative disorders.

A further aspect of the present invention is to provide a method for treatment of viral infections, microbial infections, parasite infections and proliferative disorders comprising administrating a nucleotide mimic or its prodrug of the present invention.

Such compounds of the invention include prodrugs (i.e., one of $X^7$-$10^x$ must be the prodrug substitutent R*) such as a compound of Formula (I) which may be a D- or L-nucleotide:

(I)

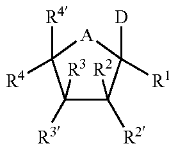

wherein

A is O, S, $CY_2$, NH or NR;

$R^{4'}$ is —L—$R^5$

L is selected from the group consisting of O, S, NH, NR, $CY_2O$, $CY_2S$, $CY_2NH$, $CY_2$, $CY_2CY_2$, $CY_2OCY_2$, $CY_2SCY_2$, and $CY_2NHCY_2$, wherein Y is selected from the group consisting of H, F, Cl, Br, alkyl, alkenyl, and alkynyl, wherein alkyl, alkenyl, and alkynyl may each optionally contain one or more heteroatoms;

$R^5$ is a di- or tri-phosphate moiety of Formula (II):

(II)

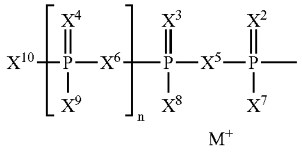

$X^2$, $X^3$, and $X^4$ are selected independently from the group consisting of O, S, Se, NH and NR;

$X^5$ and $X^6$ are selected independently from the group consisting of O, S, Se, $O_2$, $CY_2CO$, CHOH, $C(OH)_2$, $CH_2O$, $CH_2CH_2$, $CH_2CHNH_2$, $CH_2CH_2CHNH_2$, $CY_2OCY_2$, $CY_2$, CRY, $CY_2CY_2$, CHR, CC, HC═CH, NH, NR, NOH, NOR, $NNH_2$, and NNHR;

$X^7$, $X^8$, $X^9$, and $X^{10}$ are selected independently from the group consisting of H, F, OH, SH, $NH_2$, NHOH, NHOR, $NHNH_2$, NHNHR, CN, $N_3$, $^-BH_3M^+$, R, OR, SR, SeH, SeR, NHR, $NR_2$, and R*, wherein R* is a prodrug substitutent;

wherein at least one of $X^7$, $X^8$, $X^9$ and $X^{10}$ is R*;

R* may be conjugated to one or more $X^7$-$X^{10}$ positions

R is selected from the group consisting of alkyl, alkenyl, alkynyl, aryl, acyl, and aralkyl, each optionally containing one or more heteroatoms;

$M^+$ is a cation;

n is 0 or 1;

$R^1$, $R^2$, $R^{2'}$, $R^3$, $R^{3'}$, and $R^4$ are selected independently from the group consisting of H, F, Cl, Br, OH, SH, $NH_2$, NHOH, $N_3$, $NO_2$, CHO, COOH, CN, $CONH_2$, COOR, R, OR, SR, SSR, NHR, and $NR_2$; alternatively, $R^2$ and $R^{2'}$ together and $R^3$ and $R^{3'}$ together independently are ═O, ═S, or ═J—Q, where J is N, CH, CF, CCl, or CBr and Q is H, F, Cl, Br, $N_3$, or R;

D is a nucleoside base of Formula (III) or (IV):

(III)

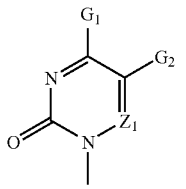

(IV)

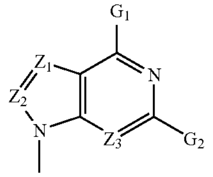

$Z^1$, $Z^2$, and $Z^3$ are independently N, CH or C—$G^3$; and $G^1$, $G^2$, and $G^3$ are selected independently from the group consisting of H, F, Cl, Br, I, OH, SH, $NH_2$, NHOH, $NHNH_2$, $N_3$, NO, $NO_2$, CHO, COOH, CN, $CONH_2$, CONHR, C(S)$NH_2$, C(S)NHR, COOR, R, OR, SR, NHR, and $NR_2$; when two of $G^3$ are present on a molecule they may be same as or different from each other.

Such prodrugs of the invention also include (i.e., one of $X^7$-$X^{10}$ must be the prodrug substitutent R*) also include compound of Formula (XVI):

(XVI)

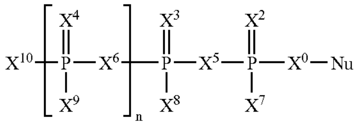

wherein $X^0$, $X^5$ and $X^6$ are selected independently from the group consisting of O, S, NH, and $CY_2$;

wherein Y is selected from the group consisting of H, F, Cl, Br, alkyl, alkenyl, and alkynyl, wherein alkyl, alkenyl, and alkynyl may each optionally contain one or more heteroatoms;

wherein $X^2$, $X^3$, and $X^4$ are selected independently from the group consisting of O, S, and Se;

wherein $X^7$, $X^8$, $X^9$, and $X^{10}$ are selected independently from the group consisting of H, F, OH, SH, $NH_2$, NHOH, CN, $N_3$, $^-BH_3M^+$, R, R*, OR, SR, SeH, SeR, NHR, and $NR_2$;

n is 0 or 1;

wherein at least one of $X^7$, $X^8$, $X^9$ and $X^{10}$ is R*;

wherein Nu is selected from the group consisting of natural nucleosides, sugar-modified nucleosides, base-modified nucleosides, and nucleosides with both sugar and base modifications;

wherein Nu is linked to $X^0$ through $CH_2$ of the sugar moiety of Nu; and

R is selected from the group consisting of alkyl, alkenyl, alkynyl, aryl, acyl, and aralkyl each optionally containing one or more heteroatoms.

In addition, nucleotide mimics of the invention (i.e., $X^7$-$X^{10}$ do not require the presence of a prodrug substitutent R*) include compounds of Formula (I) which may be a D- or L-nucleotide:

(I)

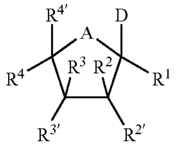

wherein

A is O, S, $CY_2$, NH or NR;

$R^4$ is —L—$R^5$

L is selected from the group consisting of O, S, NH, NR, $CY_2O$, $CY_2S$, $CY_2NH$, $CY_2$, $CY_2CY_2$, $CY_2OCY_2$, $CY_2SCY_2$, and $CY_2NHCY_2$, $CY_2SCY_2$, and wherein Y is selected from the group consisting of H, F, Cl, Br, alkyl, alkenyl, and alkynyl, wherein alkyl, alkenyl, and alkynyl optionally contain one or more heteroatoms;

$R^5$ is a di- or tri-phosphate moiety of Formula (II):

(II)

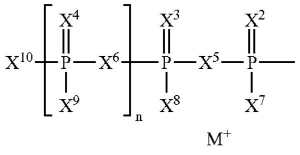

$X^2$, $X^3$, and $X^4$ are selected independently from the group consisting of O, S, Se, NH and NR;

$X^5$ and $X^6$ are selected independently from the group consisting of O, S, Se, $O_2$, $CY_2CO$, CHOH, $C(OH)_2$, $CH_2O$, $CH_2CH_2$, $CH_2CHNH_2$, $CH_2CH_2CHNH_2$, $CY_2OCY_2$, $CY_2$ CRY, $CY_2CY_2$, CHR, CC, HC=CH, NH, NR, NOH, NOR, $NNH_2$, and NNHR;

$X^7$, $X^8$, $X^9$, and $X^{10}$ are selected independently from the group consisting of H, F, OH, SH, $NH_2$, NHOH, NHOR, $NHNH_2$, NHNHR, CN, $N_3$, $^-BH_3M^+$, R, OR, SR, SeH, SeR, NHR, and $NR_2$;

n is 0 or 1;

$R^1$, $R^2$, $R^{2'}$, $R^3$, $R^{3'}$, and $R^4$ are selected independently from the group consisting of H, F, Cl, Br, OH, SH, $NH_2$, NHOH, $N_3$, $NO_2$, CHO, COOH, CN, $CONH_2$, COOR, R, OR, SR, SSR, NHR, and $NR_2$; alternatively, $R^2$ and $R^{2'}$ together and $R^3$ and $R^{3'}$ together independently are =O, =S, or =J—Q, where J is N, CH, CF, CCl, or CBr and Q is H, F, Cl, Br, $N_3$, or R;

D is a nucleoside base of Formula (III) or (IV):

(III)

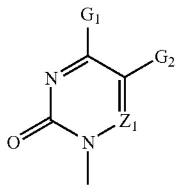

(IV)

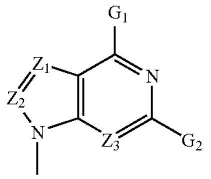

$Z^1$, $Z^2$, and $Z^3$ are independently N, CH or C—$G^3$;

$G^1$, $G^2$, and $G^3$ are selected independently from the group consisting of H, F, Cl, Br, I, OH, SH, $NH_2$, NHOH, $NHNH_2$, $N_3$, NO, $NO_2$, CHO, COOH, CN, $CONH_2$, CONHR, C(S)$NH_2$, C(S)NHR, COOR, R, OR, SR, NHR, and $NR_2$; when two of $G^3$ are present on a molecule they may be same as or different from each other; and R is selected from the group consisting of alkyl, alkenyl, alkynyl, aryl, acyl, and aralkyl each optionally containing one or more heteroatoms;

with provisos that:

(1) when L is $CH_2O$ and is linked to P through O and if one or more of $X^7$-$X^{10}$ is selected from -$BH_3M^+$, SH, F, SR, R, OR, $NH_2$, NHR, and $NR_2$, then $X^2$-$X^6$ and the rest of $X^7$-$X^{10}$ are not all O or OH; or when L is $CH_2O$ and is linked to P through O and if one or more of $X^7$-$X^{10}$ is selected from SH, F, SR, R, OR, $NH_2$, NHR, and $NR_2$, then $X^2$-$X^6$ and the rest of $X^7$-$X^{10}$ are not all O or OH;

(2) when L is $CH_2O$ and is linked to P through O and $X^7$-$X^{10}$ are OH or OR, not all $X^2$-$X^4$ are O;

(3) when L is $CH_2O$ and is linked to P through O and if one or more of $X^2$-$X^4$ is selected from S, NH, NR, NH, then $X^5$-$X^{10}$ are not all O or OH, and one of $X^5$-$X^{10}$ cannot be S when the rest of $X^5$-$X^{10}$ are O or OH; or when L is $CH_2O$ and is linked to P through O and if one of $X^2$-$X^4$ is selected from S, NH, NR, NH, then $X^5$-$X^{10}$ are not all O or OH, and one of $X^5$-$X^{10}$ cannot be S when the rest of $X^5$-$X^{10}$ are O or OH; or when L is $CH_2O$ and is linked to P through O and if two of $X^2$-$X^4$ is selected from S, NH, NR, NH, then $X^5$-$X^{10}$ are not all O or OH, and one of $X^5$-$X^{10}$ cannot be S when the rest of $X^5$-$X^{10}$ are O or OH (4) when L is $CH_2O$ and is linked to P through O and if the following $X^6$-$X^5$ pairs are $CY_2$—O, $CH_2O$—O, $CH_2$—S, CHMe-O, $CHCH_2NH_2$, CO—O, CHOH—O, $C(OH)_2$—O, NH—O, NH—S, NMe-O, NMe-NMe, Naryl-O, NH—NH, $CH_2$—$CH_2$, $CF_2$—$CF_2$, $OCH_2O$—O, O—$CH_2$, O—$CF_2$, O—NH, O—NMe, O—S, S—O, OO—O, O—SS, CC—O, C═C—O, or $O_2$—O then the $X^2$-$X^4$ and $X^7$-$X^{10}$ are not all O or OH, and $X^7$-$X^{10}$ is not one or more F or SEt when $X^2$-$X^4$ and the rest of $X^7$-$X^{10}$ are O or OH;

(5) when L is $CH_2O$ and is linked to P through O and if a $X^2$═P—$X^7$ is selected from O═$P(O)_2BH_3^-$, O═P$(O)_2$NHR, S═$P(O)_2BH_3$, Se═$P(O)_2$OH, S═$P(O)_2$SH, S═$P(O)_2$NHR, and Se═$P(O)_2$SH, at least one of $X^5$ or $X^6$ is not O; or when L is $CH_2O$ and is linked to P through O and if a $X^2$═P—$X^7$ is selected from O═$P(O)_2BH_3^-$, O═$P(O)_2$NHR, S═$P(O)_2BH_3$, Se═P$(O)_2$OH, S═$P(O)_2$SH, S═$P(O)_2$NHR, and Se═$P(O)_2$SH, at least one of $X^3$-$X^6$, $X^8$-$X^{10}$ is not O or OH;

(6) when L is $CH_2O$ or $CH_2S$ and is linked to P through O or S respectively, one or more of $X^2$-$X^{10}$ cannot be S;

(7) when L is $CH_2O$ and is linked to P through O and one or more of $X^7$-$X^{10}$ is SH, then not all $X^2$-$X^4$ is O or OH; or when L is $CH_2O$ and is linked to P through O and one of $X^7$-$X^{10}$ is SH, then $X^2$-$X^6$ and the rest of $X^7$-$X^{10}$ are not all O or OH; or when L is $CH_2O$ and is linked to P through O and two of $X^7$-$X^{10}$ is SH, then $X^2$-$X^6$ and the rest of $X^7$-$X^{10}$ are not all O or OH;

(8) when L is $CH_2O$ and is linked to P through O and if the following $X^6$-$X^5$ pairs are $CH_2$—O, O—$CH_2$, NH—O, or $CH_2$—$CH_2$, then $X^2$-$X^4$ and $X^7$-$X^{10}$ cannot all be O or OH, $X^2$-$X^4$ and $X^7$-$X^{10}$ cannot be one or more S if the remainder of $X^2$-$X^4$ and $X^7$-$X^{10}$ are O or OH, and $X^2$-$X^4$ and $X^7$-$X^{10}$ cannot be one or more Me if the remainder of $X^2$-$X^4$ and $X^7$-$X^{10}$ are O or OH; or when L is $CH_2O$ and is linked to P through O and if the following $X^6$-$X^5$ pairs are $CH_2$—O, O—$CH_2$, NH—O, or $CH_2$—$CH_2$, then at least one of $X^2$-$X^4$ is not O or S; or at least of one of $X^7$-$X^{10}$ is not O, S, or Me; and (9) when L is $CH_2O$ and linked to P through $CH_2$ and if A is O or $CH_2$ and $X^{10}$ is alkyl, aryl, alkoxy, aryloxy, alkylamino, arylamino, or glyceroloxy, $X^6$ is not methylene and substituted methylene.

Further, nucleotide mimics of the invention (i.e., $X^7$-$X^{10}$ do not require the presence of R*), include compound of Formula (XVI):

(XVI)

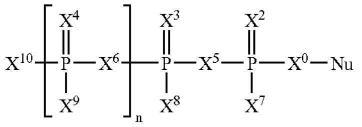

wherein $X^0$, $X^5$ and $X^6$ are selected independently from the group consisting of O, S, NH, $CY_2$;

wherein $X^2$, $X^3$, and $X^4$ are each independently O, S, or Se;

wherein $X^7$, $X^8$, $X^9$, and $X^{10}$ are selected independently from the group consisting of H, F, OH, SH, $NH_2$, NHOH, CN, $N_3$, $^-BH_3M^+$, R, OR, SR, SeH, SeR, NHR, and $NR_2$;

wherein Nu is selected from the group consisting of natural nucleosides, sugar-modified nucleosides, base-modified nucleosides, and nucleosides with both sugar and base modifications;

wherein Nu is linked to $X^0$ through $CH_2$ of the sugar moiety of Nu; and

R is selected from the group consisting of alkyl, alkenyl, alkynyl, aryl, acyl, and aralkyl each optionally containing one or more heteroatoms;

with provisos that:

(1) when L is $CH_2O$ and is linked to P through O and if one or more of $X^7$-$X^{10}$ is selected from -$BH_3M^+$, SH, F, SR, R, OR, $NH_2$, NHR, and $NR_2$, then $X^2$-$X^6$ and the rest of $X^7$-$X^{10}$ are not all O or OH; or when L is $CH_2O$ and is linked to P through O and if one or more of $X^7$-$X^{10}$ is selected from SH, F, SR, R, OR, $NH_2$, NHR, and $NR_2$, then $X^2$-$X^6$ and the rest of $X^7$-$X^{10}$ are not all O or OH;

(2) when L is $CH_2O$ and is linked to P through O and $X^7$-$X^{10}$ are OH or OR, not all $X^2$-$X^4$ are O;

(3) when L is $CH_2O$ and is linked to P through O and if one or more of $X^2$-$X^4$ is selected from S, NH, NR, NH, then $X^5$-$X^{10}$ are not all O or OH, and one of $X^5$-$X^{10}$ cannot be S when the rest of $X^5$-$X^{10}$ are O or OH; or when L is $CH_2O$ and is linked to P through O and if one of $X^2$-$X^4$ is selected from S, NH, NR, NH, then $X^5$-$X^{10}$ are not all O or OH, and one of $X^5$-$X^{10}$ cannot be S when the rest of $X^5$-$X^{10}$ are O or OH; or when L is $CH_2O$ and is linked to P through O and if two of $X^2$-$X^4$ is selected from S, NH, NR, NH, then $X^5$-$X^{10}$ are not all O or OH, and one of $X^5$-$X^{10}$ cannot be S when the rest of $X^5$-$X^{10}$ are O or OH (4) when L is $CH_2O$ and is linked to P through O and if the following $X^6$-$X^5$ pairs are $CY_2$—O, $CH_2O$—O, $CH_2$—S, CHMe-O, $CHCH_2NH_2$, CO—O, CHOH—O, $C(OH)_2$—O, NH—O, NH—S, NMe-O, NMe-NMe, Naryl-O, NH—NH, $CH_2$—$CH_2$, $CF_2$—$CF_2$, $OCH_2O$—O, O—$CH_2$, O—$CF_2$, O—NH, O-NMe, O—S, S—O, OO—O, O—SS, CC—O, C═C—O, or $O_2$—O then the $X^2$-$X^4$ and $X^7$-$X^{10}$ are not all O or OH, and $X^7$-$X^{10}$ is not one or more F or SEt when $X^2$-$X^4$ and the rest of $X^7$-$X^{10}$ are O or OH;

(5) when L is $CH_2O$ and is linked to P through O and if a $X^2$═P—$X^7$ is selected from O═$P(O)_2BH_3^-$, O═P$(O)_2$NHR, S═$P(O)_2BH_3$, Se═$P(O)_2$OH, S═$P(O)_2$SH, S═$P(O)_2$NHR, and Se═$P(O)_2$SH, at least one of $X^5$ or $X^6$ is not O; or when L is $CH_2O$ and is linked to P through O and if a $X^2$═P—$X^7$ is selected from O═$P(O)_2BH_3^-$, O═$P(O)_2$NHR, S═$P(O)_2BH_3$, Se═P$(O)_2$OH, S═$P(O)_2$SH, S═$P(O)_2$NHR, and Se═$P(O)_2$SH, at least one of $X^3$-$X^6$, $X^8$-$X^{10}$ is not O or OH;

(6) when L is $CH_2O$ or $CH_2S$ and is linked to P through O or S respectively, one or more of $X^2$-$X^{10}$ cannot be S;

(7) when L is $CH_2O$ and is linked to P through O and one or more of $X^7$-$X^{10}$ is SH, then not all $X^2$-$X^4$ is O or OH; or when L is $CH_2O$ and is linked to P through O and one of $X^7$-$X^{10}$ is SH, then $X^2$-$X^6$ and the rest of $X^7$-$X^{10}$ are not all O or OH; or when L is $CH_2O$ and is linked to P through O and two of $X^7$-$X^{10}$ is SH, then $X^2$-$X^6$ and the rest of $X^7$-$X^{10}$ are not all O or OH;

(8) when L is $CH_2O$ and is linked to P through O and if the following $X^6$-$X^5$ pairs are $CH_2$—O, O—$CH_2$, NH—O, or $CH_2$—$CH_2$, then $X^2$-$X^4$ and $X^7$-$X^{10}$ cannot all be O or OH, $X^2$-$X^4$ and $X^7$-$X^{10}$ cannot be one or more S if the remainder of $X^2$-$X^4$ and $X^7$-$X^{10}$ are O or OH, and $X^2$-$X^4$ and $X^7$-$X^{10}$ cannot be one or more Me if the remainder of $X^2$-$X^4$ and $X^7$-$X^{10}$ are O or OH; or when L is $CH_2O$ and is linked to P through O and if the following $X^6$-$X^5$ pairs are $CH_2$—O, O—$CH_2$, NH—O, or $CH_2$—$CH_2$, then at least one of $X^2$-$X^4$ is not O or S; or at least of one of $X^7$-$X^{10}$ is not O, S, or Me; and (9) when L is $CH_2O$ and linked to P through $CH_2$ and if A is O or $CH_2$ and $X^{10}$ is alkyl, aryl, alkoxy, aryloxy, alkylamino, arylamino, or glyceroloxy, $X^6$ is not methylene and substituted methylene.

DETAILED DESCRIPTION OF THE INVENTION

Preferred embodiments of the prodrug of Formula (I) described above include prodrugs of the following formulas:

Formula (V):

(V)

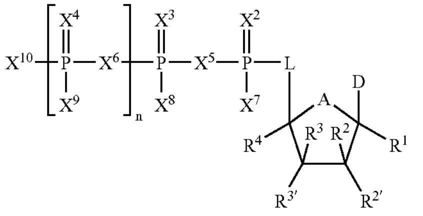

wherein L is selected from the group consisting of O, S, NH, $CY_2$, $CY_2CY_2$, and $CH_2CY_2$ where Y is H, F, Cl, or Br;

wherein $X^2$, $X^3$, and $X^4$ are O, S, Se;

wherein $X^5$ and $X^6$ are selected independently from the group consisting of O, S, NH, NR, $CY_2$; and wherein $X^7$, $X^8$, $X^9$, and $X^{10}$ are selected independently from the group consisting of H, F, OH, SH, $NH_2$, NHOH, $^-BH_3M^+$, R, R*, OR, SR, and NHR.

Formula (VI):

(VI)

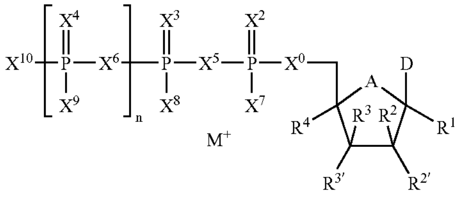

wherein $X^0$ is O, S, or NH;

wherein $X^2$, $X^3$, and $X^4$ are O or S;

wherein $X^5$ and $X^6$ are selected independently from the group consisting of O, S, NH, NR, and $CY_2$;

wherein $X^7$, $X^8$, $X^9$, and $X^{10}$ are selected independently from the group consisting of H, F, OH, SH, $NH_2$, NHOH, $^-BH_3M^+$, R, R*, OR, SR, and NHR.

Formula (VII):

(VII)

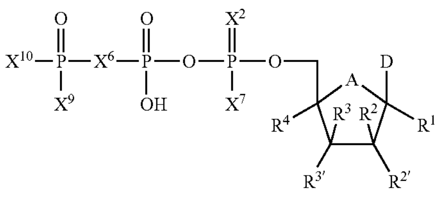

wherein $X^2$ is O or S;

wherein $X^6$ is NH or $CY_2$;

wherein $X^7$ is selected from the group consisting of H, F, SH, $NH_2$, NHOH, $^-BH_3M^+$, R, R*, SR, and NHR; and wherein $X^9$ and $X^{10}$ are selected independently from the group consisting of OH, SH, $NH_2$, NHOH, $^-BH_3M^+$, R, R*, OR, SR, and NHR, preferably $X^2$ is O and $X^7$ is SH, $NH_2$, $^-BH_3M^+$, R, NHR, alkyl, aryl, alkylamino, or arylamino.

Formula (VIII):

(VIII)

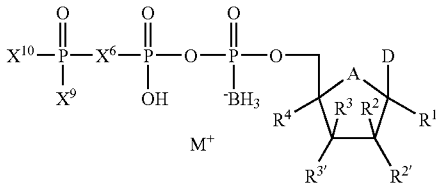

wherein $X^9$ and $X^{10}$ are selected independently from the group consisting of OH, SH, alkyl, alkoxy, aryl, and aryloxy, wherein $X^9$ and $X^{10}$ are selected independently from the group consisting of OH, alkoxy, acylthioethoxy, acyloxymethoxy, 1,2-O-diacylglyceryloxy, and 1-O-alkyl-2-O-acylglyceryloxy; and wherein $X^6$ is selected from a group consisting of NH, CHF, $CCl_2$ and $CF_2$. Most preferably, at least one of $X^9$ or $X^{10}$ is 1, 2,-O-dialkylglyceryloxy.

Formula (IX):

(IX)

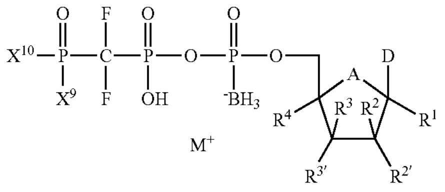

wherein $X^9$ and $X^{10}$ are selected independently from the group consisting of OH, alkoxy, and aryloxy, or wherein $X^9$ and $X^{10}$ are selected independently from the group consisting of OH, alkoxy, acylthioethoxy, acyloxymethoxy, 1,2-O-diacylglyceryloxy, and 1-O-alkyl-2-O-acylglyceryloxy; and wherein $X^6$ is selected from a group consisting of NH, CHF, $CCl_2$ and $CF_2$.

Formula (X):

(X)

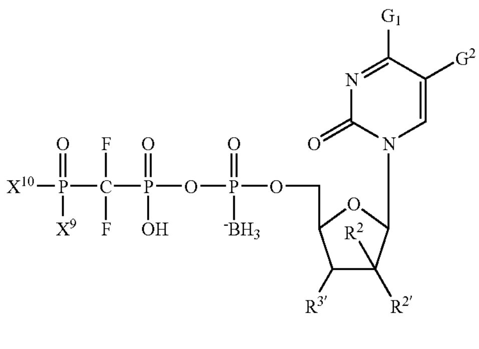

wherein $R^2$ is methyl, ethyl, vinyl, ethynyl, or hydroxymethyl;

wherein $R^{2'}$ is H, F, OH, or OMe, alkyl, methoxyethoxy, or $NH_2$;

wherein $R^{3'}$ is H, F, OH, or $N_3$;

wherein $G^1$ is OH or $NH_2$;

wherein $G^2$ is H or Me;

wherein $X^9$ and $X^{10}$ are selected independently from the group consisting of OH, alkoxy, and aryloxy, or wherein $X^9$ and $X^{10}$ are selected independently from the group consisting of acylthioethoxy, acyloxymethoxy, 1,2-O-diacylglyceryloxy, 1,2-O-dialkylglyceryloxy, and 1-O-alkyl-2-O-acylglyceryloxy.

Formula (XI):

(XI)

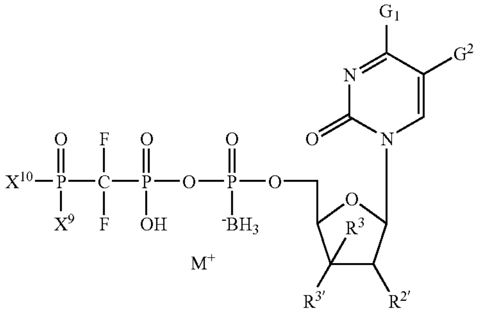

wherein $R^{2'}$ is H, F, OH, or OMe;

wherein $R^3$ is methyl, ethyl, vinyl, ethynyl, or hydroxymethyl;

wherein $R^{3'}$ is H, F, OH, or $N_3$;

wherein $G^1$ is OH or $NH_2$;

wherein $G^2$ is H or Me; and wherein $X^9$ and $X^{10}$ are selected independently from the group consisting of OH, alkoxy, and aryloxy, or wherein $X^9$ and $X^{10}$ are selected independently from the group consisting of acylthioethoxy, acyloxymethoxy, 1,2-O-diacylglyceryloxy, 1,2-O-dialkylglyceryloxy, and 1-O-alkyl-2-O-acylglyceryloxy.

Formula (XII):

(XII)

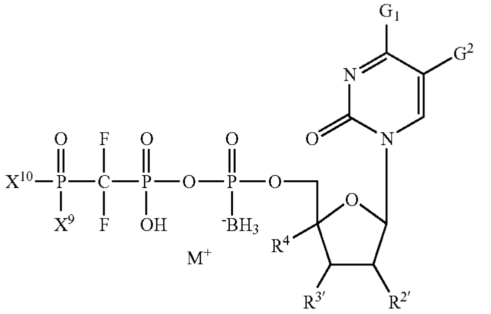

wherein $R^{2'}$ is H, F, OH, or OMe;

wherein $R^{3'}$ is H, F, OH, or $N_3$;

wherein $R^4$ is methyl, ethyl, vinyl, ethynyl, or hydroxymethyl;

wherein $G^1$ is OH or $NH_2$;

wherein $G^2$ is H or Me; and wherein $X^9$ and $X^{10}$ are selected independently from the group consisting of OH, alkoxy, and aryloxy, or wherein $X^9$ and $X^{10}$ are selected independently from the group consisting of acylthioethoxy, acyloxymethoxy, 1,2-O-diacylglyceryloxy, 1,2-O-dialkylglyceryloxy, and 1-O-alkyl-2-O-acylglyceryloxy.

Formula (XIII):

(XIII)

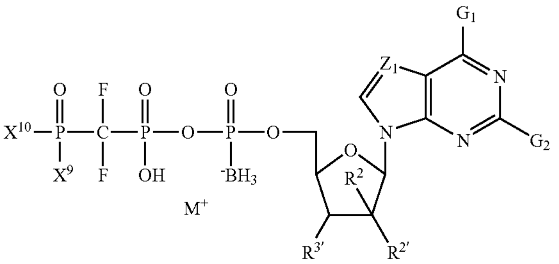

wherein $R^2$ is methyl, ethyl, vinyl, ethynyl, hydroxymethyl or haloalkyl;

wherein $R^{2'}$ is H, F, OH, $OCH_3$, or methoxyethoxy;

wherein $R^{3'}$ is H, F, OH, $N_3$, $NH_2$, or $CH_2OH$;

wherein $G^1$ is OH, $NH_2$, Cl, OMe, NH-cyclopropyl, SH, or S-alkyl;

wherein $G^2$ is H, $NH_2$, NHR, F, Cl, Br, or I;

wherein $Z^1$ is N or CH; and wherein $X^9$ and $X^{10}$ are selected independently from the group consisting of OH, alkoxy and aryloxy, or wherein $X^9$ and $X^{10}$ are selected independently from the group consisting of acylthioethoxy, acyloxymethoxy, 1,2-O-diacylglyceryloxy, 1,2-O-dialkylglyceryloxy, and 1-O-alkyl-2-O-acylglyceryloxy.

Formula (XIV):

(XIV)

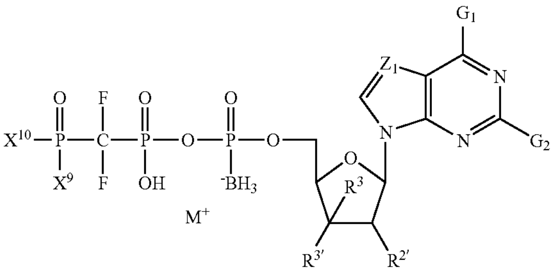

wherein $R^{2'}$ is H, F, OH or $OCH_3$;

wherein $R^3$ is methyl, ethyl, vinyl, ethynyl, or hydroxymethyl;

wherein $R^{3'}$ is H, F, OH, or $N_3$;

wherein $G^1$ is OH or $NH_2$;

wherein $G^2$ is H or $NH_2$;

wherein $Z^1$ is N or CH; and wherein $X^9$ and $X^{10}$ are selected independently from the group consisting of OH, alkoxy and aryloxy, or wherein $X^9$ and $X^{10}$ are selected independently from the group consisting of acylthioethoxy, acyloxymethoxy, 1,2-O-diacylglyceryloxy, 1,2-O-dialkylglyceryloxy, and 1-O-alkyl-2-O-acylglyceryloxy.

Formula (XV):

(XV)

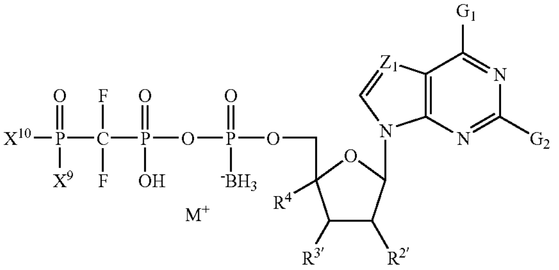

wherein $R^{2'}$ is H, F, OH or $OCH_3$;

wherein $R^{3'}$ is H, F, OH, or $N_3$;

wherein $R^4$ is methyl, ethyl, vinyl, ethynyl, or hydroxymethyl;

wherein $G^1$ is OH or $NH_2$;

wherein $G^2$ is H or $NH_2$;

wherein $Z^1$ is N or CH; and wherein $X^9$ and $X^{10}$ are selected independently from the group consisting of OH, alkoxy and aryloxy, or wherein $X^9$ and $X^{10}$ are selected independently from the group consisting of acylthioethoxy, acyloxymethoxy, 1,2-O-diacylglyceryloxy, 1,2-O-dialkylglyceryloxy, and 1-O-alkyl-2-O-acylglyceryloxy.

Preferred embodiments of the compound of Formula (XVI) include prodrugs of the following formulas:

Formula (XVII):

(XVII)

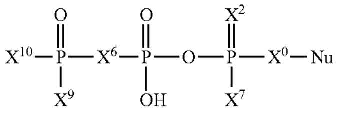

wherein $X^0$ and $X^6$ are selected independently from the group consisting of O, S, NH, $CH_2$, CHCl, CHBr, CHF, $CCl_2$, $CBr_2$, and $CF_2$ wherein $X^2$ is O or S;

wherein $X^7$ is selected from the group consisting of OH, F, SH, $NH_2$, NHOH, $^-BH_3M^+$, R, SR, and NHR; and wherein $X^9$ and $X^{10}$ are selected independently from the group consisting of OH, SH, $NH_2$, NHOH, $^-BH_3M^+$, R, R*, OR, SR and NHR.

Formula (XVII):

(XVII)

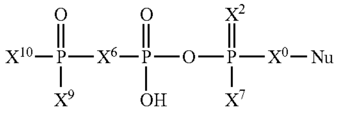

wherein $X^0$ and $X^6$ are selected independently from the group consisting of O, S, NH, $CH_2$, CHCl, CHBr, CHF, $CCl_2$, $CBr_2$, and $CF_2$ wherein $X^2$ is O or S;

wherein $X^7$ is selected from the group consisting of OH, F, SH, $NH_2$, NHOH $^-BH_3M^+$, R, SR, and NHR; and wherein $X^9$ and $X^{10}$ are selected independently from the group consisting of acylthioethoxy, acyloxymethoxy, 1,2-O-diacylglyceryloxy, 1,2-O-dialkylglyceryloxy, and 1-O-alkyl-2-O-acylglyceryloxy.

Formula (XVIII):

(XVIII)

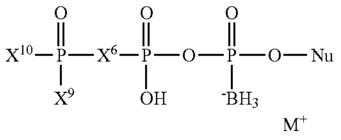

wherein $X^6$ is selected from the group consisting of NH, $CH_2$, CHCl, CHBr, CHF, $CCl_2$, $CBr_2$, and $CF_2$; and wherein $X^9$ and $X^{10}$ are selected independently from the group consisting of OH, SH, alkyl, alkoxy, aryl and aryloxy.

Formula (XVIII):

(XVIII)

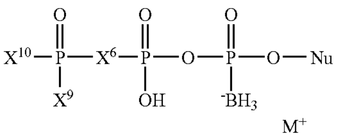

wherein $X^6$ is selected from the group consisting of NH, $CH_2$, CHCl, CHBr, CHF, $CCl_2$, $CBr_2$, and $CF_2$; and wherein $X^9$ and $X^{10}$ are selected independently from the group consisting of acylthioethoxy, acyloxymethoxy, 1,2-O-diacylglyceroxy, 1,2-O-dialkylglyceroxy, and 1-O-alkyl-2-O-acylglyceroxy.

Formula (XIX):

(XIX)

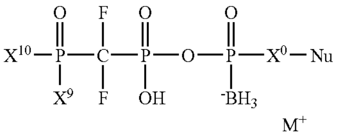

wherein $X^9$ and $X^{10}$ are selected independently from the group consisting of OH, SH, alkyl, alkoxy, aryl and aryloxy, or wherein $X^9$ and $X^{10}$ are selected independently from the group consisting of acylthioethoxy, acyloxymethoxy, 1,2-O-diacylglyceryloxy, 1,2-O-dialkylglyceryloxy, and 1-O-alkyl-2-O-acylglyceryloxy.

In any of formulas (XVI) to (XIX), Nu is preferably selected from:

adenosine,
cytidine,
guanosine,
uridine,
2'-deoxyadenosine,
2'-deoxycytidine,
2'-deoxyguanosine,
thymidine,
inosine,
9-(β-D-arabinofuranosyl)adenine,
1-(β-D-arabinofuranosyl)cytosine,
9-(β-D-arabinofuranosyl)guanine,
1-(β-D-arabinofuranosyl)uracil,
9-(β-D-arabinofuranosyl)hypoxanthine,
1-(β-D-arabinofuranosyl)thymine,
3'-azido-3'-deoxythymidine,
3'-azido-2',3'-dideoxyuridine,
3'-azido-2',3'-dideoxycytidine,
3'-azido-2',3'-dideoxyadenosine,
3'-azido-2',3'-dideoxyguanosine,
3'-azido-2',3'-dideoxyinosine,
3'-deoxythymidine,
2',3'-dideoxyuridine,
2',3'-dideoxyinosine,
2',3'-dideoxyadenosine,
2',3'-dideoxycytidine,
2',3'-dideoxyguanosine,
9-(2,3-dideoxy-1-β-D-ribofuranosyl)-2,6-diaminopurine,
3'-deoxy-2',3'-didehydrothymidine,
2',3'-didehydro-2',3'-dideoxyuridine,
2',3'-didehydro-2',3'-dideoxycytidine,
2',3'-didehydro-2',3'-dideoxyadenosine,
2',3'-didehydro-2',3'-dideoxyguanosine,
2',3'-didehydro-2',3'-dideoxyinosine, 3-deazaadenosine,
3-deazaguanosine,
3-deazainosine,
7-deazaadenosine,
7-deazaguanosine,
7-deazainosine,
6-azauridine,
6-azathymidine,
6-azacytidine,
5-azacytidine,
9-(β-D-ribofuranosyl)-6-thiopurine,
6-methylthio-9-(β-D-ribofuranosyl)purine,
2-amino-9-(β-D-ribofuranosyl)-6-thiopurine,
2-amino-6-methylthio-9-(β-D-ribofuranosyl)purine,
5-fluorocytidine,
5-iodocytidine,
5-bromocytidine,
5-chlorocytidine,
5-fluorouridine,
5-iodouridine,
5-bromouridine,
5-chlorouridine,
2'-C-methyladenosine,
2'-C-methylcytidine,
2'-C-methylguanosine,
2'-C-methylinosine,
2'-C-methyluridine,
2'-C-methylthymidine,
2'-deoxy-2'-fluoroadenosine,
2'-deoxy-2'-fluorocytidine,
2'-deoxy-2'-fluoroguanosine,
2'-deoxy-2'-fluorouridine,
2'-deoxy-2'-fluoroinosine,
2'-α-fluorothymidine,
2'-deoxy-2'-fluoroarabinoadenosine,
2'-deoxy-2'-fluoroarabinocytidine,
2'-deoxy-2'-fluoroarabinoguanosine,
2'-deoxy-2'-fluoroarabinouridine,
2'-deoxy-2'-fluoroarabinoinosine,
2'-β-fluorothymidine,
2'-O-methyladenosine,
2'-O-methylcytidine,
2'-O-methylguanosine,
2'-O-methylinosine,
2'-O-5-dimethyluridine,
2'-C-ethynylcytidine,
2'-C-ethynylguanosine,
2'-C-ethynyluridine,
2'-C-ethynylinosine,
2'-C-ethynyl-5-methyluridine,
3'-C-ethynyladenosine,
3'-C-ethynylcytidine,
3'-C-ethynylguanosine,
3'-C-ethynyluridine,
3'-C-ethynylinosine,
3'-C-ethynyl-5-methyluridine,
3'-deoxyadenosine,
3'-deoxycytidine,
3'-deoxyguanosine,
3'-deoxyuridine,
3'-deoxyinosine,
4'-C-ethynyladenosine,
4'-C-ethynylcytidine,
4'-C-ethynylguanosine,
4'-C-ethynyluridine,
4'-C-ethynylinosine,
4'-C-ethynylthymidine,
4'-C-methyladenosine,
4'-C-methylcytidine,
4'-C-methylguanosine,
4'-C-methyluridine,
4'-C-methylinosine,
4'-C-methylthymidine,
2'-C-methyl-7-deazaadenosine,
2'-C-methyl-7-deazaguanosine,
2'-C-methyl-3-deazaadenosine,
2'-C-methyl-3-deazaguanosine,
2'-O-methyl-7-deazaadenosine,
2'-O-methyl-7-deazaguanosine,
2'-O-methyl-3-deazaadenosine,
2'-O-methyl-3-deazaguanosine,
2'-C-methyl-6-azauridine,
2'-C-methyl-5-fluorouridine,
2'-C-methyl-5-fluorocytidine,
2'-C-methyl-2-chloroadenosine,
2'-deoxy-7-deazaadenosine,
2'-deoxy-3-deazaadenosine,
2'-deoxy-7-deazaguanosine,
2'-deoxy-3-deazaguanosine,
2'-deoxy-6-azauridine,
2'-deoxy-5-fluorouridine,
2'-deoxy-5-fluorocytidine,
2'-deoxy-5-iodouridine,
2'-deoxy-5-iodocytidine,
2'-deoxy-2-chloroadenosine,
2'-deoxy-2-fluoroadenosine,
3'-deoxy-7-deazaadenosine,
3'-deoxy-7-deazaguanosine,
3'-deoxy-3-deazaadenosine,
3'-deoxy-3-deazaguanosine,
3'-deoxy-6-azauridine,
3'-deoxy-5-fluorouridine,
3'-deoxy-5-iodouridine,
3'-deoxy-5-fluorocytidine,
3'-deoxy-2-chloroadenosine,
2',3'-dideoxy-7-deazaadenosine,
2',3'-dideoxy-7-deazaguanosine,
2',3'-dideoxy-3-deazaadenosine,
2',3'-dideoxy-3-deazaguanosine,
2',3'-dideoxy-6-azauridine,
2',3'-dideoxy-5-fluorouridine,
2',3'-dideoxy-5-fluorouridine,
2',3'-dideoxy-5-iodocytidine,
2',3'-dideoxy-2-chloroadenosine,
2',3'-dideoxy-β-L-cytidine,
2',3'-dideoxy-β-L-adenosine,
2',3'-dideoxy-β-L-guanosine,
3'-deoxy-β-L-thymidine,
2',3'-dideoxy-5-fluoro-β-L-cytidine,
β-L-thymidine,
2'-deoxy-β-L-cytidine,
2'-deoxy-β-L-adenosine,
2'-deoxy-β-L-guanosine,
2'-deoxy-β-L-inosine,
β-L-cytidine,
β-L-adenosine,
β-L-guano sine,
β-L-uridine,
β-L-inosine,
2',3'-didehydro-2',3'-dideoxy-β-L-cytidine,
2',3'-didehydro-3'-dideoxy-β-L-thymidine,
2',3'-didehydro-2',3'-dideoxy-β-L-adenosine,
2',3'-didehydro-2',3'-dideoxy-β-L-guanosine,
2',3'-didehydro-2',3'-dideoxy-β-L-5-fluorocytidine, 2'-deoxy-2',2'-difluorocytidine, 9-(β-D-arabinofuranosyl)-2-fluoroadenine, 2'-deoxy-2 '(E)-fluoromethylenecytidine, 2'-deoxy-2' (Z)-fluoromethylenecytidine, (−)-2',3'-dideoxy-3'-thiacytidine, (+)-2',3'-dideoxy-3'-thiacytidine, 1-β-D-ribofuranosyl-1,2,4-triazole-3-carboxamide, 1-β-L-ribofuranosyl-1,2,4-triazole-3-carboxamide, 1-β-D-ribofuranosyl-1,3-imidazolium-5-olate, 1-β-L-ribofuranosyl-1,3-imidazolium-5-olate, 1-β-D-ribofuranosyl-5-ethynylimidazole-4-carboxamide, 1-β-L-ribofuranosyl-5-ethynylimidazole-4-carboxamide, 1-(2-deoxy-2-fluoro-β-D-arabinofuranosyl)-5-iodouracil, 1-(2-deoxy-2-fluoro-β-D-arabinofuranosyl)-5-iodocytosine, 1-(2-deoxy-2-fluoro-β-L-arabinofuranosyl)-5-methyluracil, 1-β-D-arabinofuranosyl-E-5-(2-bromovinyl)uracil, E-5-(2-bromovinyl)-2'-deoxyuridine, 5-trifluoromethylthymidine, 1-β-D-arabinoifuranosyl-5-propynyluracil, 1-(2-deoxy-2-fluoro-1-β-D-arabinofuranosyl)-5-ethyluracil, 2',3'-dideoxy-3'-fluoroguanosine, 3'-deoxy-3'-fluorothymidine, (±)-(1α,2β,3α)-9-[2,3-bis(hydroxymethyl)-1-cyclobutyl] adenine, (±)-(1α,2β,3α)-9-[2,3-bis(hydroxymethyl)-1-cyclobutyl] guanine, (±)-(1β,2α,3β)-9-[2,3-bis(hydroxymethyl)-1-cyclobutyl] guanine, (±)-(1β,2α,3β)-9-[2,3-bis(hydroxymethyl)-1-cyclobutyl]adenine, (1R,3S,4R)-9-(3-hydroxy-4-hydroxymethylcyclopent-1-yl) guanine, (1S,2R,4R)-9-(1-hydroxy-2-hydroxymethylcyclopent-4-yl) guanine, (2R,4R)-9-(2-hydroxymethyl-1,3-dioxolan-4-yl)-2,6-diaminopurine, (2R,4R)-1-(2-hydroxymethyl-1,3-dioxolan-4-yl)cytosine, (2R,4R)-9-(2-hydroxymethyl-1,3-dioxolan-4-yl)guanine, (2R,4R)-1-(2-hydroxymethyl-1,3-dioxolan-4-yl)-5-fluorocytosine, (1R,2S,4S)-9-(4-hydroxy-3-hydroxymethyl-2-methylenecyclopent-4-yl]guanine, and (1S,3R,4S)-9-(3-hydroxy-4-hydroxymethyl-5-methylenecyclopent-1-yl]guanine.

The invention also relates to a pharmaceutical composition comprising a therapeutically effective amount of any of the above compounds, a pharmaceutically acceptable salt thereof, optionally in combination with one or more other active ingredients and/or with a pharmaceutically acceptable carrier. Moreover, the above any of the compounds may be used in a method for the treatment of a microbial infection or proliferative disorder comprising administering a therapeutically effective amount of any of the above compounds to a subject in need thereof.

In another embodiment of the claimed invention preferred nucleotide mimics of the compound of Formula (I) include:

Formula (VI):

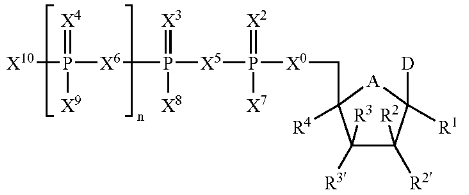

(VI)

wherein $X^0$ is O, S, or NH;

wherein $X^2$, $X^3$, and $X^4$ are O or S;

wherein $X^5$ and $X^6$ are selected independently from the group consisting of O, S, NH, NR, $CY_2$;

wherein $X^7$, $X^8$, $X^9$, and $X^{10}$ are selected independently from the group consisting of H, F, OH, SH, $NH_2$, NHOH, $^-BH_3M^+$, R, OR, SR, and NHR.

Formula (VII):

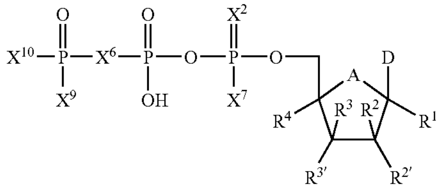

(VII)

wherein $X^2$ is O or S;

wherein $X^6$ is NH or $CY_2$;

wherein $X^7$ is selected from the group consisting of H, F, SH, $NH_2$, NHOH, $^-BH_3M^+$, R, SR, and NHR; and wherein $X^9$ and $X^{10}$ are selected independently from the group consisting of OH, SH, $NH_2$, NHOH, $^-BH_3M^+$, R, OR, SR, and NHR, preferably wherein $X^2$ is O; and preferably wherein $X^7$ is selected from the group consisting of SH, $NH_2$, $^-BH_3M^+$, alkyl, aryl, alkylamino, and arylamino, or wherein $X^7$ is selected from the group consisting of SH, $NH_2$, $^-BH_3M^+$, R, and NHR.

Formula (VIII):

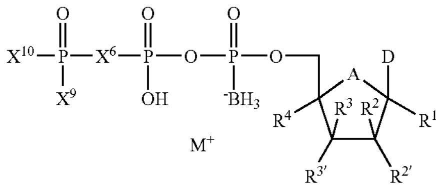

(VIII)

wherein $X^9$ and $X^{10}$ are selected independently from the group consisting of OH, SH, alkyl, alkoxy, aryl, and aryloxy.

Formula (IX):

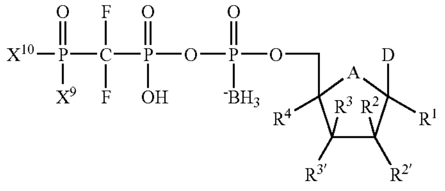

(IX)

wherein $X^9$ and $X^{10}$ are selected independently from the group consisting of OH, alkoxy and aryloxy.

Formula (X):

(X)

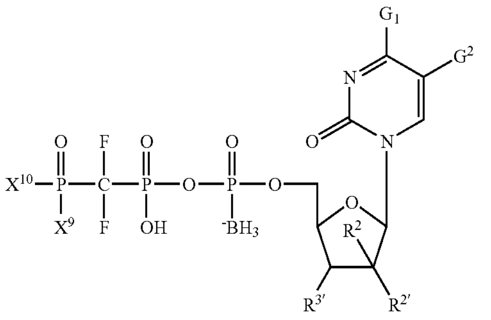

wherein $R^2$ is methyl, ethyl, vinyl, ethynyl, or hydroxymethyl;

wherein $R^{2'}$ is H, F, OH, or OMe, alkyl, methoxyethoxy, or $NH_2$;

wherein $R^{3'}$ is H, F, OH, or $N_3$;

wherein $G^1$ is OH or $NH_2$;

wherein $G^2$ is H or Me; and wherein $X^9$ and $X^{10}$ are selected independently from the group consisting of OH, alkoxy, and aryloxy.

Formula (XI):

(XI)

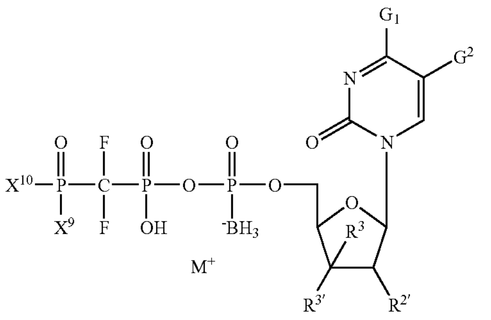

wherein $R^{2'}$ is H, F, OH, or OMe;

wherein $R^3$ is methyl, ethyl, vinyl, ethynyl, or hydroxymethyl;

wherein $R^{3'}$ is H, F, OH, or $N_3$;

wherein $G^1$ is OH or $NH_2$;

wherein $G^2$ is H or Me; and wherein $X^9$ and $X^{10}$ are selected independently from the group consisting of OH, alkoxy, and aryloxy.

Formula (XII):

(XII)

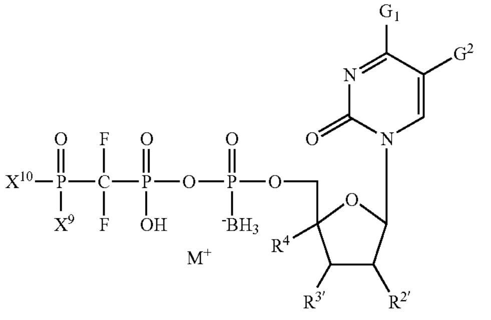

wherein $R^{2'}$ is H, F, OH, or OMe;

wherein $R^{3'}$ is H, F, OH, or $N_3$;

wherein $R^4$ is methyl, ethyl, vinyl, ethynyl, or hydroxymethyl;

wherein $G^1$ is OH or $NH_2$;

wherein $G^2$ is H or Me; and wherein $X^9$ and $X^{10}$ are selected independently from the group consisting of OH, alkoxy, and aryloxy.

Formula (XIII):

(XIII)

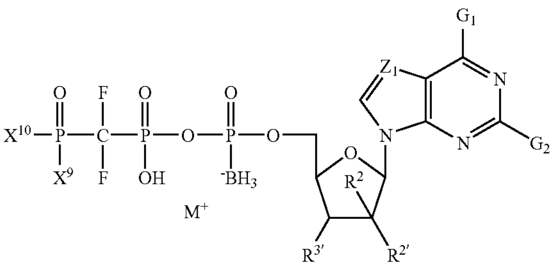

wherein $R^2$ is methyl, ethyl, vinyl, ethynyl, hydroxymethyl, or haloalkyl;

wherein $R^{2'}$ is H, F, OH, $OCH_3$, or methoxyethoxy;

wherein $R^{3'}$ is H, F, OH, $N_3$, $NH_2$, or $CH_2OH$;

wherein $G^1$ is OH, $NH_2$, Cl, OMe, NH-cyclopropyl, SH, or S-alkyl;

wherein $G^2$ is H, $NH_2$, NHR, F, Cl, Br, or I;

wherein $Z^1$ is N or CH; and wherein $X^9$ and $X^{10}$ are selected independently from the group consisting of OH, alkoxy and aryloxy.

Formula (XIV):

(XIV)

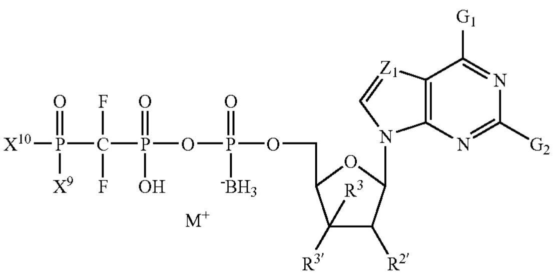

wherein $R^{2'}$ is H, F, OH or $OCH_3$;

wherein $R^3$ is methyl, ethyl, vinyl, ethynyl, or hydroxymethyl;

wherein $R^{3'}$ is H, F, OH, or $N_3$;

wherein $G^1$ is OH or $NH_2$;

wherein $G^2$ is H or $NH_2$;

wherein $Z^1$ is N or CH; and wherein $X^9$ and $X^{10}$ are selected independently from the group consisting of OH, alkoxy and aryloxy.

Formula (XV):

(XV)

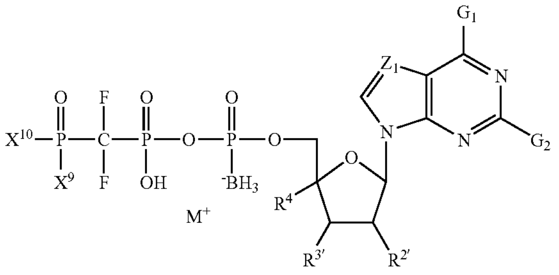

wherein $R^{2'}$ is H, F, OH or $OCH_3$;

wherein $R^{3'}$ is H, F, OH, or $N_3$;

wherein $R^4$ is methyl, ethyl, vinyl, ethynyl, or hydroxymethyl;

wherein $G^1$ is OH or $NH_2$;

wherein $G^2$ is H or $NH_2$;

wherein $Z^1$ is N or CH; and wherein $X^9$ and $X^{10}$ are selected independently from the group consisting of OH, alkoxy and aryloxy.

In another preferred embodiment of the claimed invention, preferred nucleotide mimics of the compound of Formula (XVI) include:

Formula (XVII):

(XVII)

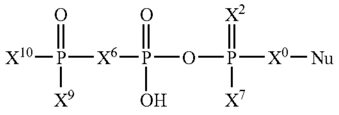

wherein $X^0$ and $X^6$ are selected independently from the group consisting of O, S, NH, $CY_2$;

wherein $X^2$ is O or S;

wherein $X^7$ is selected from the group consisting of OH, F, SH, $NH_2$, NHOH $^-BH_3M^+$, R, SR, and NHR; and wherein $X^9$ and $X^{10}$ are selected independently from the group consisting of OH, SH, $NH_2$, NHOH, $^-BH_3M^+$, R, OR, SR and NHR.

Formula (XVIII):

(XVIII)

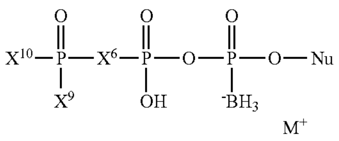

wherein $X^6$ is NH or $CY_2$; and wherein $X^9$ and $X^{10}$ are selected independently from the group consisting of OH, SH, alkyl, alkoxy, aryl and aryloxy.

Formula (XIX):

(XIX)

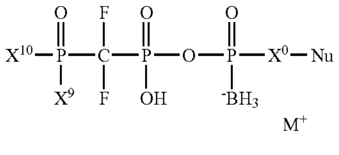

wherein $X^9$ and $X^{10}$ are selected independently from the group consisting of OH, SH, alkyl, alkoxy, aryl and aryloxy.

In any formulas (XVI) to (XIX), Nu is preferably selected from
adenosine,
cytidine,
guanosine,
uridine,
2'-deoxyadenosine,
2'-deoxycytidine,
2'-deoxyguanosine,
thymidine,
inosine,
9-(β-D-arabinofuranosyl)adenine,
1-(β-D-arabinofuranosyl)cytosine,
9-(β-D-arabinofuranosyl)guanine,
1-(β-D-arabinofuranosyl)uracil,
9-(β-D-arabinofuranosyl)hypoxanthine,
1-(β-D-arabinofuranosyl)thymine,
3'-azido-3'-deoxythymidine,
3'-azido-2',3'-dideoxyuridine,
3'-azido-2',3'-dideoxycytidine,
3'-azido-2',3'-dideoxyadenosine,
3'-azido-2',3'-dideoxyguanosine,
3'-azido-2',3'-dideoxyinosine,
3'-deoxythymidine,
2',3'-dideoxyinosine,
2',3'-dideoxyadenosine,
2',3'-dideoxycytidine,
2',3'-dideoxyguanosine,
9-(2,3-dideoxy-1-β-D-ribofuranosyl)-2,6-diaminopurine,
3'-deoxy-2',3'-didehydrothymidine,
2',3'-didehydro-2',3'-dideoxyuridine,
2',3'-didehydro-2',3'-dideoxycytidine,
2',3'-didehydro-2',3'-dideoxyadenosine,
2',3'-didehydro-2',3'-dideoxyguanosine,
2',3'-didehydro-2',3'-dideoxyinosine,
3-deazaadenosine,
3-deazaguanosine,
3-deazainosine,
7-deazaadenosine,
7-deazaguanosine,
7-deazainosine,
6-azauridine,
6-azathymidine,
6-azacytidine,
5-azacytidine,
9-(β-D-ribofuranosyl)-6-thiopurine,
6-methylthio-9-(β-D-ribofuranosyl)purine,
2-amino-9-(β-D-ribofuranosyl)-6-thiopurine,
2-amino-6-methylthio-9-(β-D-ribofuranosyl)purine,
5-fluorocytidine,
5-iodocytidine,
5-bromocytidine,
5-chlorocytidine,
5-fluorouridine,
5-iodouridine,
5-bromouridine,
5-chlorouridine,
2'-C-methyladenosine,
2'-C-methylcytidine,
2'-C-methylguanosine,
2'-C-methylinosine,
2'-C-methyluridine,
2'-C-methylthymidine,
2'-deoxy-2'-fluoroadenosine,
2'-deoxy-2'-fluorocytidine,
2'-deoxy-2'-fluoroguanosine,
2'-deoxy-2'-fluorouridine, 2'-deoxy-2'-fluoroinosine,
2'-α-fluorothymidine,
2'-deoxy-2'-fluoroarabinoadenosine,
2'-deoxy-2'-fluoroarabinocytidine,
2'-deoxy-2'-fluoroarabinoguanosine,
2'-deoxy-2'-fluoroarabinouridine,
2'-deoxy-2'-fluoroarabinoinosine,
2'-P-fluorothymidine,
2'-O-methyladenosine,
2'-O-methylcytidine,
2'-O-methylguanosine,
2'-O-methylinosine,
2'-O-5-dimethyluridine,
2'-C-ethynylcytidine,
2'-C-ethynylguanosine,
2'-C-ethynyluridine,
2'-C-ethynylinosine,
2'-C-ethynyl-5-methyluridine,
3'-C-ethynyladenosine,
3'-C-ethynylcytidine,
3'-C-ethynylguanosine,
3'-C-ethynyluridine,
3'-C-ethynylinosine,
3'-C-ethynyl-5-methyluridine,
3'-deoxyadenosine,
3'-deoxycytidine,
3'-deoxyguanosine,
3'-deoxyuridine,
3'-deoxyinosine,
4'-C-ethynyladenosine,
4'-C-ethynylcytidine,
4'-C-ethynylguanosine,
4'-C-ethynyluridine,
4'-C-ethynylinosine,
4'-C-ethynylthymidine,
4'-C-methyladenosine,
4'-C-methylcytidine,
4'-C-methylguanosine,
4'-C-methyluridine,
4'-C-methylinosine,
4'-C-methylthymidine,
2'-C-methyl-7-deazaadenosine,
2'-C-methyl-7-deazaguanosine,
2'-C-methyl-3-deazaadenosine,
2'-C-methyl-3-deazaguanosine,
2'-O-methyl-7-deazaadenosine,
2'-O-methyl-7-deazaguanosine,
2'-O-methyl-3-deazaadenosine,
2'-O-methyl-3-deazaguanosine,
2'-C-methyl-6-azauridine,
2'-C-methyl-5-fluorouridine,
2'-C-methyl-5-fluorocytidine,
2'-C-methyl-2-chloroadenosine,
2'-deoxy-7-deazaadenosine,
2'-deoxy-3-deazaadenosine,
2'-deoxy-7-deazaguanosine,
2'-deoxy-3-deazaguanosine,
2'-deoxy-6-azauridine,
2'-deoxy-5-fluorouridine,
2'-deoxy-5-fluorocytidine,
2'-deoxy-5-iodouridine,
2'-deoxy-5-iodocytidine,
2'-deoxy-2-chloroadenosine,
2'-deoxy-2-fluoroadenosine,
3'-deoxy-7-deazaadenosine,
3'-deoxy-7-deazaguanosine,
3'-deoxy-3-deazaadenosine,
3'-deoxy-3-deazaguanosine,
3'-deoxy-6-azauridine,
3'-deoxy-5-fluorouridine,
3'-deoxy-5-iodouridine,
3'-deoxy-5-fluorocytidine,
3'-deoxy-2-chloroadenosine,
2',3'-dideoxy-7-deazaadenosine,
2',3'-dideoxy-7-deazaguanosine,
2',3'-dideoxy-3-deazaadenosine,
2',3'-dideoxy-3-deazaguanosine,
2',3'-dideoxy-6-azauridine,
2',3'-dideoxy-5-fluorouridine,
2',3'-dideoxy-5-fluorouridine,
2',3'-dideoxy-5-iodocytidine,
2',3'-dideoxy-2-chloroadenosine,
2',3'-dideoxy-β-L-cytidine,
2',3'-dideoxy-β-L-adenosine,
2',3'-dideoxy-β-L-guanosine,
3'-deoxy-β-L-thymidine,
2',3'-dideoxy-5-fluoro-β-L-cytidine,
β-L-thymidine,
2'-deoxy-β-L-cytidine,
2'-deoxy-β-L-adenosine,
2'-deoxy-β-L-guanosine,
2'-deoxy-β-L-inosine,
β-L-cytidine,
β-L-adenosine,
β-L-guanosine,
β-L-uridine,
β-L-inosine,
2',3'-didehydro-2',3'-dideoxy-β-L-cytidine,
2',3'-didehydro-3'-dideoxy-β-L-thymidine,
2',3'-didehydro-2',3'-dideoxy-β-L-adenosine,
2',3'-didehydro-2',3'-dideoxy-β-L-guanosine,
2',3'-didehydro-2',3'-dideoxy-β-L-5-fluorocytidine,
2'-deoxy-2',2'-difluorocytidine,
9-(β-D-arabinofuranosyl)-2-fluoroadenine,
2'-deoxy-2 '(E)-fluoromethylenecytidine,
2'-deoxy-2'(Z)-fluoromethylenecytidine,
(−)-2',3'-dideoxy-3'-thiacytidine,
(+)-2',3'-dideoxy-3'-thiacytidine,
1-β-D-ribofuranosyl-1,2,4-triazole-3-carboxamide,
1-β-L-ribofuranosyl-1,2,4-triazole-3-carboxamide,
1-β-D-ribofuranosyl-1,3-imidazolium-5-olate,
1-β-L-ribofuranosyl-1,3-imidazolium-5-olate,
1-β-D-ribofuranosyl-5-ethynylimidazole-4-carboxamide,
1-β-L-ribofuranosyl-5-ethynylimidazole-4-carboxamide,
1-(2-deoxy-2-fluoro-β-D-arabinofuranosyl)-5-iodouracil,
1-(2-deoxy-2-fluoro-β-D-arabinofuranosyl)-5-iodocytosine,
1-(2-deoxy-2-fluoro-β-L-arabinofuranosyl)-5-methyluracil,
1-β-D-arabinofuranosyl-E-5-(2-bromovinyl)uracil,
E-5-(2-bromovinyl)-2'-deoxyuridine,
5-trifluoromethylthymidine,
1-β-D-arabinofuranosyl-5-propynyluracil,
1-(2-deoxy-2-fluoro-1-β-D-arabinofuranosyl)-5-ethyluracil,
2',3'-dideoxy-3'-fluoroguanosine,
3'-deoxy-3'-fluorothymidine,
(±)-(1α,2β,3α)-9-[2,3-bis(hydroxymethyl)-1-cyclobutyl] adenine,
(±)-(1α,2β,3α)-9-[2,3-bis(hydroxymethyl)-1-cyclobutyl] guanine,
(±)-(1β,2α,3β)-9-[2,3-bis(hydroxymethyl)-1-cyclobutyl] guanine,
(±)-(1β,2α,3β)-9-[2,3-bis(hydroxymethyl)-1-cyclobutyl]adenine,
(1R,3S,4R)-9-(3-hydroxy-4-hydroxymethylcyclopent-1-yl) guanine, (1S,2R,4R)-9-(1-hydroxy-2-hydroxymethylcyclopent-4-yl) guanine,
(2R,4R)-9-(2-hydroxymethyl-1,3-dioxolan-4-yl)-2,6-diaminopurine,
(2R,4R)-1-(2-hydroxymethyl-1,3-dioxolan-4-yl)cytosine,
(2R,4R)-9-(2-hydroxymethyl-1,3-dioxolan-4-yl)guanine,
(2R,4R)-1-(2-hydroxymethyl-1,3-dioxolan-4-yl)-5-fluorocytosine,
(1R,2S,4S)-9-(4-hydroxy-3-hydroxymethyl-2-methylenecyclopent-4-yl]guanine, and
(1S,3R,4S)-9-(3-hydroxy-4-hydroxymethyl-5-methylenecyclopent-1-yl]guanine.

The invention also includes a pharmaceutical composition comprising a therapeutically effective amount of any of the above nucleotide mimic compounds, a pharmaceutically acceptable salt thereof, or a pharmaceutically acceptable prodrug thereof, optionally in combination with one or more other active ingredients and/or with a pharmaceutically acceptable carrier. Moreover any of the above mimics may be used in a method for the treatment of microbial infects or a proliferative disorder comprising administering a therapeutically effective amount of any of the above nucleotide mimic compounds to a subject in need thereof.

The definitions of certain terms and further descriptions of the above embodiments are given below.

A. Definitions

The term moiety, unless otherwise specified, refers to a portion of a molecule. Moiety may be, but is not limited to, a functional group, an acyclic chain, a phosphate mimic, an aromatic ring, a carbohydrate, a carbocyclic ring, a heterocycle or a prodrug A "natural" nucleoside is one that occurs in nature. For the purposes of this invention the following nucleosides are defined as the natural nucleosides: adenosine, cytidine, guanosine, uridine, 2'-deoxyadenosine, 2'-deoxycytidine, 2'-deoxyguanosine, thymidine, and inosine.

The term base, unless otherwise specified, refers to the base moiety of a nucleoside or nucleotide (a nucleobases). The base moiety is the heterocycle portion of a nucleoside or nucleotide. The base moiety of a nucleotide mimic of Formula (I) or (XVI) may be a pyrimidine derivative or analog, a purine derivative or analog, or other heterocycle. The nucleoside base may contain two or more nitrogen atoms and may contain one or more peripheral substituents. The nucleoside base is attached to the sugar moiety of the nucleotide mimic in such ways that both β-D- and β-L-nucleoside and nucleotide can be produced.

The term sugar refers to the ribofuranose of deoxyribofuranose portion of a nucleoside or nucleotide. The sugar moiety of nucleotide mimics of Formula (I) may contain one or more substitutents at the C1-, C2-, C3-, C4, and C-5-position of the ribofuranose. Substituents may direct to either the α- or β-face of the ribofuranose. The nucleoside base that can be considered as a substitutent at the C-1 position of the ribofuranose directs to the β-face of the sugar. The β-face is the side of a ribofuranose on which a purine or pyrimidine base of natural β-D-nucleosides is present. The α-face is the side of the sugar opposite to the β-face. The sugar moiety of nucleotide mimics (XVI) of the present invention is not limited to a ribofuranose and its derivatives, instead, it may be a carbohydrate, a carbohydrate analog, a carbocyclic ring, or other ribofuranose analog.

The term sugar-modified nucleoside refers to a nucleoside containing a modified sugar moiety.

The term base-modified nucleoside refers to a nucleoside containing a modified base moiety, relative to a base moiety found in a natural nucleoside.

The term phosphate mimic, unless otherwise specified, refers to a phosphate analog, which may be a phosphonate, phosphothioate, phosphoselenate, selenophosphate, thiophosphate, P-boranophosphate, or phosphoramidate, or a combination thereof. The term diphosphate mimic and triphosphate mimic specifically refer to a diphosphate analog and a triphosphate analog, respectively, which comprises at least one of the phosphate mimics, one of the modifications at the bridging site of diphosphate and triphosphate, or replacements of non-bridging phosphate oxygens. The modification at the bridging site, i.e., in the $X^5$ and $X^6$ positions of Formulas (II) and (XVI), includes the replacement of O by other atoms or functions such as S, Se, $O_2$, NH, NHR, NR, $CH_2$, CHF, CHCl, CHBr, $CF_2$, $CCl_2$, $CBr_2$, CHR, $CYCO_2$, $CH_2O$, CHOH, $C(OH)_2$, $CH_2CH_2$, CC, CH=CH, $CH_2CH_2CHNH_2$, $CH_2CHNH_2$, $CY_2OCY_2$, $CY_2$, $CY_2CY_2$, and $CR_2$ where R is selected from the group consisting of alkyl, alkenyl, alkynyl, aryl, acyl, and aralkyl each optionally containing one or more heteroatoms. Non-bridging phosphate oxygens, e.g., in $X^7$-$X^{10}$ positions of Formula (II) can be replaced by a variety of substitutents including H, F, OH, SH, $NH_2$, NHOH, NHOR, $NHNH_2$, NHNHR, CN, $N_3$, $^-BH_3M^+$, R, OR, SR, SeH, SeR, NHR, $NR_2$, and R* where R is as defined above, and wherein R* is a prodrug substitutent. $M^+$ is a cation preferably a pharmaceutically acceptable cation such as $Ca^{2+}$, ammonium, trialkylammonium or tertaalkylammonium, e.g., $NH_4^+$, $Et_3NH^+$, $Bu_3NH^+$, and $Bu_4N^+$.

The α-P, β-P, and γ-P in the diphosphate mimics and triphosphate mimics may independently adopt either R or S configurations when they become a chiral phosphorus.

The term nucleotide mimic, as used herein and unless otherwise specified, refers to a nucleoside di-phosphate mimic and/or a nucleoside tri-phosphate mimic. They may be termed as NDP mimic and NTP mimic, respectively.

The term alkyl, unless otherwise specified, refers to a saturated straight, branched, or cyclic hydrocarbon of $C_1$ to $C_{18}$. Alkyls may include, but are not limited to, methyl, ethyl, n-propyl, isopropyl, cyclopropyl, n-butyl, isobutyl, t-butyl, cyclobutyl, n-pentyl, isopentyl, neopentyl, cyclopentyl, n-hexyl, cyclohexyl, dodecyl, tetradecyl, hexadecyl, and octadecyl.

The term alkenyl, unless otherwise specified, refers to an unsaturated hydrocarbon of $C_2$ to $C_{18}$ that contains at least one carbon-carbon double bond and may be straight, branched or cyclic. Alkenyls may include, but are not limited to, olefinic, propenyl, allyl, 1-butenyl, 3-butenyl, 1-pentenyl, 4-pentenyl, 1-hexenyl, and cyclohexenyl.

The term alkynyl, unless otherwise specified, refers to an unsaturated hydrocarbon of $C_2$ to $C_{18}$ that contains at least one carbon-carbon triple bond and may be straight, branched or cyclic. Alkynyls may include, but are not limited to, ethynyl, 1-propynyl, 2-propynyl, 1-butynyl, and 3-butynyl.

The term aryl, unless otherwise specified, refers to an aromatic or heteroaromatic hydrocarbon moiety. Aryls may include, but are not limited to, phenyl, biphenyl, naphthyl, pyridinyl, pyrrolyl, and imidazolyl, optionally containing one or more substitutents. The substitutents may include, but are not limited to, hydroxy, amino, thio, halogen, cyano, nitro, alkoxy; alkylamino, alkylthio, hydroxycarbonyl, alkoxycarbonyl, and carbamoyl.

The term aralkyl, unless otherwise specified, refers to a moiety that contains both an aryl and an alkyl, an alkenyl, or an alkynyl. Aralkyls can be attached through either the aromatic portion or the non-aromatic position. Aralkyls may include, but are not limited to, benzyl, phenethyl, phenylpropyl, methylphenyl, ethylphenyl, propylphenyl, butylphenyl, phenylethenyl, phenylpropenyl, phenylethynyl, and phenylpropynyl.

The term acyl, unless otherwise specified, refers to alkylcarbonyl. Acyls may include, but are not limited to, formyl, acetyl, fluoroacetyl, difluoroacetyl, trifluoroacetyl, chloroacetyl, dichloroacetyl, trichloroacetyl, propionyl, benzoyl, toluoyl, butyryl, isobutyryl, pivaloyl, acylthioethoxy, acyloxymethoxy, 1,2-O-diacylglyceryloxy, 1,2-O-dialkylglyceryloxy, and 1-O-alkyl-2-O-acylglyceryloxy.

The term heteroatom refers to oxygen, sulfur, nitrogen, selenium, borane, or halogen. When one or more heteroatoms are attached to alkyl, alkeneyl, alkynyl, acyl, aryl, or arakyl, a new functional group may be produced. For instance, when one or more heteroatoms are attached to an alkyl, substituted alkyls may be produced, including, but not limited to, fluoroalkyl, chloroalkyl, bromoalkyl, iodoalkyl, alkoxy, hydroxyalkyl, alkylamino, aminoalkyl, alkylthio, thioalkyl, azidoalkyl, cyanoalkyl, nitroalkyl, carbamoylalkyl, carboxylalkyl, acylalkyl, acylthioethoxy, acyloxymethoxy, 1,2-O-diacylglyceryloxy, 1,2-O-dialkylglyceryloxy, and 1-O-alkyl-2-O-acylglyceryloxy.

The term halogen or halo refers to fluorine, chlorine, bromine, or iodine.

The term function refers to a substituent. Functions may include, but are not limited to, hydroxy, amino, sulfhydryl, azido, cyano, halo, nitro, hydroxycarbonyl, alkoxycarbonyl, or carboxyl, either protected or unprotected.

$R^{4'}$ of Formula (I) represents a combination (—L—$R^5$) of a linker moiety (L) and a phosphate moiety ($R^5$). L is usually either a one-atom or a two-atom linker, which may, through either side, attach to the sugar and phosphate mimic moiety. $R^5$ represents a diphosphate mimic or a triphosphate mimic.

R of Formula (I) and (XVI) is a univalent substitutent and present on the base, sugar and phosphate mimic moieties. R is selected from the group consisting of alkyl, alkenyl, alkynyl, aryl, acyl, and aralkyl, each optionally containing one or more heteroatoms, which are as defined above.

R* is a prodrug substitutent. The term prodrug, unless otherwise specified, refers to a masked (protected) form of a nucleotide mimic of Formula (I) or (XVI) when one or more of $X^7$-$X^{10}$ is R*. The prodrug of the nucleotide mimic can mask the negative charges of the di-phosphate ($X^7$, $X^8$, $X^{10}$) mimic or tri-phosphate ($X^7$-$X^{10}$) mimic moiety or phosphate moiety, entirely or partially, or mask a heteroatom substituted alkyl, aryl or aryalkyl (W, see below) attached to a phosphate or phosphate mimic moiety in order to enhance drug absorption and/or drug delivery into cells. The prodrug can be liberated either by cellular enzymes such as lipases, esterases, reductases, oxidases, nucleases or by chemical cleavage such as hydrolysis to release (liberate) the nucleotide mimic, preferably intracellularly. Prodrugs are often referred to as cleavable prodrugs. Prodrug substitutents include, but are not limited to: proteins, antibiotics (and antibiotic fragments), D- and L-amino acids attached to a phosphate moiety or a phosphate mimic moiety via a carbon atom (phosphonates), a nitrogen atom (phosphoamidates), or an oxygen atom (phosphoesters), peptides (up to 10 amino acids) attached to a phosphate moiety or a phosphate mimic moiety via a carbon atom (phosphonates), a nitrogen atom (phosphoamidates), or an oxygen atom (phosphoesters), drug moieties attached to a phosphate moiety or a phosphate mimic moiety via a carbon atom (phosphonates), a nitrogen atom (phosphoamidates), or an oxygen atom (phosphoesters), cholesterols, folic acids, vitamins, polyamines, carbohydrates, polyethylene glycols (PEGs), cyclosaligenyls, substituted 4 to 8-membered rings, with or without heteroatom substitutions, with 1,3-phosphodiester, 1,3-phosphoamidate/phosphoester or 1,3-phosphoamidate attachments to a terminal phosphate or phosphate mimic moiety (γ or β) or connecting between an α,β or β,γ phosphate moiety or phosphate mimic moiety, acylthioethoxy, (SATE) $RCOSCH_2CH_2O$—, $RCOSCH_2CH_2O$—W—O—, $RCOSCH_2CH_2O$—W—S—, $RCOSCH_2CH_2O$—W—NH—, $RCOSCH_2CH_2O$—W—, $RCOSCH_2CH_2O$—W—$CY_2$—, acyloxymethoxy, $RCOOCH_2O$—, $RCOOCH_2O$—W—O—, $RCOOCH_2O$—W—S—, $RCOOCH_2O$—W—NH—, $RCOOCH_2O$—W—, $RCOOCH_2O$—W—$CY_2$—, alkoxycarbonyloxymethoxy, $ROCOOCH_2O$—, $ROCOOCH_2O$—W—O—, $ROCOOCH_2O$—W—S—, $ROCOOCH_2O$—W—NH—, $ROCOOCH_2O$—W—, $ROCOOCH_2O$—W—$CY_2$—, acylthioethyldithioethoxy (DTE) $RCOSCH_2CH_2SSCH_2CH_2O$—, $RCOSCH_2CH_2SSCH_2CH_2O$—W—, $RCOSCH_2CH_2SSCH_2CH_2O$—W—O—, $RCOSCH_2CH_2SSCH_2CH_2O$—W—S—, $RCOSCH_2CH_2SSCH_2CH_2O$—W—NH—, $RCOSCH_2CH_2SSCH_2CH_2O$—$CY_2$—, acyloxymethylphenylmethoxy, (PAOB) $RCO_2$—$C_6H_4$—$CH_2$—O—$RCO_2$—$C_6H_4$—$CH_2$—O—W—, $RCO_2$—$C_6H_4$—$CH_2$—O—W—O—, $RCO_2$—$C_6H_4$—$CH_2$—O—W—S—, $RCO_2$—$C_6H_4$—$CH_2$—O—W—NH—, $RCO_2$—$C_6H_4$—$CH_2$—O—W—$CY_2$—, 1,2-O-diacyl-glyceryloxy, RCOO—$CH_2$—CH(OCOR)—$CH_2O$—, 1,2-O-dialkyl-glyceryloxy, RO—$CH_2$—CH(OR)—$CH_2O$—, 1,2-S-dialkyl-glyceryloxy, RCOO—$CH_2$—CH(SR)—$CH_2O$—, 1-O-alkyl-2-O-acyl-glyceryloxy, RCOO—$CH_2$—CH(OCOR)—$CH_2O$—, 1-S-alkyl-2-O-acyl-glyceryloxy, RS—$CH_2$—CH(OCOR)—$CH_2O$—, 1-O-acyl-2-O-alky-glyceryloxy, RCOO—$CH_2$—CH(OR)—$CH_2O$—, 1-O-acyl-2-S-alky-kglyceryloxy, RCOO—$CH_2$—CH(SR)—$CH_2O$—, or any substitutent attached via a carbon, nitrogen or oxygen atom to a nucleoside di- or tri-phosphate mimic that liberates the di- or tri-phosphate mimic in vivo.

A combination of prodrug moieties may be attached (conjugated) to one or more $X^7$-$X^{10}$ positions on a nucleoside di- or tri-phosphate mimic. W is alkyl, aryl, aralkyl as described above or a heterocycle.

The term microbial infections refer to the infections caused by bacteria, parasite, virus or fungus. Examples of microbes that cause such infections include: *Acanthamoeba*, African Sleeping Sickness (trypanosomiasis), amebiasis, American Trypanosomiasis (Chagas' disease), bilharzia (schistosomiasis), cryptosporidiosis (diarrheal disease, *Cryptosporidium parvum*), giardiasis (diarrheal disease, *Giardia lamblia*), hepatitis A, B, C, D, E, leishmaniasis (skin sores and visceral), malaria (*Plasmodium falciparum*), *Salmonella enteritidis* infection (stomach cramps, diarrhea and fever), *tuberculosis* (*mycobacterium tuberculosis*), varicella (chicken pox), yellow fever, pneumonias, urinary tract infections (*Chlamydia* and *Mycoplasma*), meningitis & meningococcal septicemia, skin and soft tissue infections (*Staphylococcus aureus*), lower respiratory tract infections (bacterial pathogens) or hepatitis C.

Common infections caused by microbes are further outlines in the following chart:

| Infection | Bacteria | Fungus | Protozoa | Virus |
|---|---|---|---|---|
| AIDS | | | | X |
| Athlete's Foot | | X | | |

-continued

| Infection | Bacteria | Fungus | Protozoa | Virus |
|---|---|---|---|---|
| Chicken Pox | | | | X |
| Common Cold | | | | X |
| Diarrheal Disease | X | | X | X |
| Flu | | | | X |
| Genital Herpes | | | | X |
| Malaria | X | | X | |
| Meningitis | X | | | |
| Pneumonia | X | X | | |
| Sinusitis | X | X | | |
| Skin Disease | X | X | X | X |
| Strep Throat | X | | | |
| Tuberculosis | X | | | |
| Urinary Tract Infections | X | | | |
| Vaginal Infections | X | X | | |
| Viral Hepatitis | | | | X |

The term pharmaceutically acceptable carrier refers to a pharmaceutical formulation which serves as a carrier to deliver negatively-charged nucleotide mimics of the present invention into cells. Liposomes, polyethylenimine, and cationic lipids are examples of those carriers.

B. Chemical Synthesis

The nucleotide mimics of the present invention can be prepared using known methodologies in the practice of nucleoside and nucleotide chemistry by those who are ordinarily skilled in the art. The following descriptions are served as representative demonstrations of the preparation of the nucleotide mimics of the present invention.

Novel Nucleosides for the Preparation of Nucleotide Mimics

The novel nucleosides that are used to prepare the nucleotide mimics of the present invention can be synthesized either according to published, known procedures or can be prepared using well-established synthetic methodologies (*Chemistry of Nucleosides and Nucleotides Vol.* 1, 2, 3, edited by Townsend, Plenum Press, 1988, 1991, 1994); *Handbook of Nucleoside Synthesis* by Vorbrüggen Ruh-Pohlenz, John Wiley & Sons, Inc., 2001*; The Organic Chemistry of Nucleic Acids* by Yoshihisa Mizuno, Elsevier, 1986). The nucleosides can be converted to their corresponding diphosphate mimics, and triphosphate mimics by established phosphorylation methodologies.

One of the general approaches for the preparation of novel nucleosides is as follow: 1. properly protected, modified sugars including 1-, 2-, 3-, 4-, 5-substituted furanose derivatives and analogs which are not commercially available need to be synthesized; 2. the modified sugars are condensed with properly substituted purine or pyrimidine derivatives and analogs to yield modified nucleosides; and 3. the resulting nucleosides can be further derivatized at nucleoside level through reactions on the base and/or sugar moieties. Also quite often, natural nucleosides are modified directly to obtain base-modified and sugar-modified nucleosides. There are nucleoside analogs which may have to be synthesized using alternative approaches. For maximal efficiency, the nucleosides may be prepared through solution or solid-phase parallel synthesis. A representative example below (Scheme 1) can demonstrate the process. The 1-O-acetylribofuranose i is condensed with 6-chloro-2-iodopurine to yield the nucleoside ii, which is, at first, subject to a nucleophilic displacement of 6-chloro under a mild condition, then a nucleophilic substitution under a vigorous condition to replace iodo. The resulting compound iii is deprotected to yield nucleoside iv. For use as a starting material for the preparation of nucleotide mimics, a partial deprotection at the 5'-position may be more favorable. Thus, the 2'-, 3'- and 5'-hydroxy groups of the ribose may be protected with different protecting groups and a selective deprotection may be achieved. Here, R', R", and R'" represent a substitutent that may be halogen, R, NHR, $NR_2$, OR, or SR where R is alkyl, alkenyl, alkynyl optionally with one or more heteroatoms.

Scheme 1

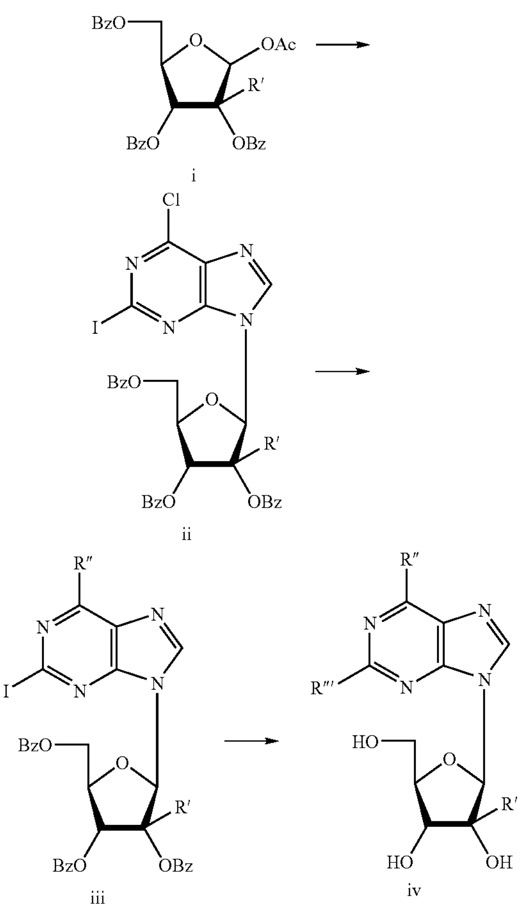

i ii iii iv

Prior publications reported a variety of ribofuranose analogs including ribofuranose derivatives, cyclopentyl derivatives, thioribofuranose derivatives, and azaribofuranose derivatives, which, with appropriate protection and substitution, can be used for the condensations with nucleoside bases. Well-established procedures and methodologies in the literature can be used for the preparation of the modified sugars used in the present invention (Sanhvi et al., *Carbohydrate Modifications in Antisense Research, ACS Symposium Series*, No. 580, American Chemical Society, Washington, D.C., 1994). A large number of 2- and 3-substituted ribofuranose analogs are well documented and can be readily synthesized accordingly (Hattori et al., *J. Med. Chem.* 1996, 39, 5005-5011; Girardet et al., *J. Med. Chem.* 2000, 43, 3704-3713)). A number of 4-, and 5-substituted sugars have also been reported and the procedures and methodologies are useful for the preparation of the modified sugars used in the invention (Gunic et al., *Bioorg. Med. Chem.* 2000, 9, 163-170; Wang et al., *Tetrahedron Lett.* 1997, 38, 2393-2396). Methodologies for the preparation of 4-thiosugars and 4-azasugars are also available (Rassu et al., *J. Med. Chem.* 1997, 40, 168-180; Leydier et al., *Nucleosides Nucleotides* 1994, 13, 2035-2050). Cyclopentyl carbocyclic sugars have been widely used to prepare carbocyclic nucleoside and the preparative procedures are also well documented (Marquez, *In Advances in Antiviral Drug Design*, De Clercq, E. Ed.; JAI press Inc. Vol. 2, 1996; pp 89-146.).

In addition to ribofuranose and cyclopentyl sugars mentioned above, there are other types of novel sugars that also can be used to build novel nucleosides for the preparation of the nucleotide mimics of the present invention. Thus, the sugar moieties of the nucleotide mimics of the present invention may be selected from the group consisting of 1,2-(dihydroxymethyl)-1-ethylcycloprop-1-yl (a, b), 3,4-(dihydroxymethyl)-2-oxacyclobut-1-yl (c), 2,3-(dihydroxymethyl)cyclobut-1-yl (d), 3-hydroxymethyl-2,4-dioxacyclopent-1-yl (e), 3-hydroxymethyl-2-oxa-4-thiacyclopent-1-yl (f), 3-hydroxymethyl-2-thia-4-oxacyclopent-1-yl (g), 3-hydroxymethyl-2-methylenecyclopent-1-yl (h), 4-hydroxymethyl-2-cyclopenten-1-yl (i), and 2,3-dideoxy-2,3-didehydro-β-D-ribofuranosyl (j). The structures of these sugar moieties are shown in the chart below. In the chart the open bonding sites are the sites to where nucleoside bases are linked. The synthesis of these sugar analogs or novel nucleosides containing these sugar moieties has been reported before (Sekiyama et al., *J. Med. Chem.* 1998, 41, 1284-1298; Norbeck et al., *Tetrahedron Lett.* 1989, 33, 6263; Kim et al., *Tetrahedron Lett.* 1992, 33, 6899; Jeong et al. *J. Med. Chem.* 1993, 36, 181; Bisacchi et al, *Bioorg. Med. Chem. Lett.* 1997, 7, 127; Huang et al., *Nucleosides Nucleotides* 1995, 14, 195-207).

a

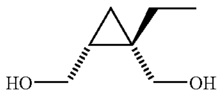

b

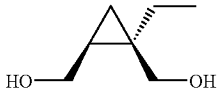

c

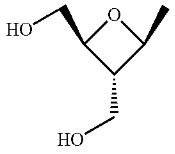

d

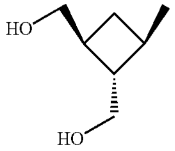

e

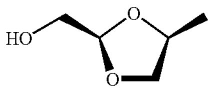

f

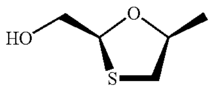

g

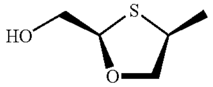

-continued h

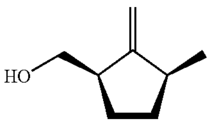

i

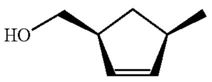

j

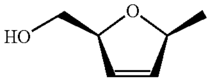

A variety of purine analogs, pyrimidine analogs, and other heterocycles as nucleoside bases have been well documented (*Chemistry of Nucleosides and Nucleotides* Vol 1, 2, 3, edited by Townsend, Plenum Press, 1988, 1991, 1994). The condensations of sugars with nucleoside bases to yield nucleosides are the most frequently used reactions in nucleoside chemistry. Well-established procedures and methodologies can be found in the literature (Vorbruggen et al., *Chem. Ber.* 1981, 114, 1234-1268, 1279-1286; Wilson et al., *Synthesis,* 1995, 1465-1479). There are several types of standard condensation reactions widely used, including: 1. trimethylsilyl triflate-catalyzed coupling reaction between 1-O-acetylribofuranose derivatives and silylated nucleoside bases, often used for the preparation of ribonucleosides; 2. tin chloride-catalyzed coupling reactions between 1-O-methyl or 1-O-acetylribofuranose derivatives and silylated nucleoside bases, often used to prepare 2'-deoxyribonucleosides; 3. SN2 type substitutions of 1-halosugar by nucleoside bases in the presence of a base such as sodium hydride for the preparation of both ribonucleosides and 2'-deoxyribonucleosides; and 4. less often used, but still useful, fusion reactions between sugars and nucleoside bases without solvent.

A large number of known nucleosides are prepared from the modifications of purine and pyrimidine nucleosides. The modifications can be done on the sugars and/or nucleoside bases. A simple, widely-used reaction is the nucleophilic substitution of halopurine or halopyrimidine base by a variety of nucleophiles such as hydroxide, ammonia, hydrogen sulfide, alkoxides, amines, alkylthiol, hydrazine, hydroxyamines, azide, cyanide, and hydride. This type of reactions can be very useful for preparation of 2-substituted purine nucleoside, 6-substituted purine nucleosides, 8-substituted purine nucleosides, 2,6-disubstituted purine nucleosides, 2,8-disubstituted purine nucleosides, 6,8-disubstituted purine nucleosides, 2,6,8-trisubstituted purine nucleosides (Halbfinger et al., *J. Med. Chem.* 1999, 42, 5323-5337, Lin et al., *J. Med. Chem.* 1985, 28, 1481-1485; Bressi et al., *J. Med. Chem.* 2000, 43, 4135-4150). These substitution reactions are readily extended to purine nucleoside analogs such as 7-deazapurine nucleosides, 7-deaza-8-azapurine nucleosides, 8-azapurine nucleosides, 3-deazapurine nucleosides, 3-deaza-8-azapurine nucleosides, and 3,8-dideazapurine nucleosides. For instance, a number of 7-deaza-7-substituted purine nucleoside have been prepared through such substitutions (Ugarkar et al., *J. Med. Chem.* 2000, 43, 2894-2905). The same methodologies can be used for the preparation of 4-substituted pyrimidine nucleosides, 5-substituted pyrimidine nucleosides, 4,5-disubstituted pyrimidine nucleosides, 5-substituted 6-azapyrimidine nucleosides, 5-substituted 6-azapyrimidine nucleosides, and 4,5-disubstituted 6-azapyrimidine nucleosides.

The sugar moieties of synthesized nucleosides can be further modified. There are a variety of reactions which can be used to modify the sugar moiety of nucleosides. The reactions frequently used include deoxygenation, oxidation/addition, substitution, and halogenation. The deoxygenations are useful for the preparation of 2'-deoxy-, 3'-deoxy-, and 2',3'-dideoxy-nucleosides. A widely-used reagent is phenyl chlorothionoformate, which reacts with the hydroxy of nucleosides to yield a thionocarbonate. The treatment of the thionocarbonate with tributyltin hydride and AIBN yields deoxygenated nucleosides. The oxidation/addition includes the conversion of a hydroxy group to a carbonyl group, followed by a nucleophilic addition, resulting in C-alkylated nucleosides and C-substituted nucleosides. The substitution may be just a simple displacement of a hydroxyl proton by alkyl, or may be a conversion of a hydroxyl to a leaving group, followed by a nucleophilic substitution. The leaving group is usually a halogen, mesylate, tosylate, nisylate, or a triflate. A variety of nucleophiles can be used, resulting in 2-, or 3-substituted nucleosides. Halogenation can be used to prepare 1'-halo-, 2'-halo-, 3'-halo-, or 4'-halonucleosides. Chlorination and fluorination are commonly used and result in important fluoro-sugar and chloro-sugar nucleosides.

Clinically-used nucleoside drugs can be phosphorylated by cellular enzymes and maintain Watson-Crick hydrogen bonding between base pairs. However, a large number of novel nucleosides synthesized may not be phosphorylated by a cellular enzyme and may not show in vitro or in vivo biological activities. It would be of a great value to convert some inactive nucleosides into active nucleotide mimics and to convert some moderately-active ones into potent nucleotide mimics. One approach provided in the present invention is to convert the nucleosides to the nucleotide diphosphate mimics or nucleoside triphosphate mimics, which themselves can be active chemical entities since cellular phsosphorylation is no longer necessary.

While some nucleotide mimics may be prepared from the reactions of carbohydrate-phosphate mimics with heterocycles, most of the nucleotide mimics of the present invention are prepared from nucleosides including, but not limited to, the following:

adenosine,
cytidine,
guanosine,
uridine,
2'-deoxyadenosine,
2'-deoxycytidine,
2'-deoxyguanosine,
thymidine,
inosine,
9-(β-D-arabinofuranosyl)adenine,
1-(β-D-arabinofuranosyl)cytosine,
9-(β-D-arabinofuranosyl)guanine,
1-(β-D-arabinofuranosyl)uracil,
9-(β-D-arabinofuranosyl)hypoxanthine,
1-(β-D-arabinofuranosyl)thymine,
3'-azido-3'-deoxythymidine,
3'-azido-2',3'-dideoxyuridine,
3'-azido-2',3'-dideoxycytidine,
3'-azido-2',3'-dideoxyadenosine,
3'-azido-2',3'-dideoxyguanosine,
3'-azido-2',3'-dideoxyinosine,
3'-deoxythymidine,
2',3'-dideoxyuridine,
2',3'-dideoxyinosine,
2',3'-dideoxyadenosine,
2',3'-dideoxycytidine,
2',3'-dideoxyguanosine,
9-(2,3-dideoxy-1-β-D-ribofuranosyl)-2,6-diaminopurine,
3'-deoxy-2',3'-didehydrothymidine,
2',3'-didehydro-2',3'-dideoxyuridine,
2',3'-didehydro-2',3'-dideoxycytidine,
2',3'-didehydro-2',3'-dideoxyadenosine,
2',3'-didehydro-2',3'-dideoxyguanosine,
2',3'-didehydro-2',3'-dideoxyinosine,
3-deazaadenosine,
3-deazaguanosine,
3-deazainosine,
7-deazaadenosine,
7-deazaguanosine,
7-deazainosine,
6-azauridine,
6-azathymidine,
6-azacytidine,
5-azacytidine,
9-(β-D-ribofuranosyl)-6-thiopurine,
6-methylthio-9-(β-D-ribofuranosyl)purine,
2-amino-9-(β-D-ribofuranosyl)-6-thiopurine,
2-amino-6-methylthio-9-(β-D-ribofuranosyl)purine,
5-fluorocytidine,
5-iodocytidine,
5-bromocytidine,
5-chlorocytidine,
5-fluorouridine,
5-iodouridine,
5-bromouridine,
5-chlorouridine,
2'-C-methyladenosine,
2'-C-methylcytidine,
2'-C-methylguanosine,
2'-C-methylinosine,
2'-C-methyluridine,
2'-C-methylthymidine,
2'-deoxy-2'-fluoroadenosine,
2'-deoxy-2'-fluorocytidine,
2'-deoxy-2'-fluoroguanosine,
2'-deoxy-2'-fluorouridine,
2'-deoxy-2'-fluoroinosine,
2'-α-fluorothymidine,
2'-deoxy-2'-fluoroarabinoadenosine,
2'-deoxy-2'-fluoroarabinocytidine,
2'-deoxy-2'-fluoroarabinoguanosine,
2'-deoxy-2'-fluoroarabinouridine,
2'-deoxy-2'-fluoroarabinoinosine,
2'-β-fluorothymidine,
2'-O-methyladenosine,
2'-O-methylcytidine,
2'-O-methylguanosine,
2'-O-methylinosine,
2'-O-5-dimethyluridine,
2'-C-ethynylcytidine,
2'-C-ethynylguanosine,
2'-C-ethynyluridine,
2'-C-ethynylinosine,
2'-C-ethynyl-5-methyluridine,
3'-C-ethynyladenosine,
3'-C-ethynylcytidine,
3'-C-ethynylguanosine,
3'-C-ethynyluridine,
3'-C-ethynylinosine,
3'-C-ethynyl-5-methyluridine, 3'-deoxyadenosine,
3'-deoxycytidine,
3'-deoxyguanosine,
3'-deoxyuridine,
3'-deoxyinosine,
4'-C-ethynyladenosine,
4'-C-ethynylcytidine,
4'-C-ethynylguanosine,
4'-C-ethynyluridine,
4'-C-ethynylinosine,
4'-C-ethynylthymidine,
4'-C-methyladenosine,
4'-C-methylcytidine,
4'-C-methylguanosine,
4'-C-methyluridine,
4'-C-methylinosine,
4'-C-methylthymidine,
2'-C-methyl-7-deazaadenosine,
2'-C-methyl-7-deazaguanosine,
2'-C-methyl-3-deazaadenosine,
2'-C-methyl-3-deazaguanosine,
2'-O-methyl-7-deazaadenosine,
2'-O-methyl-7-deazaguanosine,
2'-O-methyl-3-deazaadenosine,
2'-O-methyl-3-deazaguanosine
2'-C-methyl-6-azauridine,
2'-C-methyl-5-fluorouridine,
2'-C-methyl-5-fluorocytidine,
2'-C-methyl-2-chloroadenosine,
2'-deoxy-7-deazaadenosine,
2'-deoxy-3-deazaadenosine,
2'-deoxy-7-deazaguanosine,
2'-deoxy-3-deazaguanosine,
2'-deoxy-6-azauridine,
2'-deoxy-5-fluorouridine,
2'-deoxy-5-fluorocytidine,
2'-deoxy-5-iodouridine,
2'-deoxy-5-iodocytidine,
2'-deoxy-2-chloroadenosine,
2'-deoxy-2-fluoroadenosine,
3'-deoxy-7-deazaadenosine,
3'-deoxy-7-deazaguanosine,
3'-deoxy-3-deazaadenosine,
3'-deoxy-3-deazaguanosine,
3'-deoxy-6-azauridine,
3'-deoxy-5-fluorouridine,
3'-deoxy-5-iodouridine,
3'-deoxy-5-fluorocytidine,
3'-deoxy-2-chloroadenosine,
2',3'-dideoxy-7-deazaadenosine,
2',3'-dideoxy-7-deazaguanosine,
2',3'-dideoxy-3-deazaadenosine,
2',3'-dideoxy-3-deazaguanosine,
2',3'-dideoxy-6-azauridine,
2',3'-dideoxy-5-fluorouridine,
2',3'-dideoxy-5-fluorouridine,
2',3'-dideoxy-5-iodocytidine,
2',3'-dideoxy-2-chloroadenosine,
2',3'-dideoxy-β-L-cytidine,
2',3'-dideoxy-β-L-adenosine,
2',3'-dideoxy-β-L-guanosine,
3'-deoxy-β-L-thymidine,
2',3'-dideoxy-5-fluoro-β-L-cytidine,
β-L-thymidine,
2'-deoxy-β-L-cytidine,
2'-deoxy-β-L-adenosine,
2'-deoxy-β-L-guanosine,
2'-deoxy-β-L-inosine,
β-L-cytidine,
β-L-adenosine,
β-L-guano sine,
β-L-uridine,
β-L-inosine,
2',3'-didehydro-2',3'-dideoxy-β-L-cytidine,
2',3'-didehydro-3'-dideoxy-β-L-thymidine,
2',3'-didehydro-2',3'-dideoxy-β-L-adenosine,
2',3'-didehydro-2',3'-dideoxy-β-L-guanosine,
2',3'-didehydro-2',3'-dideoxy-β-L-5-fluorocytidine,
2'-deoxy-2',2'-difluorocytidine,
9-(β-D-arabinofuranosyl)-2-fluoroadenine,
2'-deoxy-2'(E)-fluoromethylenecytidine,
2'-deoxy-2'(Z)-fluoromethylenecytidine,
(−)-2',3'-dideoxy-3'-thiacytidine,
(+)-2',3'-dideoxy-3'-thiacytidine
1-β-D-ribofuranosyl-1,2,4-triazole-3-carboxamide,
1-β-L-ribofuranosyl-1,2,4-triazole-3-carboxamide,
1-β-D-ribofuranosyl-1,3-imidazolium-5-olate,
1-β-L-ribofuranosyl-1,3-imidazolium-5-olate,
1-β-D-ribofuranosyl-5-ethynylimidazole-4-carboxamide,
1-β-L-ribofuranosyl-5-ethynylimidazole-4-carboxamide,
1-(2-deoxy-2-fluoro-β-D-arabinofuranosyl)-5-iodouracil,
1-(2-deoxy-2-fluoro-β-D-arabinofuranosyl)-5-iodocytosine,
1-(2-deoxy-2-fluoro-β-L-arabinofuranosyl)-5-methyluracil,
1-β-D-arabinofuranosyl-E-5-(2-bromovinyl)uracil,
E-5-(2-bromovinyl)-2'-deoxyuridine,
5-trifluoromethylthymidine,
1-β-D-arabinofuranosyl-5-propynyluracil,
1-(2-deoxy-2-fluoro-1-β-D-arabinofuranosyl)-5-ethyluracil,
2',3'-dideoxy-3'-fluoroguanosine,
3'-deoxy-3'-fluorothymidine,
(±)-(1α,2β,3α)-9-[2,3-bis(hydroxymethyl)-1-cyclobutyl]adenine,
(±)-(1α,2β,3α)-9-[2,3-bis(hydroxymethyl)-1-cyclobutyl]guanine,
(±)-(1β,2α,3β)-9-[2,3-bis(hydroxymethyl)-1-cyclobutyl]guanine,
(±)-(1β,2α,3β)-9-[2,3-bis(hydroxymethyl)-1-cyclobutyl]adenine,
(1R,3S,4R)-9-(3-hydroxy-4-hydroxymethylcyclopent-1-yl)guanine,
(1S,2R,4R)-9-(1-hydroxy-2-hydroxymethylcyclopent-4-yl)guanine,
(2R,4R)-9-(2-hydroxymethyl-1,3-dioxolan-4-yl)-2,6-diaminopurine,
(2R,4R)-1-(2-hydroxymethyl-1,3-dioxolan-4-yl)cytosine,
(2R,4R)-9-(2-hydroxymethyl-1,3-dioxolan-4-yl)guanine,
(2R,4R)-1-(2-hydroxymethyl-1,3-dioxolan-4-yl)-5-fluorocytosine,
(1R,2S,4S)-9-(4-hydroxy-3-hydroxymethyl-2-methylenecyclopent-4-yl]guanine, or
(1S,3R,4S)-9-(3-hydroxy-4-hydroxymethyl-5-methylenecyclopent-1-yl]guanine.

Nucleotide Mimics

Conversion of nucleosides to nucleoside diphosphates or nucleoside triphosphates can be achieved according to published procedures. Certain nucleoside diphosphate mimics and nucleoside triphosphate mimics also have been reported. Many nucleotide mimics of the present invention can be prepared by similar approaches as published or by using well-known knowledge of organic phosphorus chemistry. Scheme 3 and 4 show the general methodologies for the preparation of nucleoside diphosphate mimics and nucleoside triphosphate mimics, respectively.

Most of the nucleotide diphosphate mimics and nucleoside triphosphate mimics of the present invention can be prepared using the methodologies shown in Scheme 2 and 3 where a protected ribonucleoside v is used as an example. The ribonucleoside v is converted to the nucleoside derivative vi having a leaving group such as an iodo, tosylate or triflate at the 5'-position. The reaction of vi with a tri- or tetraalkylammonium salt of pyrophosphate or a diphosphate mimic yields the nucleoside diphosphate mimic vii, which is subject to a deprotection to yield the nucleoside diphosphate mimic viii. Alternatively, vii can be prepared from the reaction of the nucleoside v with diphosphate mimic chloridate such as methylenediphosphonate tetrachloridate and a subsequent hydrolysis. In Scheme 3, compound v is converted to an activated form of nucleoside phosphate or phosphite ix, which is treated with a tri- or tetraalkylammonium salt of pyrophosphate or a diphosphate mimic to yield nucleoside triphosphate mimic x. Alternatively, x can be prepared from the reaction of vii with a tri- or teraalkylammonium salt of monophosphate or a monophosphate mimic. The deprotection of x affords the nucleoside triphosphate mimics xi. Here R' represents a protecting group such as acetyl, benzoyl, benzyl, isopropylidene, a silyl group, trityl, or dimethoxytrityl; X' is a leaving group including halogen, and sulfonates; AP represent an activated phosphate such as monophosphate imidazolate, an active phosphine such as bis(diisopropylamino)phosphine or an activated phosphite; Y' is O, S, NH, substituted amino, methylene, ethylene, and halomethylene; Y" can be a variety of univalent substitutents including H, OH, SH, $NH_2$, F, $N_3$, CN, and $^-BH_3M^+$, or selected from alkyl, alkoxy, alkenyl, and alkynyl optionally containing one or more heteroatoms. In addition to the general methodologies shown in Scheme 2 and 3, there are other less frequently-used methods, which are also used to prepare the nucleotide mimics of the present inventions. Some of the methods are shown in the following descriptions.

Scheme 3
General methodologies for the preparation of nucleotide triphosphate mimics

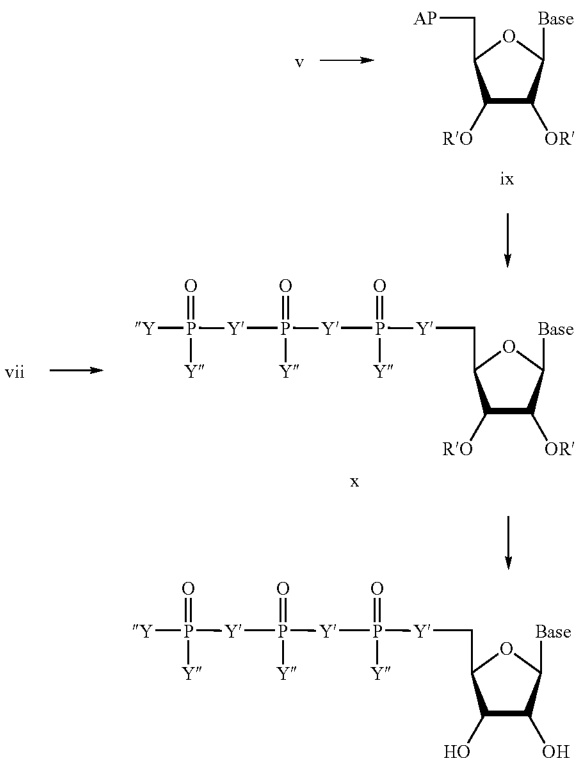
v
ix
vii
x
xi

The Purification and Analysis of Nucleotide Mimics and their Prodrugs

The compounds were purified by anion exchange (AX) chromatography using a 10×160 mm Mono Q column Scheme 2
General methodologies for the preparation of nucleotide diphosphate mimics

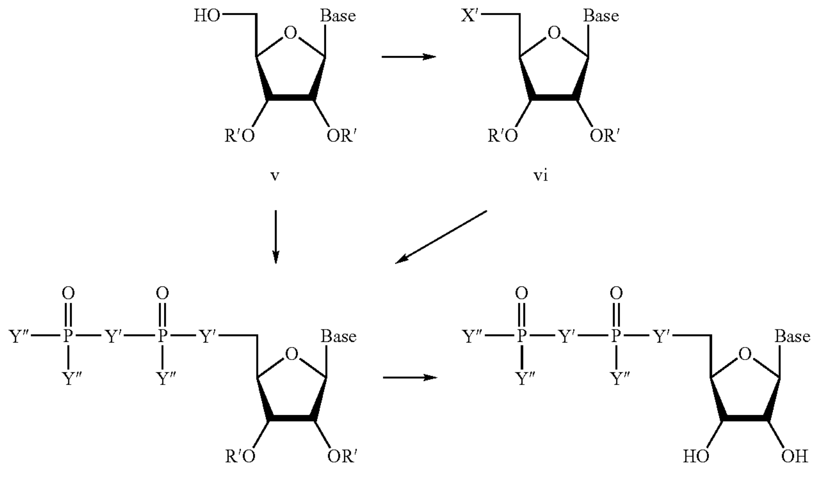
v
vi
vii
viii (Pharmacia). Initial conditions were typically 0 to 35 mM NaCl. Elution gradients were typically a linear gradient from 0 to 35 mM to 350 mM NaCl to 1 M NaCl in two to three column volumes at 6.5 ml/min. A constant concentration of 50 mM Tris, pH 8 was maintained throughout the purification. Fractions from anion exchange chromatography containing the target compound were collected and desalted by reversed phase (RP) chromatography using a Luna C18 250×21 mm column (Phenomenex) with a flow rate of 10 ml/min. Elution gradients were generally from 0-20% to 95% methanol in 20-60 min at a constant concentration of triethylammonium acetate (50 mM). Compounds that did not require AX-HPLC purification were purified by Reverse-phase HPLC only. However, most nucleotide mimics in the example section, unless specified, were purified using both ion-exchange HPLC and reverse-phase HPLC as indicated simply by HPLC.

Mass Spectra and purity of the nucleotide mimics and their prodrugs were determined using on-line HPLC mass spectrometry on a ThermoFinnigan (San Jose, Calif.) Deca XP plus. A Phenomenex Luna (C18(2) or c5), 75×2 mm, 3-um particle size was used for RP HPLC. A 0 to 50% linear gradient (15 min) of AcCN in 10 mM NNDMHA, pH 7 was performed in series with mass spectra detection in the negative ionization mode. Nitrogen gas and a pneumatic nebulizer were used to generate the electrospray. The mass range of 150-1500 was typically sampled.

The Preparation of Nucleoside 5'-Diphosphate Mimics

In many cases, 3'-azido-3'-deoxythymidine serves as an example to illustrate various approaches and reactions. The approaches and methodologies shown below are general and can be applied to the preparation of other nucleotide mimics of the present invention although in some cases nucleosides may need appropriate protection. The detailed procedures are given in the section of Examples.

The preparation of nucleoside 5'-diphosphate mimics can be readily achieved through the reactions of nucleosides with modified diphosphotetrachloridates $Cl_2P(O)$—X—P(O)$Cl_2$ (X═NH, $CH_2$, $CF_2$, $CCl_2$, CHF, etc). For example, 2'-deoxy-2'-fluoromethylenecytidine was reacted with trichloro[(dichlorophosphoryl)imido]-phosphorane and methylenediphosphotetrachloridate to give, after hydrolysis, 2'-deoxy-2'-fluoromethylenecytidine 5'-imidodiphosphate (3) and 2'-deoxy-2'-fluoromethylenecytidine 5'-methylene-diphosphonate (4), respectively. Similarly, the nucleoside ethylenediphosphonate 80 was prepared. A number of other nucleoside 5'-diphosphate mimics were prepared through similar reactions, including 2'-deoxy-2',2'-difluorocytidine 5'-diphosphate mimics (5-7, 81) and 3'-azido-3'-deoxythymidine 5'-imidodiphosphate (8).

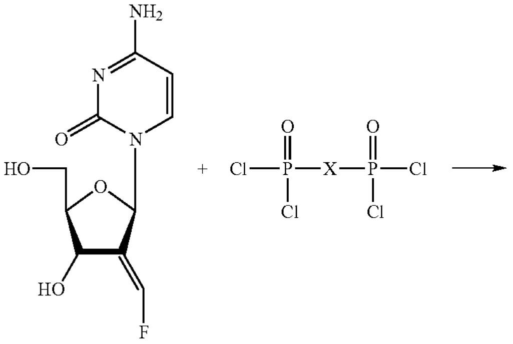

(1)

-continued

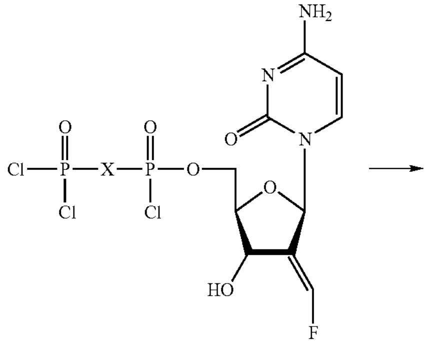

(2)

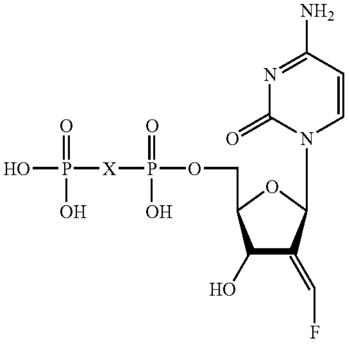

3 X = NH
4 X = $CH_2$
80 X = $CH_2CH_2$

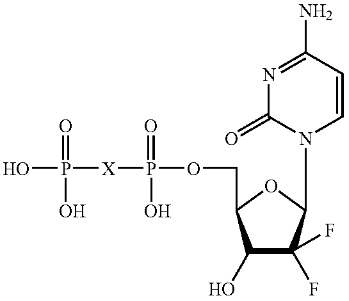

5 X = $CH_2$
6 X = NH
7 X = $CF_2$
81 X = $CH_2CH_2$

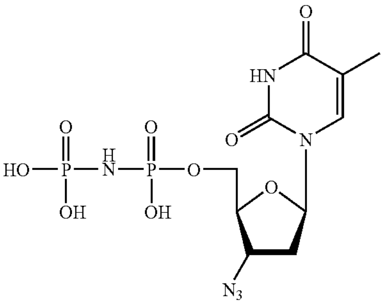

(8)

An alternative approach is to convert the 5'-hydroxy of a nucleoside to a leaving group, which is reacted with the tetrabutylammonium salt of diphosphate mimics to give nucleoside diphosphate mimics. For example, 3'-azido-3'-deoxythymidine was converted to the 5'-tosylate 9, which was treated with the tetrabutylammonium salt of difluoromethylenediphosphonate to give 3'-azido-3'-deoxythymidine 5'-(difluoromethylene)diphosphonate (10).

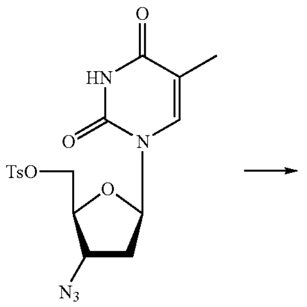

(9)

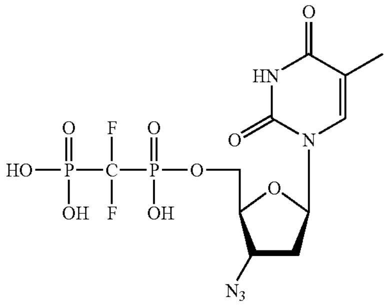

(10)

3'-Azido-3'-deoxythymidine 5'-α-P-borano-β-P-methyl-diphosphate (13) was prepared through the activated phoshoramidite 12. The reaction of 12 with excess methylphosphonate monotributylammonium salt, followed by treatment with borane diisopropylethyl amine complex and subsequent hydrolysis to give the diphosphate mimic 13. Through this approach a variety of nucleoside 5'-β-P-substituted diphosphates can be prepared.

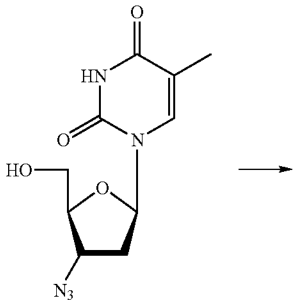

(11)

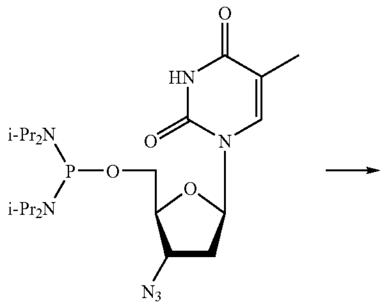

(12)

-continued

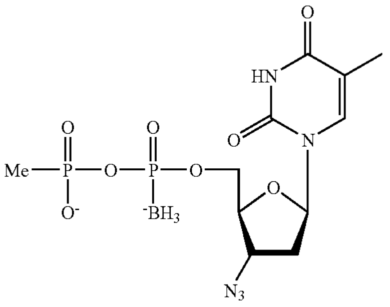

(13)

The Preparation of Nucleoside Triphosphate Mimics

Since triphosphate mimics are more diverse than diphosphate mimics, there are more synthetic approaches for the preparation of nucleoside triphosphate mimics. One approach includes the preparation of an activated phosphate or phosphite linked to the 5'-position of a nucleoside and a subsequent condensation with diphosphate mimics. Many nucleoside triphosphate mimics of the present invention were prepared through this approach. For example, the reaction of 3'-azido-3'-deoxythymidine with 2-chloro-4H-1,3,2-benzodioxaphosphorin-4-one gives the intermediate 14, which is condensed with diphosphate mimics to form a cyclic triphosphate intermediate 15. The treatments of the cyclic triphosphate intermediate 15 with different reagents yield, after hydrolysis, a variety of nucleoside triphosphate mimics 17. The scheme below demonstrates the reaction path. Here, X is O, S, NH, methylene, or halomethylene; Y is O, S, $N_3$, alkoxy, aryloxy, alkylamino, arylamino, or $^-BH_3M^+$; $R_4N^+$ is an ammonium, trialkylammonium, or tetraalkylammonium cation such as $NH_4^+$, $Et_3NH^+$, $Bu_3NH^+$, and $Bu_4N^+$.

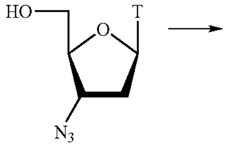

(11)

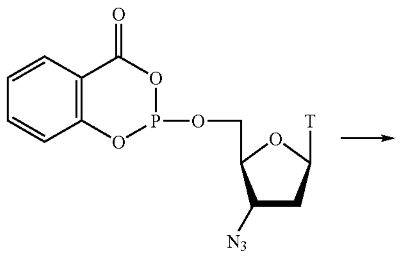

(14)

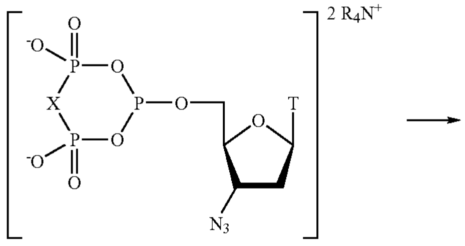

(15)

-continued

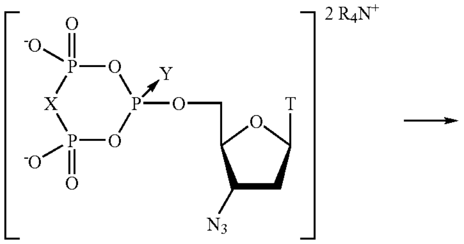

(16)

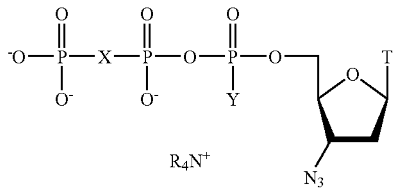

(17)

When the cyclic intermediate 15 was treated with $BH_3$-amine complex or $BH_3$-sulfide complex, followed by hydrolysis with water, a number of nucleoside 5'-α-P-boranotriphosphate mimics were prepared. This methodology is a general method and can be applied to a variety of nucleosides, however, an appropriate protection is necessary for nucleosides bearing reactive groups. A representative example is shown below. 7-Deaza-2'-C-methyladenosine (18) was converted to 7-deaza-2'-C-methyl-2',3'-O-6-tri-acetyladenosine (20), which was subject to the reactions shown above to give the triacetyl nucleoside triphosphate mimic 20. A deprotection with aqueous ammonia or methanolic ammonia yielded the nucleoside triphosphate mimic 22.

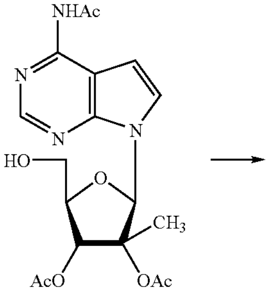

(18)

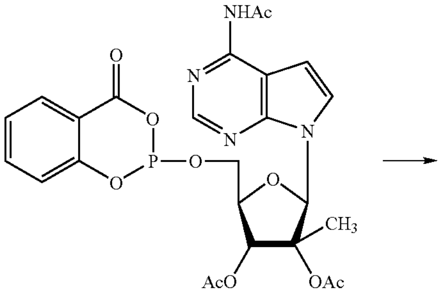

(19)

-continued

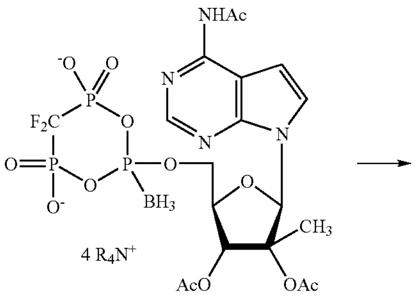

(20)

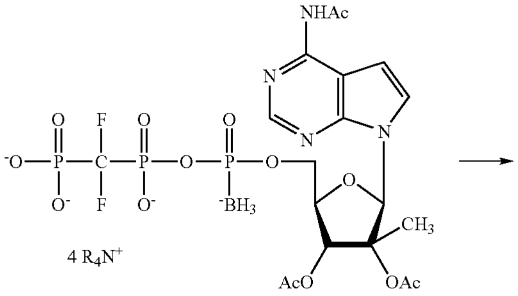

(21)

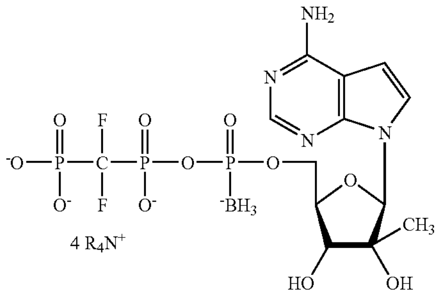

(22)

Other representative nucleoside 5'-α-P-boranotriphosphate mimics 23-28 containing different β,γ-bridging modifications were synthesized through the same approach and are shown below.

(23)

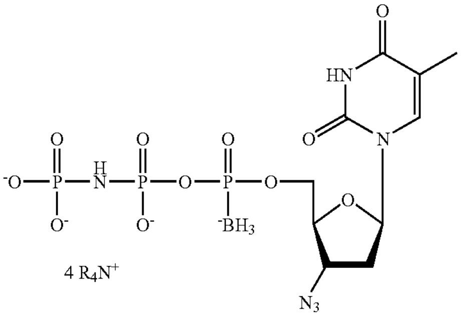

-continued (24)

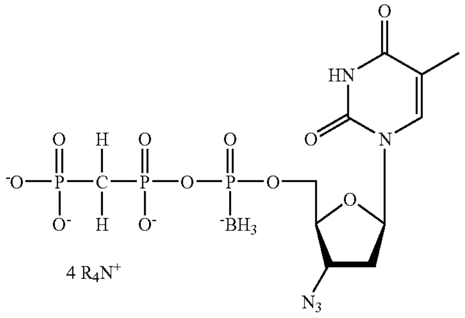

(25)

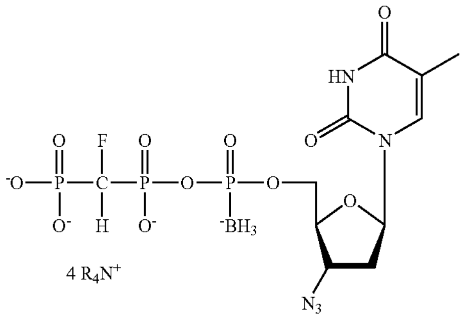

(26)

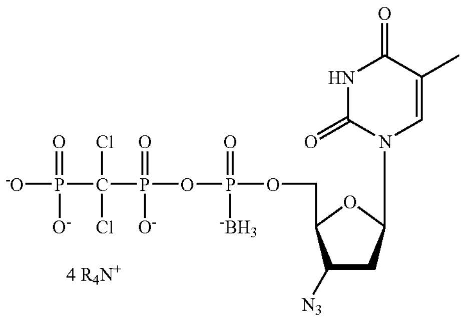

(27)

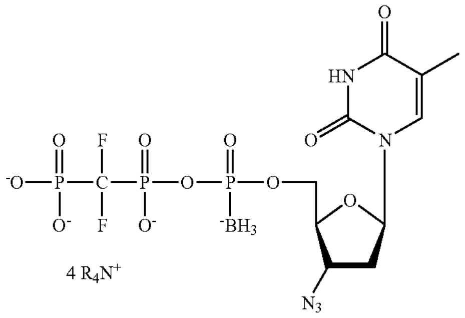

(28)

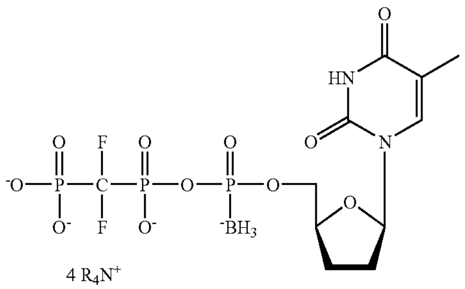

Similarly, the treatment of 15 with elemental sulfur and subsequent reaction with water gave the α-P-thiotriphosphate mimics 29. Compound 30 was also prepared through the same method. Compound 31 was obtained from the treatment of a cyclic triphosphate equivalent to 15 with sulfur and subsequent reaction with lithium sulfide. Similarly, compound 32 was prepared from the treatment of the cyclic triphosphate with borane-diisopropylethylamine complex and subsequent reaction with lithium sulfide.

(29)

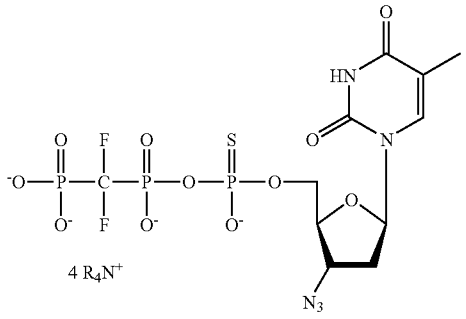

(30)

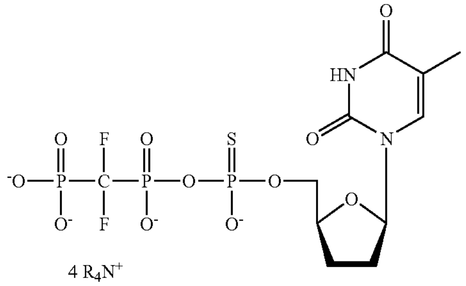

(31)

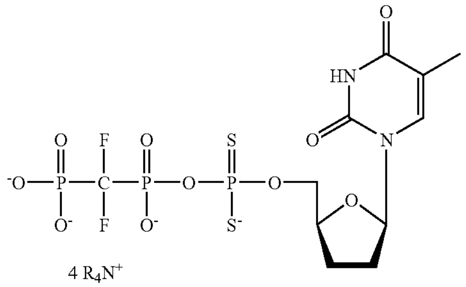

(32)

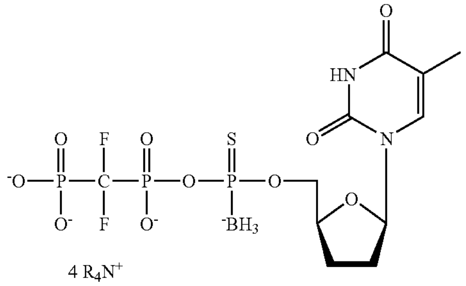

Alternatively, the treatment of the cyclic triphosphate intermediate 15 with iodine followed by reaction with a nucleophile can yield a variety of nucleoside 5'-α-P-substituted triphosphate mimics. For example, the reaction of 15 with iodine, followed by treatment with ethylamine and aniline yielded the α-P-aminotriphosphate mimics 33 and 34, respectively. When potassium fluoride, sodium azide, sodium phenoxide, and sodium methoxide were chosen as the nucleophile, compounds 35-38 were prepared, respectively. Compound 39 was also formed when the nucleophile was hydroxyamine.

(33)

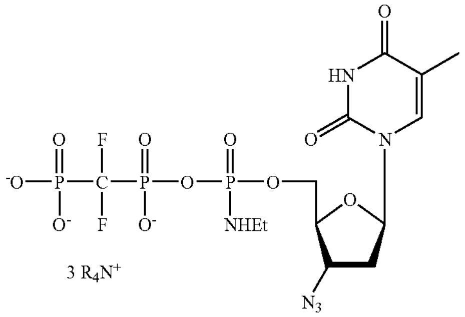

(34)

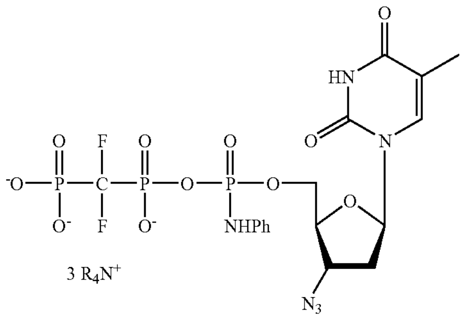

(35)

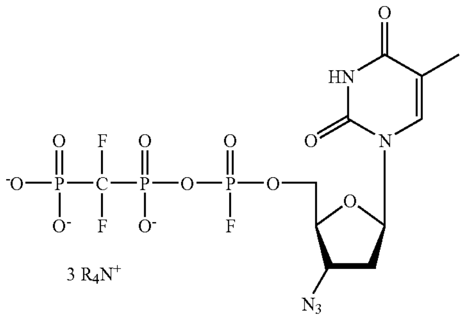

(36)

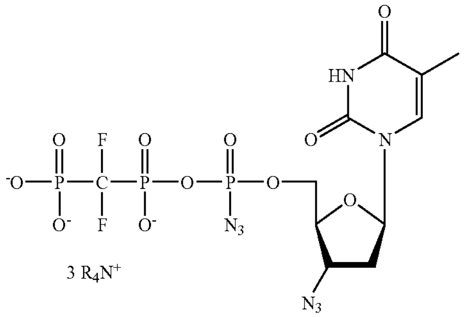

(37)

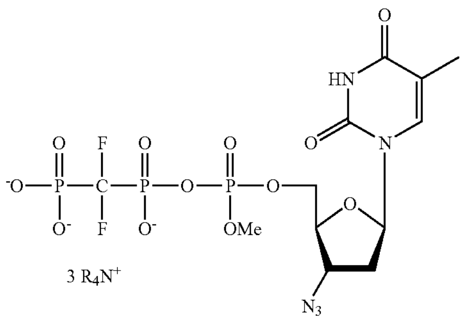

-continued (38)

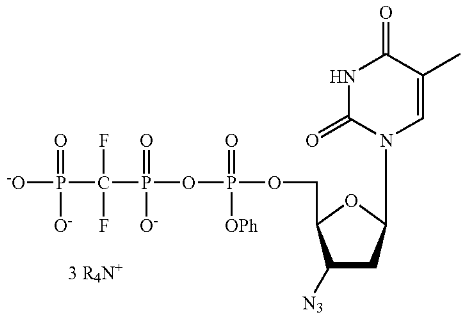

(39)

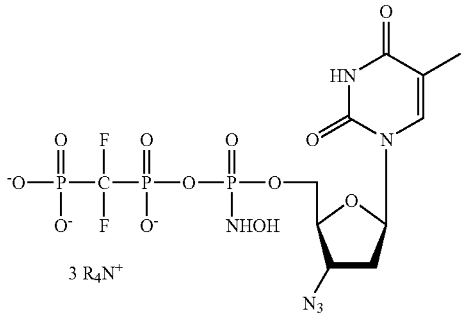

Nucleoside 5'-γ-P-substituted triphosphate mimics can be prepared through a few different approaches. One approach is the alkylation of nucleoside triphosphate mimics with a reagent bearing a leaving group. The alkylating reagent may be a halide such as a bromide and iodide or a sulfonate such as a tosylate, nisylate, and triflate. This type of reaction can be used to introduce a small aliphatic hydrocarbon or a large moiety such as lipids and other phosphate-masking moieties. For example, the reaction of the tetrabutylammonium salt of the nucleotide mimic 27 with methyl triflate yielded the γ-P-methyltriphosphate mimic 40. Similarly, the γ-P-palmityltriphosphate mimic 41 was prepared from the reaction of 27 with palmityl p-nitrobenzenesulfonate.

(40)

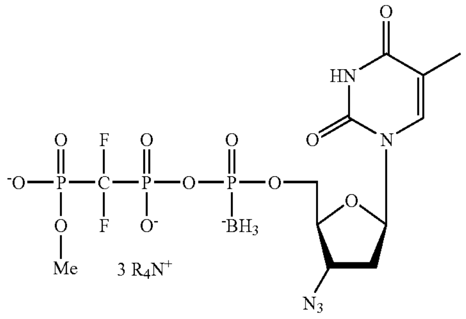

(41)

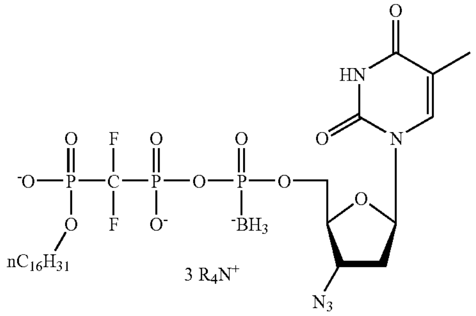

Compounds 42 and 43 were prepared, respectively, through the treatment of the nucleoside triphosphate mimic 27 with DCC and subsequent reaction with phenol and p-nitrophenol. This reaction represents a general approach for the attachment of aryloxy substitutents at the γ-P position of nucleoside triphosphate mimics.

(42)

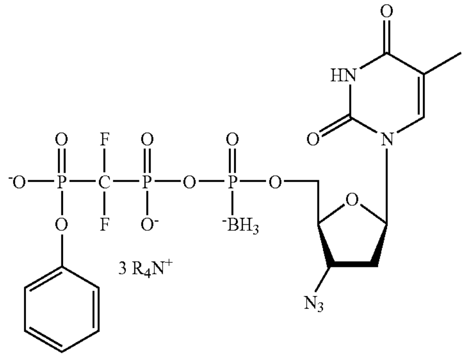

(43)

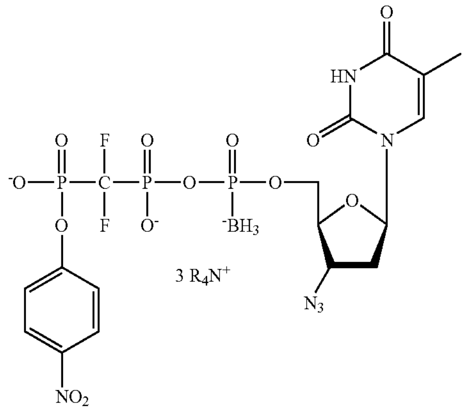

Another approach for the preparation of the nucleoside 5'-γ-P-substituted triphosphate mimics is the reaction of nucleoside diphosphate mimics with substituted phosphonodichloridate as shown below. For example, the treatment of 3'-azido-3'-deoxythymidine 5'-(difluoromethylene) diphosphonate (10) with methylphosphonodichloridate yields, after hydrolysis, the triphosphate mimics 44. Similarly, the compound 45 containing γ-P-phenyl-α,β-(difluoromethylene)triphosphate was prepared.

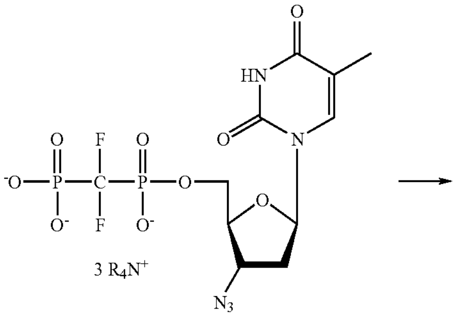

(10)

-continued

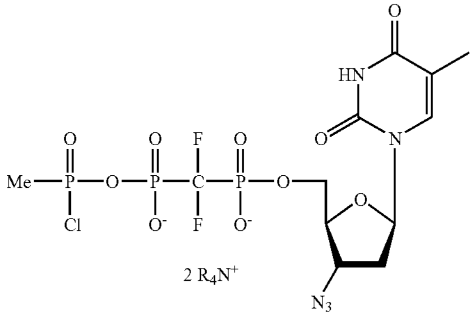

(44)

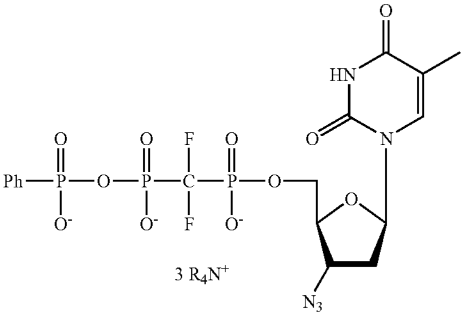

(45)

An additional approach for the preparation of nucleoside 5'-γ-P-substituted triphosphate mimics 47 is the reaction of nucleoside 5'-phosphodichloridate 46 or 5'-phophonodichloridate with substituted pyrophosphate or substituted diphosphate mimics. Also, the reaction of the nucleoside cyclic phosphate 14 with substituted pyrophosphate or substituted diphosphate mimics, followed by treatment with oxidizing reagents such as sulfur, iodine, and borane and then with nucleophiles, can yield a variety of nucleoside 5'-γ-P-(and/or α-P)-substituted triphosphate mimics 48. Through this approach substitutents such as γ-P-alkyl, γ-P-alkylamino, γ-P-alkylthio, γ-P-alkoxy, γ-P-aryl, γ-P-aryloxy, and γ-P-arylamino can be introduced.

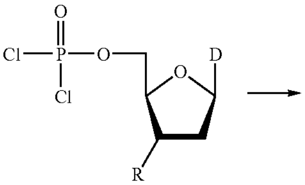

(46)

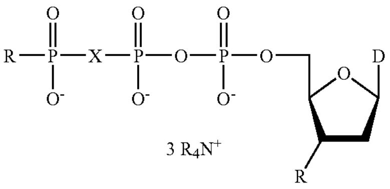

(47)

-continued

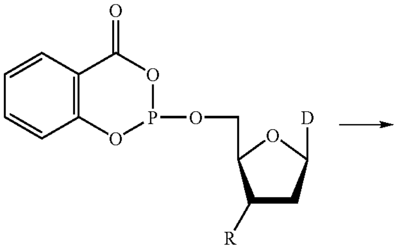

(14)

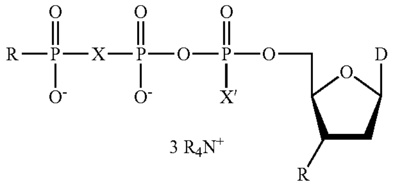

(48)

The present invention also provides approaches for the preparation of nucleoside triphosphate mimics in which the modifications are present at the 5'-position of the nucleotide mimics. The 5'-oxygen of nucleotide mimics can be replaced with other heteroatoms, methylene, halomethylene or dihalomethylene. Alternatively, the 5'-oxygen can be eliminated. Two examples shown below are used to illustrate the preparation of these compounds. The first scheme shows the synthesis of 3'-azido-3'-deoxythymidine 5'-deoxy-β,γ-(difluoromethylene)triphosphate. 1-(2-Deoxyxylofuranosyl) thymine was converted to a 5'-iodo derivative, which was subjected to acetylation. The resulting intermediate 49 was converted to the 5'-deoxy-5'-phosphonate ester 50. The 3'-acetyl was removed and the resulting intermediate was converted to the mesylate 51. The treatment of 51 with sodium azide at elevated temperature gave the 3'-azido derivative 52. After removal of the ethyl groups, the tributylammonium salt of the phosphonate 53 was treated with carbonyldiimidazole, and the resulting intermediate 54 was condensed with the tributylammonium salt of difluoromethylenediphosphonate to yield 3'-azido-3',5'-dideoxythymidine 5'-β,γ-(difluoromethylene)triphosphate 55. Compounds 56 and 57 were prepared through similar procedures.

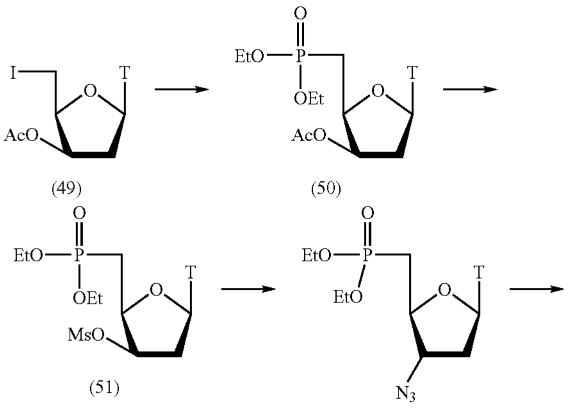

(49) (50) (51) (52)

-continued

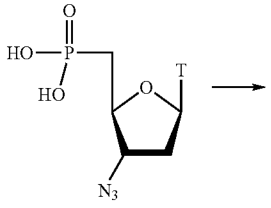

(53)

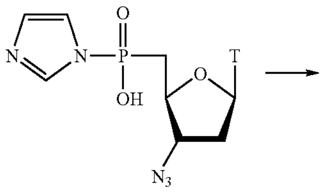

(54)

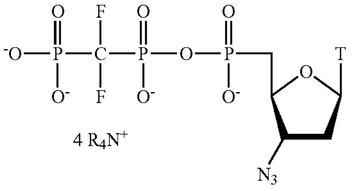

(55)

(56)

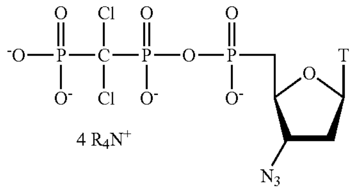

(57)

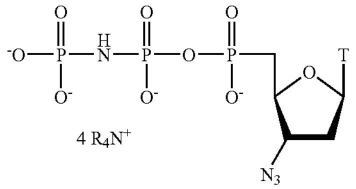

The scheme below shows the synthesis of 3',5'-dideoxy-5'-difluoromethylenethymidine 5'-β,γ-(difluoromethylene) triphosphate (62). 2,3-Dideoxy-1-O-methylribofuranose was converted to the 5-O-triflate 58, which was treated with LDA and then reacted with diethyl P-difluoromethylphosphonate to give the 5-deoxy-5-difluoromethylene derivative 59. The condensation of 59 with a silylated thymine in the presence of tin chloride gave the nucleoside 5'-phosphonate ester 60. After removal of the ethyl groups with TMSBr, the triethylammonium salt of the nucleoside 5'-phosphonate 61 was treated with carbonyldiimidazole, and then condensed with the tributylammonium salts of difluoromethylene-diphosphonate to give 3',5'-dideoxy-5'-difluoromethylen-ethymidine 5'-β,γ-(difluoromethylene)triphosphate (62). Compounds 63 and 64 were prepared through similar procedures.

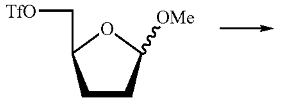

(58)

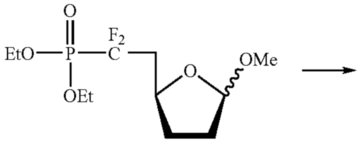

(59)

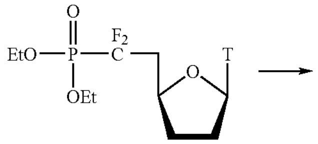

(60)

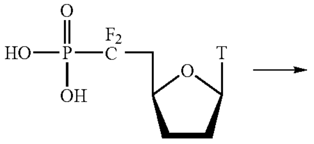

(61)

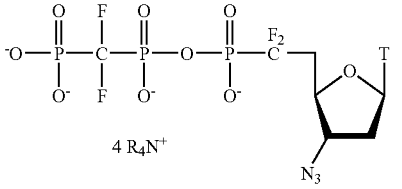

(62)

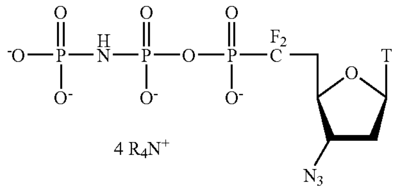

(63)

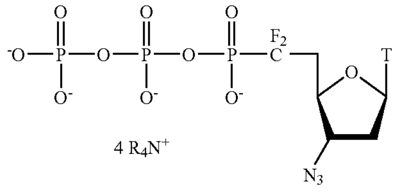

(64)

Another general approach for the preparation of α-P-substituted nucleoside triphosphates can be used for the preparation of the nucleotide mimics of the present invention, involving the reaction of an activated nucleoside monophosphonate with pyrophosphate or diphosphate mimics. The activation is usually achieved by attaching an imidazole or a morpholino group to the phosphate, as shown by the example given below. 3'-Azido-3'-deoxythymidine is converted to its 5'-phosphonate 65 (R=alkyl or aryl), which can be activated by treatment with carbonyldiimidazole. The resulting intermediate 66 is condensed with the tetrabutylammonium salt of difluoromethylenediphosphonate to give 3'-azido-3'-deoxythymidine 5'-α-P-substituted β,γ-(difluoromethylene)triphosphate (67).

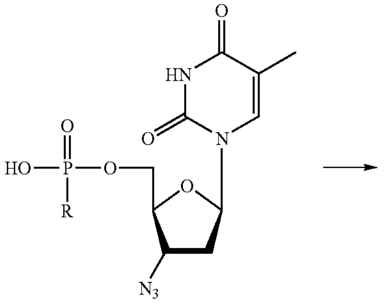

(65)

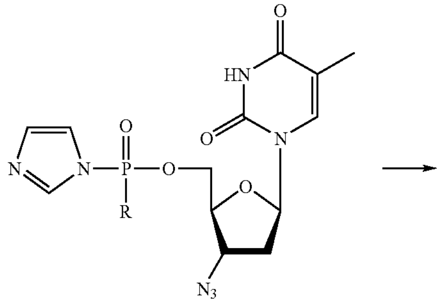

(66)

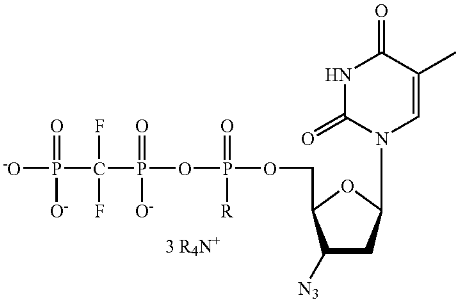

(67)

Nucleotide Mimic Prodrugs

The prodrug approach is one of the efficient methods to deliver polar, negatively-charged nucleotide mimics into cells. A number of prodrug approaches for nucleoside 5'-monophosphates have been developed and potentially can be applied to the nucleotide mimics of the present invention. The nucleotide mimic prodrugs may include, but are not limited to, alkyl phosphate esters, aryl phosphate ester, acylthioethyl phosphate esters, acyloxymethyl phosphate esters, 1,2-O-diacylglyceryl phosphate esters, 1,2-O-dialkylglyceryl phosphate esters, and phosphoramidate esters. These masking groups were also successfully attached to the nucleoside mimics of the present invention. The resulting compounds can serve as the prodrugs of the nucleotide mimics.

One of the straightforward methods for the preparation of nucleotide mimic prodrugs is the reaction of the nucleotide mimics with a masking reagent bearing a leaving group. For example, the nucleoside 5'-imidodiphosphate 8 is treated with tributylstannyl methoxide to convert the diphosphate 8 to a stannic salt, which was reacted with pivaloxymethyl iodide to give compound 68. The pivaloxymethyl group (POM) can be cleaved by a variety of cellular esterases. In cells compound 68 can be converted to compound 8. Compound 69 was prepared from the reaction of the corresponding triphosphate 27 with pivaloxymethyl iodide through a similar procedure. Compound 70 was also prepared through this type of reaction, but the reagent is S-pivaloyl-2-thioethyl (SATE) p-nitrobenzenesulfonate. S-Pivaloyl-2-thioethyl and pivaloxymethyl as the making groups of phosphate have been intensively studied and usually abbreviated as SATE and POM, respectively. Like POM, SATE can also be readily cleaved by cellular esterases.

(68)

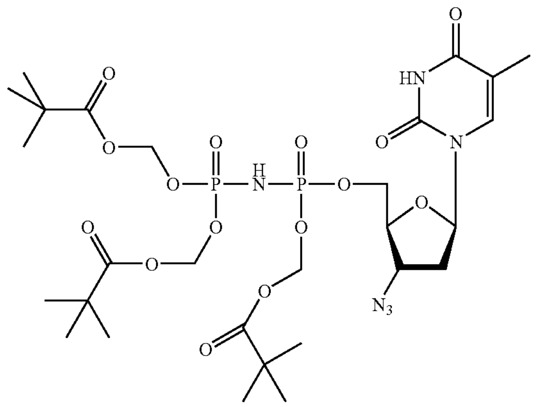

(69)

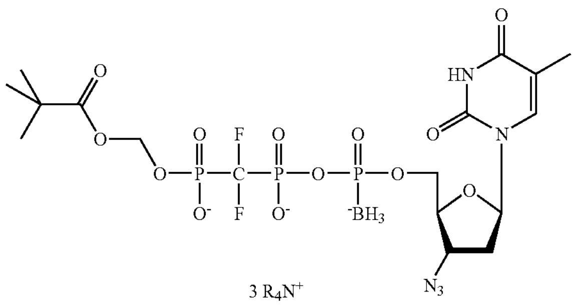

(70)

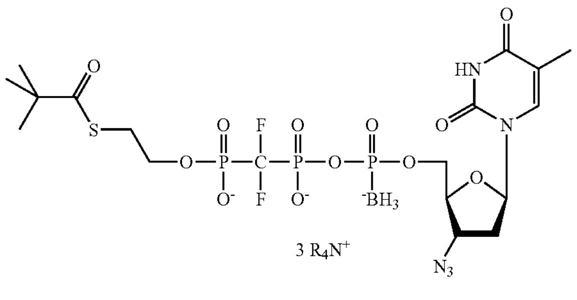

Another approach for the preparation of the prodrugs from nucleotide mimics is the condensation of nucleotide mimics with a masking group bearing a hydroxyl group. For example, compound 8 was treated with 1-(mesitylene-2-sulfonyl)-3-nitro-1,2,4-triazole and then reacted with S-pivaloxy-2-thioethanol to give compounds 71 and 72, which were separated by chromatography.

(71)

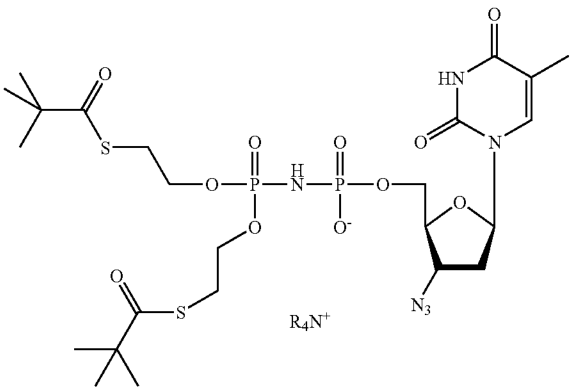

(72)

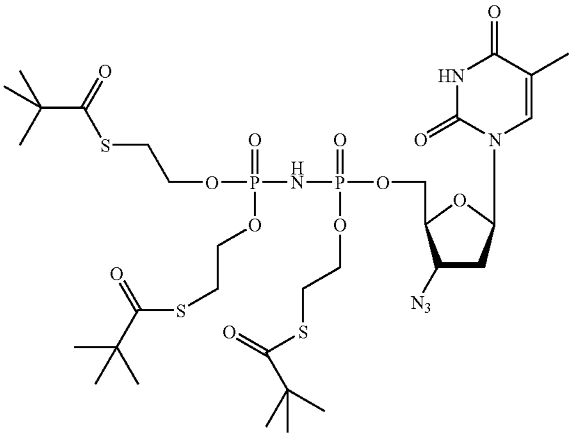

Alternatively, the prodrugs of certain nucleotide mimics can be prepared from nucleosides. For example, 2'-deoxy-2',2'-difluorocytidine 73 was converted to the β-O-(S-pivaloyl-2-thioethyl)-, di-O-(S-pivaloyl-2-thioethyl)- and tri-O-(S-pivaloyl-2-thioethoxy)methylenediphosphonate 75-77 in a one-pot reaction. The nucleoside 73 was first reacted with methylenediphosphonotetrachloridate to yield the trichloro intermediate 74, which was then treated with excess S-pivaloyl-2-thioethanol. The resulting three S-pivaloyl-2-thioethyl derivatives 75-77 were separated on a reverse-phase HPLC.

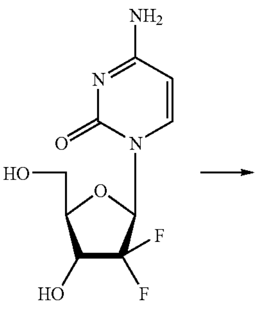

(73)

-continued

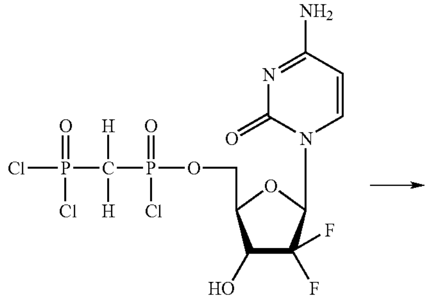

(74)

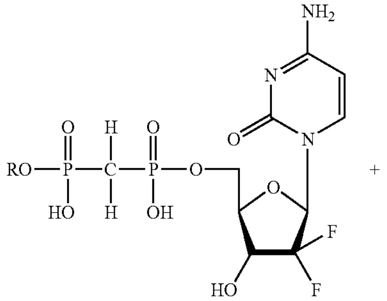

(75)

-continued

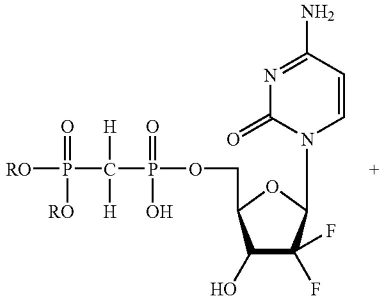

(76)

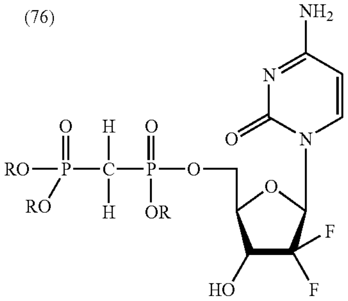

(77)

R =

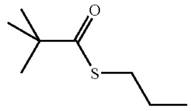

Another type of prodrugs of the nucleoside mimics is lipid-masked nucleotide mimics, in which a lipid is attached to the terminal phosphorus of a nucleotide mimic directly or through a biologically-cleavable linker. For example, compound 79 was prepared through the condensation of the nucleoside triphosphate mimic 27 with the lipid reagent 78, which was synthesized from the 1,2-O-dipalmitoylglycerol.

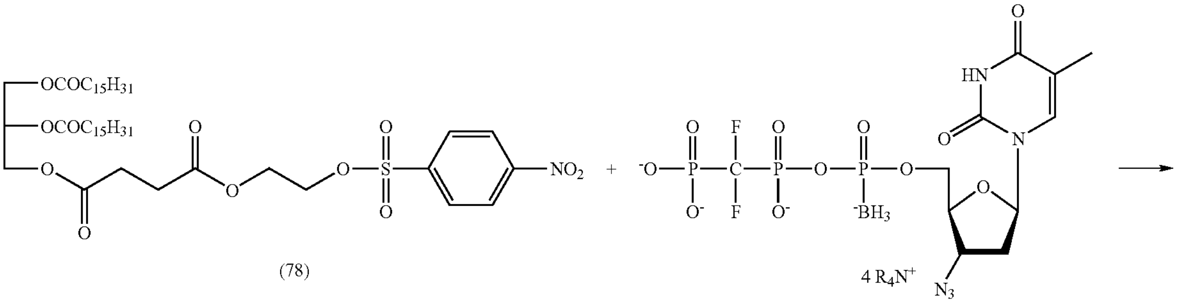

(78)

(27)

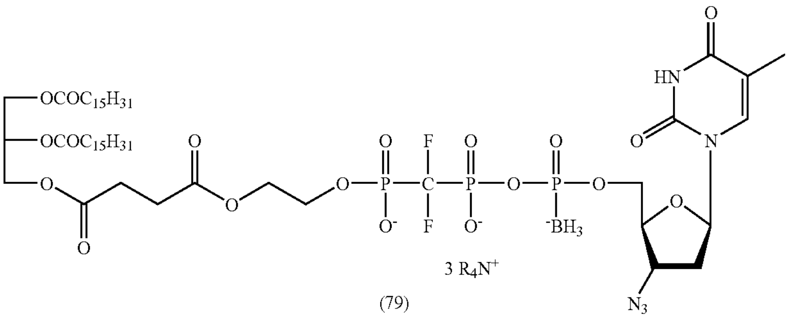

(79)

C. Biological Applications and Administration

The nucleoside diphosphate mimics and nucleoside triphosphate mimics of the present invention may be useful for the inhibition of a variety of enzymes including, but not limited to, DNA or RNA polymerases, helicases, ribonucleotide reductases, protein kinases, and telomerases and for the modulation of G-proteins, P2 purinergic receptors and the allosteric sites of a variety of enzymes.

The nucleotide mimics of the present invention are useful as human therapeutics for the treatment of infectious diseases caused by viruses including, but not limited to, HIV, HBV, HCV, HDV, HSV, HCMV, small pox, West Nile virus, influenza viruses, measles, rhinovirus, RSV. VZV, EBV, vaccinia virus, and papilloma virus.

The nucleoside diphosphate mimics and nucleoside triphosphate mimics of the present invention are useful for the treatment of infectious diseases caused by bacteria and fungi.

Those nucleotide mimics that have potent cytotoxicities to fast-dividing cancerous cells are useful for the treatment of proliferative disorders, including, but not limited to, lung cancer, liver cancer, prostate cancer, colon cancer, breast cancer, ovarian cancer, melanoma, and leukemia.

As the ligands of P2 receptors and G-proteins as well as the inhibitors of protein kinases, the nucleostide mimics of the present invention are useful for the treatment of a wide range of other diseases and disorders such as inflammatory diseases, autoimmune diseases, Type 2 diabetes, and cardiovascular diseases.

In order to overcome drug resistance, combination therapies are widely used in the treatment of infectious diseases and proliferative disorders. The nucleotide mimics or their prodrugs of the present invention may be therapeutically administered as a single drug, or alternatively may be administered in combination with one or more other active chemical entities to form a combination therapy. The other active chemical entities may be a small molecule, a polypeptide, or a polynucleotide.

The pharmaceutical composition of the present invention comprises at least one of the compounds represented by Formula (I) and (XVI) or pharmaceutically acceptable salts, esters or prodrugs thereof as active ingredients. The compositions include those suitable for oral, topical, intravenous, subcutaneous, nasal, ocular, pulmonary, and rectal administration. The compounds of the invention can be administered to mammalian individuals, including humans, as therapeutic agents.

For example, the compounds of the invention are useful as antiviral agents. The present invention provides a method for the treatment of a patient afflicted with a viral infection comprising administering to the patient a therapeutically effective antiviral amount of a compound of the invention. The term “viral infection” as used herein refers to an abnormal state or condition characterized by viral transformation of cells, viral replication and proliferation. Viral infections for which treatment with a compound of the invention will be particularly useful include the viruses mentioned above.

A “therapeutically effective amount” of a compound of the invention refers to an amount which is effective, upon single or multiple dose administration to the patient, in controlling the growth of e.g., the microbe or tumor or in prolonging the survivability of the patient beyond that expected in the absence of such treatment. As used herein, “controlling the growth” refers to slowing, interrupting, arresting or stopping the microbial or proliferative transformation of cells or the replication and proliferation of the microbe and does not necessarily indicate a total elimination of e.g., the microbe or tumor.

Accordingly, the present invention includes pharmaceutical compositions comprising, as an active ingredient, at least one of the compounds of the invention in association with a pharmaceutical carrier. The compounds of this invention can be administered by oral, parenteral (intramuscular, intraperitoneal, intravenous (IV) or subcutaneous injection), topical, transdermal (either passively or using iontophoresis or electroporation), transmucosal (e.g., nasal, vaginal, rectal, or sublingual) or pulmonary (e.g., via dry powder inhalation) routes of administration or using bioerodible inserts and can be formulated in dosage forms appropriate for each route of administration.

Solid dosage forms for oral administration include capsules, tablets, pills, powders, and granules. In such solid dosage forms, the active compound is admixed with at least one inert pharmaceutically acceptable carrier such as sucrose, lactose, or starch. Such dosage forms can also comprise, as is normal practice, additional substances other than inert diluents, e.g., lubricating, agents such as magnesium stearate. In the case of capsules, tablets, and pills, the dosage forms may also comprise buffering agents. Tablets and pills can additionally be prepared with enteric coatings.

Liquid dosage forms for oral administration include pharmaceutically acceptable emulsions, solutions, suspensions, syrups, with the elixirs containing inert diluents commonly used in the art, such as water. Besides such inert diluents, compositions can also include adjuvants, such as wetting agents, emulsifying and suspending agents, and sweetening, flavoring, and perfuming agents.

Preparations according to this invention for parenteral administration include sterile aqueous or non-aqueous solutions, suspensions, or emulsions. Examples of non-aqueous solvents or vehicles are propylene glycol polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria retaining filter, by incorporating sterilizing agents into the compositions, by irradiating the compositions, or by heating the compositions. They can also be manufactured using sterile water, or some other sterile injectable medium, immediately before use.

Compositions for rectal or vaginal administration are preferably suppositories which may contain, in addition to the active substance, excipients such as cocoa butter or a suppository wax. Compositions for nasal or sublingual administration are also prepared with standard excipients well known in the art.

Topical formulations will generally comprise ointments, creams, lotions, gels or solutions. Ointments will contain a conventional ointment base selected from the four recognized classes: oleaginous bases; emulsifiable bases; emulsion bases; and water-soluble bases. Lotions are preparations to be applied to the skin or mucosal surface without friction, and are typically liquid or semiliquid preparations in which solid particles, including the active agent, are present in a water or alcohol base. Lotions are usually suspensions of solids, and preferably, for the present purpose, comprise a liquid oily emulsion of the oil-in-water type. Creams, as known in the art, are viscous liquid or semisolid emulsions, either oil-in-water or water-in-oil. Topical formulations may also be in the form of a gel, i.e., a semisolid, suspension-type system, or in the form of a solution.

Finally, formulations of these drugs in dry powder form for delivery by a dry powder inhaler offer yet another means of administration. This overcomes many of the disadvantages of the oral and intravenous routes.

The dosage of active ingredient in the compositions of this invention may be varied; however, it is necessary that the amount of the active ingredient shall be such that a suitable dosage form is obtained. The selected dosage depends upon the desired therapeutic effect, on the route of administration, and on the duration of the treatment desired. Generally, dosage levels of between 0.001 to 10 mg/kg of body weight daily are administered to mammals.

The following examples are put forth so as to provide those of ordinary skill in the art with a complete disclosure and description of how to prepare and use the compounds disclosed and claimed herein.

EXAMPLES

A. Chemical Synthesis

The following examples for the preparation of the nucleotide mimics of the present invention are given in this section. The examples herein are not intended to limit the scope of the present invention in any way. The nucleotide mimics of the present invention can be prepared by those skilled in the art of nucleoside and nucleotide chemistry. The nucleotide mimics of the present invention exist as the salts of nucleotide mimics. However, the amounts of the products given below in the examples are based on UV absorptions and calculated from the molecular weights of H-forms of nucleotide mimics.

Example 1

2'-Deoxy-(E)-2'-fluoromethylenecytidine 5'-imido-diphosphate (3)

Trichloro[(dichlorophosphoryl)imido]phosphorane (83 mg, 0.39 mmol) was added to 2'-deoxy-(E)-2'-fluoromethylenecytidine (50 mg, 0.19 mmol) in anhydrous trimethyl phosphate (3 mL) at −15° C. under an argon atmosphere. After stirring for 2 h the reaction mixture was poured into ice-cold triethylammonium bicarbonate (TEAB) solution (pH 7.0, 1.0 M, 5 mL) and stirred for 30 minutes. Purification by HPLC gave 9.0 mg of the titled compound 3.

Example 2

2'-Deoxy-(E)-2'-fluoromethylenecytidine 5'-methylenediphosphonate (4)

Methanephosphonic dichloride (98 mg, 0.39 mmol) was added to 2'-deoxy-(E)-2'-fluoromethylenecytidine (50 mg, 0.19 mmol) in anhydrous trimethyl phosphate (3 mL) at −15° C. under an argon atmosphere. After stirring for 2 h the reaction mixture was poured into an ice-cold TEAB solution (1.0 M, 5 mL) and stirred for 30 minutes. Purification by HPLC gave 8.6 mg of the titled compound 4.

Example 3

2'-Deoxy-2',2'-difluorocytidine-5'-methylenediphosphonate (5)

2'-Deoxy-2',2'-difluorocytidine (0.2 g, 0.76 mmol) was dissolved in anhydrous trimethyl phosphate (2 mL) and stirred with molecular sieves under an argon atmosphere for 16 h. The mixture was cooled to −20° C. under an argon atmosphere and methylenebis(phosphonic dichloride) (380 mg, 1.52 mmol) was added. After stirring for 1 h the mixture was quenched using ice-cold TEAB solution (1.0 M, 10 mL) and stirred for 30 minutes. Purification by HPLC gave 28.9 mg of the titled compound.

Example 4

2'-Deoxy-2',2'-difluorocytidine 5'-imidodiphosphate (6)

2'-Deoxy-2',2'-difluorocytidine (0.2 g, 0.76 mmol) was dissolved in anhydrous trimethyl phosphate (5 mL) and stirred with molecular sieves under an argon atmosphere for 16 h. The mixture was cooled to −20° C. under an argon atmosphere and treated with trichloro-[(dichlorophosphoryl)imido]phosphorane (408 mg, 1.52 mmol). After stirring for 1 h the mixture was quenched with ice-cold TEAB solution (1.0 M, 10 mL) and stirred for 30 minutes. Purification by HPLC gave 57.0 mg of the titled compound.

Example 5

2'-Deoxy-2',2'-difluorocytidine 5'-(difluoromethylene)diphosphonate (7)

Step 1. Tetraisopropyl difluoromethylenediphosphonate (2.1 g, 5.51 mmol) was dissolved in methylene dichloride (20 mL) and treated with trimethylsilyl bromide (3.6 mL, 27.6 mmol). The mixture was heated at reflux for 16 h under an argon atmosphere, cooled and then evaporated in vacuo. The residue was coevaporated with carbon tetrachloride (20 mL), resuspended in carbon tetrachloride (20 mL) and added to phosphorus pentachloride (2.9 g, 13.2 mmol). After stirring for 16 h at room temperature under an argon atmosphere difluoromethylenebis(diphosphonic dichloride) was isolated by vacuum distillation (65° C., 0.5 mmHg) and used directly in the next step.

Step 2. 2'-Deoxy-2',2'-difluorocytidine (276 mg, 1.05 mmol) was dissolved in anhydrous trimethyl phosphate (5 mL) and stirred with molecular sieves under an argon atmosphere for 16 h. The mixture was added to difluoromethylenebis(phosphonic dichloride) (300 mg, 1 mmol) from Step 1 at −40° C. under an argon atmosphere. Stirring continued for 2 h, then the reaction mixture was poured into ice-cold TEAB solution (1.0 M, 5 mL) and stirred for 30 minutes. The aqueous portion was purified by HPLC to give 41.8 mg of the titled compound.

Example 6

3'-Deoxy-3'-azidothymidine 5'-(difluoromethylene) diphosphonate (10)

To a flask containing difluoromethylenediphosphononic acid tri(tetrabutylamomonium) salt (3.855 g, 4.12 mmol) under argon was added a solution of 3'-azido-3'-deoxy-5'-O-tosylthymidine (358 mg, 0.85 mmol) in acetonitrile (2.5 mL). The resulting solution was stirred at room temperature for 27 hours, quenched with water (10 mL), and stirred for 5 min. Purification by HPLC gave 160 mg of the titled compound 10.

Example 7

3'-Azido-3'-deoxythymidine 5'-α-P-borano-β-P-methyldiphosphate (13)

To a stirred solution of 3'-azido-3'-deoxythymidine (67 mg. 0.25 mmol) in anhydrous DMF (1 mL) at 0° C. under argon were added tributylamine (77 μL, 0.325 mmol) and then bis(diisopropylamino)chlorophosphine (74 mg, 0.275 mmol) in DMF (06 mL) and THF (0.3 mL). The reaction mixture was stirred at 0° C. for 3 h and cooled with ice. A solution of tributylamine (0.24 mL, 1.0 mmol) and methyphosphonic acid (72 mg, 0.75 mmol) in DMF (1 mL) was added, and the resulting solution was stirred at room temperature overnight. Borane-diisopropylethylamine complex (1.0 mL) was added and the resulting mixture was stirred for 7 h. The reaction mixture was cooled with ice and quenched by slow addition of water (2 mL). The mixture was stirred at room temperature overnight, diluted with water (3 mL). Purification by HPLC gave 7.7 mg of the titled compound 13.

Example 8

3'-Azido-3'-deoxythymidine 5'-α-P-borano-β,γ-(difluoromethylene)triphosphate (27)

Step A. The Preparation of Tetraisopropyl Difluoromethylenediphosphonate

To a stirred solution of tetraisopropyl difluoromethylenediphosphonate (4.5 g, 13.07 mmol) in anhydrous THF (20 mL) at −78° C. under argon were added sodium bis(trimethylsilyl)amide (1.0 M in THF, 28.7 mL) and N-fluorobenzenesulfonimide (9.89 g, 31.36 mmol). The reaction mixture was stirred at −78° C. for 1 h, quenched with saturated aqueous ammonium chloride (20 mL), warmed to room temperature, diluted with ether, washed with 10% aqueous sodium bicarbonate and then with brine, dried over sodium sulfate, and concentrated. Chromatography on silica gel with 5-30% ethyl acetate in hexanes gave 2.18 g of tetraisopropyl difluoromethylenediphosphonate and 0.32 g of tetraisopropyl monofluoromethylenediphosphonate.

Step B. The Preparation of difluoromethylenediphosphonic acid bis(tributylammunium) salts To a stirred solution of tetraisopropyl difluoromethylenediphosphonate (2.0 g, 5.26 mmol) in anhydrous acetonitrile (30 mL) was added dropwise trimethylsilyl bromide (4.17 mL, 31.58 mmol). The resulting solution was stirred at 40-42° C. for 24 h, concentrated to dryness, and coevaporated with anhydrous acetonitrile once. The residue was re-dissolved in an acetonitrile/water mixture, and then coevaporated with DMF. The residue was dissolved in a DMF solution of tributylamine (1.93 g, 2.48 mL, 10.43 mmol), transferred into multiple small flasks, concentrated to dryness, and coevaporated with anhydrous DMF three times. The residue was dried in a vacuum oven at 40° C. for 4 h to give a slightly yellow residue (3.35 g).

Step C. The Preparation of 3'-azido-3'-deoxythymidine α-P-borano-β,γ-(difluoromethylene)triphosphate (27)

To a stirred solution of 3'-azido-3'-deoxythymidine (800 mg, 3.0 mmol) in anhydrous DMF (6 mL) and pyridine (1.5 mL) at 0° C. under argon was added a solution of 2-chloro-4H-1,3,2-benzodioxaphosphorin-4-one (728 mg, 3.6 mmol) in DMF (3 mL). The reaction mixture was stirred at room temperature for 1 h and cooled with ice. Tributylamine (1.8 mL, 16.5 mmol) was added, followed by addition of difluoromethylenediphosphonic acid bis(tributylammunium) salt (2.28 g, 3.9 mmol) in DMF (6 mL). The reaction mixture was stirred at room temperature for 1 h and cooled with ice. Borane-diisopropylethylamine complex (12 mL) was added and the resulting mixture was stirred at room temperature overnight. The reaction mixture was cooled with ice and quenched by slow addition of water (30 mL). The mixture was stirred at room temperature for 2 h, diluted with water (30 mL), and extracted with chloroform three times. The aqueous solution was loaded on a reverse-phase (C18) HPLC and eluted with TEAA buffer (pH 7.0), and the purified product was desalted by repeated lyophilization. 3'-azido-3'-deoxythymidine α-P-borano-β,γ-(difluoromethylene)triphosphate (501 mg, triethylammonium salts, a mixture of two diastereomers) was obtained as a white foam.

The two diastereoisomers (α—Rp and α-Sp) were separated under the same HPLC conditions to give pure 3'-azido-3'-deoxythymidine α-(R)-P-borano-β,γ-(difluoromethylene) triphosphate (the one having shorter retention time is designated as isomer 1, the other as isomer 2) and 3'-azido-3'-deoxythymidine α-(S)-P-borano-β,γ-(difluoromethylene) triphosphate.

Example 9

7-deaza-2'-C-methyladenosine 5'-α-P-borano-β,γ-(difluoromethylene)triphosphate (22)

Step A. The Preparation of 7-deaza-2'-C-methyl-2',3'-O—$N^6$-triacetyladenosine (18)

A solution of 2'-C-methyl-7-deazaadenosine (402 mg, 1.43 mmol) and chlorotrimethylsilane 9237 mg, 1.57 mmol) in anhydrous pyridine (7 mL) was stirred at room temperature overnight. Acetic anhydride (1.08 mL, 11.44 mmol) was added, and the resulting mixture was stirred at room temperature for 3 h. Then DMAP (700 mg, 5.72 mmol) and triethylamine (0.78 mL, 5.72 mmol) were added, and the resulting mixture was heated at 45-50° C. overnight. The mixture was cooled, diluted with ethyl acetate, washed with water (2×), with 2N HCl, then with water (2×), then with 10% $NaHCO_3$, dried over sodium sulfate, and concentrated. Chromatography on silica gel with ethyl aceate yielded 7-deaza-2'-C-methyl-5'-O-trimethylsilyl-2',3'-O—$N^6$-triacetyladenosine as a white solid.

The white solid was dissolved in THF (5 mL) and TBAF in THF (1.0 M, 1.5 mL) was added. The resulting solution stood at room temperature for 2 h and concentrated. Chromatography on silica gel with 5% methanol in methylene chloride gave 211 mg of 7-deaza-2'-C-methyl-2',3'-O—$N^6$-triacetyladenosine as a white solid.

Step B. The Preparation of 7-deaza-2'-C-methyladenosine 5'-α-P-borano-β,γ-(difluoromethylene)triphosphate (22)

To a stirred solution of 7-deaza-2'-C-methyl-2',3'-O—$N^6$-triacetyladenosine (62 mg. 0.15 mmol) in anhydrous DMF (0.5 mL) and pyridine (0.1 mL) at 0° C. under argon was added a solution of 2-chloro-4H-1,3,2-benzodioxaphosphorin-4-one (39 mg, 0.195 mmol). The reaction mixture was stirred at room temperature for 1 h and cooled with ice.

Tributylamine (0.1 mL) was added, followed by addition of difluoromethylenediphosphonic acid bis(tributylammunium) salt (140 mg, 0.24 mmol) in DMF (0.4 mL). The reaction mixture was stirred at room temperature for 1 h and cooled with ice. Borane diisopropylethylamine complex (0.6 mL) was added and the resulting mixture was stirred at room temperature for 6 h, cooled with ice and quenched by slow addition of water (1.5 mL). The mixture was stirred at room temperature for 1 h, diluted with water (5 mL), extracted with chloroform three times, and concentrated to about 2 mL. Aqueous ammonia (30%, 3 mL) was added and the resulting solution stood at room temperature overnight. Ammonia was evaporated and the remaining aqueous solution was loaded on a reverse-phase (C18) HPLC using TEAA buffer (pH 7.0) to yield the titled compound 22, the isomer 1: 1.37 mg and the isomer 2: 1.98 mg.

Example 10

3'-Azido-3'-deoxythymidine 5'-α-P-borano-β,γ-imidotriphosphate (23)

To a stirred solution of 3'-azido-3'-deoxythymidine (134 mg. 0.50 mmol) in anhydrous DMF (1 mL) and pyridine (0.25 mL) at 0° C. under argon was added a solution of 2-chloro-4H-1,3,2-benzodioxaphosphorin-4-one (101 mg, 0.50 mmol) in DMF. The reaction mixture was stirred at room temperature for 1 h and cooled with ice. Tributylamine (0.3 mL) was added, followed by addition of a solution of methylenediphosphonic acid (88 mg, 0.50 mmol) and tributylamine (0.3 mL) in DMF (0.5 mL). The reaction mixture was stirred at room temperature for 1 h and cooled with ice. Borane diisopropylethylamine complex (2.0 mL) was added and the resulting mixture was stirred at room temperature for 6 h, cooled with ice and quenched by slow addition of water (5 mL), and stirred at room temperature for 3 h. The crude was purified on a reverse-phase (C18) HPLC using TEAA buffer (pH 7.0) gave 60.3 mg of the titled compound 23 as a mixture of two diastereoisomers.

Example 11

3'-Azido-3'-deoxythymidine 5'-α-P-borano-β,γ-methylenetriphosphate (24)

3'-Azido-3'-deoxythymidine (134 mg, 0.5 mmol) was dissolved in 1 mL of anhydrous DMF in a 10 mL flask kept under argon. To this solution was added 0.25 mL of anhydrous pyridine. A freshly prepared solution of 2-chloro-4H-1,3,2-benzodioxaphosphorin-4-one (101 mg, 0.495 mmol) in anhydrous DMF (0.5 mL) was added via syringe. After 1 hour of stirring at room temperature, tributylamine (0.3 mL) was added followed by a mixture of methylenediphosphonic acid (88 mg, 0.495 mmol) and 3 eq. tributylamine in 0.5 mL of anhydrous DMF. The mixture was stirred for 1 hour and 2 mL of borane-diisopropylethylamine complex was added. After 6 hours stirring at room temperature 5 mL of deionized water was added and stirred at room temperature for 3 hour. Purification by HPLC yielded 46 mg of the titled compound 24.

Example 12

3'-Azido-3'-deoxythymidine 5'-α-P-borano-β,γ-(fluoromethylene)triphosphate (25)

Step A. The Preparation of fluoromethylenediphosphonic acid bis(tributylammunium) salts To a stirred solution of tetraisopropyl fluoromethylenediphosphonate (320 mg, 0.88 mmol) in 1,2-dichloroethane (5 mL) was added dropwise trimethylsilyl bromide (0.70 mL, 5.28 mmol). The resulting solution was stirred at 40-42° C. for 24 h and 3 mL of anhydrous toluene was added. The mixture was concentrated to dryness, and coevaporated with toluene once. The residue was redissolved in DMF (3 mL)/water (2 mL) mixture and concentrated. The residue was mixed with DMF (2 mL) and tributylamine (0.42 mL, 1.76 mmol) and then concentrated to dryness. The residue was coevaporated with anhydrous DMF two times. The resulting residue was dried in a vacuum oven at 30° C. overnight to give a slightly yellow residue (460 mg).

Step B. The Preparation of 3'-azido-3'-deoxythymidine α-P-borano-β,γ-(fluoromethylene)triphosphate (25)

To a stirred solution of 3'-azido-3'-deoxythymidine (78 mg. 0.29 mmol) in anhydrous DMF (1 mL) and pyridine (0.2 mL) at 0° C. under argon was added a solution of 2-chloro-4H-1,3,2-benzodioxaphosphorin-4-one (77 mg, 0.38 mmol). The reaction mixture was stirred at room temperature for 1 h and cooled with ice. Tributylamine (0.18 mL) was added, followed by addition of fluoromethylenediphosphonic acid bis(tributylammonium) salts (250 mg, 0.43 mmol) in DMF (0.6 mL). The reaction mixture was stirred at room temperature for 1 h and cooled with ice. Borane diisopropylethylamine complex (1.20 mL) was added and the resulting mixture was stirred at room temperature for 6 h, cooled with ice and quenched by slow addition of water (3 mL). The mixture was stirred at room temperature overnight, diluted with water (10 mL), and extracted with chloroform three times.

The separation of the four α-P-borano diastereoisomers of the titled compound 25 on a reverse-phase (C18) HPLC using TEAA buffer (pH 7.0) was conducted to give the isomer 1: 3.75 mg; the isomer 2 (containing other isomers): 8.24 mg; the isomer 3 (containing other isomers): 5.76 mg; the isomer 4: 2.55 mg.

Example 13

3'-Azido-3'-deoxythymidine 5'-α-P-borano-β,γ-(dichloromethylene)triphosphate (26)

Step A. The Preparation of dichloromethylenediphosphonic acid bis(tributylammunium) salt An aqueous solution of dichloromethylenediphosphonic acid disodium salt (1.0 g, 3.46 mmol) was loaded on a column of DOWEX 50WX8-100 ion-exchange resin and eluted with water. Tributylamine (1.65 mL, 6.92 mmol) was added and the mixture was shaken vigorously. The resulting solution was concentrated to dryness and coevaporated with anhydrous DMF three times. The residue was dried under vacuum overnight.

Step B. The Preparation of 3'-azido-3'-deoxythymidine α-P-borano-β,γ-(dichloromethylene)triphosphate (26)

To a stirred solution of 3'-azido-3'-deoxythymidine (89 mg. 0.33 mmol) in anhydrous DMF (1 mL) and pyridine (0.2 mL) at 0° C. under argon was added a solution of 2-chloro-4H-1,3,2-benzodioxaphosphorin-4-one (83 mg, 0.41 mmol). The reaction mixture was stirred at room temperature for 1 h and cooled with ice. Tributylamine (0.2 mL) was added, followed by addition of dichloromethylenediphosphonic acid bis(tributylammunium) salt (430 mg, 0.43 mmol) in DMF (1 mL). The reaction mixture was stirred at room temperature for 1 h and cooled with ice. Borane diisopropylethylamine complex (1.32 mL) was added and the resulting mixture was stirred at room temperature for 6 h, cooled with ice and quenched by slow addition of water (3 mL). The mixture was stirred at room temperature overnight, diluted with water (10 mL), and extracted with chloroform three times. The two α-P-borano diastereoisomers were separated on a reverse-phase (C18) HPLC using TEAA buffer (pH 7.0), and the purified products were desalted by repeated lyophilization to give the titled compound 26; the isomer 1: 8.3 mg and the isomer 2: 11.3 mg.

Example 14

3'-Deoxythymidine 5'-α-P-borano-β,γ-(difluoromethylene)triphosphate (28)

3'-Deoxythymidine (66.3 mg, 0.150 mmol) was dissolved in 0.5 mL of anhydrous DMF in a 10 mL round-bottom flask kept under argon. To this was added 0.1 mL of anhydrous pyridine. A freshly prepared, solution of 2-chloro-4H-1,3,2-benzodioxaphosphorin-4-one (36.4 mg, 0.180 mmol) in anhydrous DMF (0.5 mL) was added via syringe at 0° C. After stirring at room temperature for 1 hour, tributylamine (0.3 mL) was added followed by a solution of difluoromethylenediphosphonic acid bis(tri-n-butylammonium) salt (113.5 mg, 0.195 mmol) in anhydrous DMF (1 mL). The mixture was stirred at room temperature for 1 hour and borane-diisopropylethylamine complex (0.25 mL) was added at 0° C. After stirring at room temperature for 12 hour water (10 mL) was added and the mixture was stirred at room temperature for 30 minutes. Purification by HPLC yielded 4.8 mg of the titled compound 28.

Example 15

3'-Azido-3'-deoxythymidine 5'-α-P-thio-β,γ-(difluoromethylene)triphosphate (29)

3'-Azido-3'-deoxythymidine (103.8 mg, 0.388 mmol) was dissolved in 1 mL of anhydrous DMF in a 10 mL round-bottom flask kept under argon. To this was added 0.20 mL of anhydrous pyridine. A freshly prepared solution of 2-chloro-4H-1,3,2-benzodioxaphosphorin-4-one (101.2 mg, 0.495 mmol) in anhydrous DMF (1 mL) was added via syringe at 0° C. After stirring at room temperature for 1 hour, tributylamine (0.3 mL) was added followed by a solution of difluoromethylenediphosphonic bis(tri-n-butylammonium) salt (294 mg, 0.504 mmol) in anhydrous DMF (1 mL). The mixture was stirred at room temperature for 1 hour and sulfur (24.8 mg, 0.776 mmol) was added at 0° C. After stirring at room temperature for 2 hour distilled deionized water (10 mL) was added and the mixture was stirred at room temperature for 30 minutes. Purification by HPLC yielded 112.8 mg of the titled compound 29.

Example 16

3'-Deoxythymidine 5'-α-P-thio-β,γ-(difluoromethylene)triphosphate (30)

3'-Deoxythymidine (66.3 mg, 0.150 mmol) was dissolved in 0.5 mL of anhydrous DMF in a 10 mL round-bottom flask kept under argon. To this was added 0.1 mL of anhydrous pyridine. A freshly prepared solution of 2-chloro-4H-1,3,2-benzodioxaphosphorin-4-one (36.4 mg, 0.180 mmol) in anhydrous DMF (0.5 mL) was added via syringe at 0° C. After stirring at room temperature for 1 hour, tributylamine (0.3 mL) was added followed by a solution of difluoromethylenediphosphonic acid bis(tri-n-butylammonium) salt of (13.5 mg, 0.195 mmol) in anhydrous DMF (1 mL). The mixture was stirred at room temperature for 1 hour and sulfur (9.6 mg, 0.300 mmol) was added at 0° C. After stirring at room temperature for 2 hours, distilled deionized water (10 mL) was added and the mixture was stirred at room temperature for 30 minutes. Purification by HPLC yielded 29 mg of the titled compound 30.

Example 17

3'-Deoxythymidine 5'-α,α-P-dithio-β,γ-(difluoromethylene)triphosphate (31)

3'-Deoxythymidine (66.3 mg, 0.150 mmol) was dissolved in 0.5 mL of anhydrous DMF in a 10 mL round-bottom flask kept under argon. To this was added 0.1 mL of anhydrous pyridine. A freshly prepared solution of 2-chloro-4H-1,3,2-benzodioxaphosphorin-4-one (36.4 mg, 0.180 mmol) in anhydrous DMF (0.5 mL) was added via syringe at 0° C. After stirring at room temperature for 1 hour, tributylamine (0.3 mL) was added followed by a solution of difluoromethylenediphosphonic acid bis(tri-n-butylammonium) salt (113.5 mg, 0.195 mmol) in anhydrous DMF (1 mL). The mixture was stirred at room temperature for 1 hour and sulfur (9.6 mg, 0.300 mmol) was added at 0° C. After stirring at room temperature for 2 hours, lithium sulfide (137.8 mg, 3.0 mmol) was added. Stirring was continued for 12 hours. Distilled deionized water (10 mL) was added and the mixture was stirred at room temperature for 30 minutes. Purification by HPLC yielded 2.6 mg of the titled compound 31.

Example 18

3'-Deoxythymidine 5'-α-P-borano-α-P-thio-β,γ-(difluoromethylene)triphosphate (32)

3'-Deoxythymidine (42.0 mg, 0.186 mmol) was dissolved in 0.5 mL of anhydrous DMF in a 10 mL round-bottom flask kept under argon. To this was added 0.1 mL of anhydrous pyridine. A freshly prepared solution of 2-chloro-4H-1,3,2-benzodioxaphosphorin-4-one (45.1 mg, 0.223 mmol) in anhydrous DMF (0.5 mL) was added via syringe at 0° C. After stirring at room temperature for 1 hour, tributylamine (0.3 mL) was added followed by a solution of difluoromethylenediphosphonic acid bis(tri-n-butylammonium) salt (140.8 mg, 0.242 mmol) in anhydrous DMF (1 mL). The mixture was stirred at room temperature for 1 hour and borane-diisopropylethylamine complex (0.25 mL) was added at 0° C. After stirring at room temperature for 12 hour, lithium sulfide (17.09 mg, 0.372 mmol) was added. Stirring was continued for 1 hour. Distilled deionized water (10 mL)

was added and the mixture was stirred at room temperature for 30 minutes. Purification by HPLC yielded 4.2 mg of the titled compound 32.

Example 19

3'-Azido-3'-deoxythymidine 5'-α-P-ethylamino-β,γ-(difluoromethylene triphosphate (33)

3'-Azido-3'-deoxythymidine (133.6 mg, 0.495 mmol) was dissolved in 1 mL of anhydrous DMF in a 10 mL round-bottom flask kept under argon. To this was added 0.25 mL of anhydrous pyridine. A freshly prepared solution of 2-chloro-4H-1,3,2-benzodioxaphosphorin-4-one (101.2 mg, 0.495 mmol) in anhydrous DMF (0.5 mL) was added via syringe. After 1 hour of stirring at room temperature, tributylamine (0.3 mL) was added followed by a solution of difluoromethylenediphosphonic acid bis(tri-n-butylammonium) salt (294 mg, 0.5 mmol) in DMF (0.5 mL). The mixture was stirred for 1 hour and 253 mg (1 mmol) of iodine was added. After 3.5 hours stirring at room temperature 2 mL of a 2 M solution of ethylamine in THF was added and stirred at room temperature for 2 hours. Water (5 mL) was added and the mixture was stirred at room temperature overnight. Purification by HPLC yielded 54.2 mg of the titled compound 33.

Example 20

3'-Azido-3'-deoxythymidine 5'-α-P-phenylamino-β,γ-(difluoromethylene)triphosphate (34)

3'-Azido-3'-deoxythymidine (103.8 mg, 0.388 mmol) was dissolved in 1 mL of anhydrous DMF in a 10 mL round-bottom flask kept under argon. To this was added 0.20 mL of anhydrous pyridine. A freshly prepared solution of 2-chloro-4H-1,3,2-benzodioxaphosphorin-4-one (101.2 mg, 0.495 mmol) in anhydrous DMF (1 mL) was added via syringe at 0° C. After stirring at room temperature for 1 hour, tributylamine (0.3 mL) was added followed by a solution of difluoromethylenediphosphonic acid bis(tri-n-butylammonium) salt (294 mg, 0.504 mmol) in anhydrous DMF (1 mL). The mixture was stirred at room temperature for 1 hour and iodine (197.0 mg, 0.776 mmol) was added at 0° C. After stirring at room temperature for 1 hour, aniline (0.554 mL, 3.88 mmol) was added. Stirring was continued for 4 hours. Distilled deionized water (10 mL) was added and the mixture was stirred at room temperature for 30 minutes. Purification by HPLC yielded 16.2 mg of the titled compound 34.

Example 21

3'-Deoxythymidine 5'-α-P-fluoro-β,γ-(difluoromethylene)triphosphate (35)

3'-Deoxythymidine (47.0 mg, 0.208 mmol) was dissolved in 0.5 mL of anhydrous DMF in a 10 mL round-bottom flask kept under argon. To this was added 0.125 mL of anhydrous pyridine. A freshly prepared solution of 2-chloro-4H-1,3,2-benzodioxaphosphorin-4-one (50.6 mg, 0.250 mmol) in anhydrous DMF (0.5 mL) was added via syringe at 0° C. After stirring at room temperature for 1 hour, tributylamine (0.30 mL) was added followed by a solution of difluoromethylenediphosphonic acid bis(tri-n-butylammonium) salt (157.4 mg, 0.270 mmol) in anhydrous DMF (1 mL). The mixture was stirred at room temperature for 1 hour and iodine (105.6 mg, 0.416 mmol) was added at 0° C. After stirring at room temperature for 1 hour, potassium fluoride (120.8 mg, 2.08 mmol) was added. Stirring was continued for 2 hours. Water (10 mL) was added and the mixture was stirred at room temperature for 30 minutes. Purification bye HPLC yielded 47.3 mg of the titled compound 35.

Example 22

3'-Azido-3'-deoxythymidine 5'-α-P-azido-β,γ-(difluoromethylene)triphosphate (36)

3'-Azido-3'-deoxythymidine (40.09 mg, 0.150 mmol) was dissolved in 0.5 mL of anhydrous DMF in a 10 mL round-bottom flask kept under argon. To this was added 0.10 mL of anhydrous pyridine. A freshly prepared solution of 2-chloro-4H-1,3,2-benzodioxaphosphorin-4-one (33.4 mg, 0.165 mmol) in anhydrous DMF (0.5 mL) was added via syringe at 0° C. After stirring at room temperature for 1 hour, tributylamine (0.21 mL) was added followed by a solution of difluoromethylenediphosphonic acid bis(tri-n-butylammonium) salt (104.8 mg, 0.180 mmol) in anhydrous DMF (1 mL). The mixture was stirred at room temperature for 1 hour and iodine (76.1 mg, 0.300 mmol) was added at 0° C. After stirring at room temperature for 1 hour, sodium azide (97.5 mg, 1.50 mmol) was added. Stirring was continued for 2 hours. Distilled deionized water (10 mL) was added and the mixture was stirred at room temperature for 30 minutes. Purification by HPLC yielded 16.7 mg of the titled compound 36.

Example 23

3'-Azido-3'-deoxythymidine 5'-α-O-methyl-β,γ-(difluoromethylene)triphosphate (37)

3'-Azido-3'-deoxythymidine (40.09 mg, 0.150 mmol) was dissolved in 0.5 mL of anhydrous DMF in a 10 mL round-bottom flask kept under argon. To this was added 0.10 mL of anhydrous pyridine. A freshly prepared solution of 2-chloro-4H-1,3,2-benzodioxaphosphorin-4-one (33.4 mg, 0.165 mmol) in anhydrous DMF (0.5 mL) was added via syringe at 0° C. After stirring at room temperature for 1 hour, tributylamine (0.21 mL) was added followed by a solution of difluoromethylenediphosphonic acid bis(tri-n-butylammonium) salt (104.8 mg, 0.180 mmol) in anhydrous DMF (1 mL). The mixture was stirred at room temperature for 1 hour and iodine (76.1 mg, 0.300 mmol) was added at 0° C. After stirring at room temperature for 1 hour, sodium methoxide (0.343 mL, 1.50 mmol) was added. Stirring was continued for 30 minutes. Distilled deionized water (10 mL) was added and the mixture was stirred at room temperature for 30 minutes. Purification on by HPLC yielded 10.1 mg of the titled compound 37.

Example 24

3'-Deoxythymidine 5'-α-O-phenyl-β,γ-(difluoromethylene)triphosphate (38)

3'-Deoxythymidine (66.3 mg, 0.150 mmol) was dissolved in 0.5 mL of anhydrous DMF in a 10 mL round-bottom flask kept under argon. To this was added 0.1 mL of anhydrous pyridine. A freshly prepared solution of 2-chloro-4H-1,3,2-benzodioxaphosphorin-4-one (36.4 mg, 0.180 mmol) in anhydrous DMF (0.5 mL) was added via syringe at 0° C. After stirring at room temperature for 1 hour, tributylamine (0.3 mL) was added followed by a solution of difluoromethylenediphosphonic acid bis(tri-n-butylammonium) salt (113.5 mg, 0.195 mmol) in anhydrous DMF (1 mL). The mixture was stirred at room temperature for 1 hour and iodine (76.1 mg, 0.3 mmol) was added at 0° C. After stirring at room temperature for 2 hours, sodium phenoxide (87.1 mg, 0.750 mmol) was added. Stirring was continued for 12 hours. Distilled deionized water (10 mL) was added and the mixture was stirred at room temperature for 30 minutes. Purification by HPLC yielded 2.73 mg of the titled compound 38.

Example 25

3'-Azido-3'-deoxythymidine 5'-α-P-borano-β,γ-difluoromethylene-γ-O-methyltriphosphate (40)

A solution of the bis(tetrabutylammonium) salts of 3'-azido-3'-deoxythymidine 5'-α-P-borano-β,γ-(difluoromethylene)triphosphate (0.12 mmol), tributylamine (85 μL, 0.36 mmol) and methyl trifluoromethanesulfonate (54 μL, 0.48 mmol) in anhydrous acetonitrile (2 mL) stood at room temperature overnight. The reaction was quenched with water (2 mL) at 0° C. and then most of the acetonitrile was evaporated. The aqueous solution was subject to HPLC purification to give 1.51 mg of the titled compound 40.

Example 26

33'-Azido-3'-deoxythymidine 5'-α-P-borano-β,γ-difluoromethylene-γ-O-palmityltriphosphate (41)

Step A. Palmitol (1.0 g, 4.12 mmol) and DMAP (0.73 g, 5.9 mmol) in DCM (20 mL) was cooled to −20° C. under an argon atmosphere. p-Nitrobenzenesulfonyl chloride (1.09 g, 4.9 mmol) was added and the mixture was stirred at 5° C. under an argon atmosphere for 18 h. The reaction mixture was poured into cold sodium bicarbonate solution (saturated, 20 mL) and the organic layer was washed with citric acid (10%), brine, and dried over $MgSO_4$. The suspension was filtered, concentrated in vacuo and purified on silica gel flash column chromatography eluting with a gradient of 10-50% ether in hexane to give 1.06 g of palmityl 4-nitrobenzenesulfonate.

Step B. The bis(tetrabutylammonium) salts of 3'-azido-3'-deoxythymidine 5'-α-P-borano-β,γ-(difluoromethylene) triphosphate (183 mg, 0.146 mmol) was coevaporated with anhydrous DMF (3×5 mL). For the third coevaporation, approximately half the volume of DMF was removed and the mixture cooled to 0° C. under an argon atmosphere. Palmityl 4-nitrobenzenesulfonate (123 mg, 0.29 mmol) was added. After stirring for 1 h at room temperature the mixture was poured into ice-cold TEAB solution (1.0 M, 10 mL) and stirred for 30 minutes. The aqueous portion was purified on reverse-phase (C18) HPLC to give 6.8 mg of the titled compound 41.

Example 27

3'-Azido-3'-deoxythymidine 5'-α-P-borano-β,γ-difluoromethylene-γ-O-phenyltriphosphate (42)

Step A. A slurry of sodium hydride (320 mg, 8.0 mmol) in anhydrous DMF (10 mL) was treated with phenol (0.9 g, 10.0 mmol) dissolved in anhydrous DMF (2 mL) under an argon atmosphere. After stirring for 1 h at room temperature gas evolution had ceased. 15-Crown-5 (1.59 mL, 8.0 mmol) was added and stirring continued for 1 h. This mixture was used immediately in Step 2.

Step B. The triethylammonium salts of 3'-azido-3'-deoxythymidine 5'-α-P-borano-β,γ-(difluoromethylene)triphosphate (0.21 mmol) was coevaporated with anhydrous DMF (3×5 mL). For the third coevaporation, approximately half the volume of DMF was removed and anhydrous methanol (0.3 mL) was added, followed by N,N'-dicyclohexylcarbodiimide (200 mg). After stirring at room temperature under an argon atmosphere for 3 h, the mixture was concentrated in vacuo and the above procedure was repeated once more. After removing solvents in vacuo, the residue was resuspended in anhydrous DMF (3 mL) and treated dropwise with the phenoxide solution from Step 1. After stirring at room temperature under an argon atmosphere for 4 h the reaction mixture was treated with water (20 mL), adjusted to pH 6 with HCl solution (1.0 M) and extracted with diethyl ether (3×20 mL). The aqueous portion was purified on reverse-phase (C18) HPLC to give 41.3 mg of the titled compound 42.

Example 28

3'-Azido-3'-deoxythymidine 5'-α-P-borano-β,γ-diluoromethylene-γ-O-(4-nitrophenyl)triphosphate (43)

The triethylammonium salts of 3'-deoxy-3'-azidothymidine 5'-α-P-borano-β,γ-(difluoromethylene)triphosphate (25 μmol) was coevaporated with anhydrous DMF (3×2 mL). For the third coevaporation, approximately half the volume of DMF was removed and methanol (30 μL) was added, followed by N,N'-dicyclohexylcarbodiimide (20 mg). After stirring at room temperature under an argon atmosphere for 3 h, the mixture was evaporated in vacuo and the above procedure was repeated once. After removing solvents in vacuo, the residue was resuspended in anhydrous DMF (2 mL), treated with anhydrous triethylamine (0.09 mL) followed by addition of p-nitrophenol (90 mg). After stirring at room temperature under an argon atmosphere for 4 h reaction mixture was treated with water (10 mL), adjusted to pH 6 with HCl solution (0.1 M) and extracted with diethyl ether (3×10 mL). The aqueous portion was purified on reverse-phase (C18) HPLC to give 1.8 mg of the titled compound 43.

Example 29

3'-Azido-3'-deoxythymidine 5'-γ-P-chloro-P-methyl-α,β-(difluoromethylene)triphosphate (44)

To a stirred solution of 1,2,4-1H-triazole (18.3 mg, 0.265 mmol.) in anhydrous acetonitrile (0.5 mL) was added triethylamine (26.8 mg, 37 μL, 0.265 mmol.). The solution was cooled to 0° C., and a solution of methylphosphonic dichloride (17.6 mg, 0.133 mmol) in acetonitrile (0.5 mL) was added dropwise. The reaction mixture was kept with stirring for 40 minutes at room temperature and then centrifuged. The supernatant was added to a solution of the tributylammonium salt of 3'-azido-3'-deoxythymidine 5'-(difluoromethylene)diphosphonate (89.8 mg, 0.0884 mmol) in DMF (1 mL). The reaction mixture was kept with stirring for 1.5 hours and then quenched by adding waster (2 mL). Purification by HPLC gave 13.1 mg of the titled compound 44.

Example 30

3'-Azido-3'-deoxythymidine 5'-γ-P-phenyl-α,β-(difluoromethylene)triphosphate (45)

To a stirred solution of 1,2,4-1H-triazole (18.4 mg, 0.267 mmol.) in anhydrous acetonitrile (0.5 mL) was added triethylamine (27 mg, 37.2 μL, 0.267 mmol.). The solution was cooled to 0° C., and phenylphosphonic dichloride (26 mg, 0.134 mmol.) in acetonitrile (0.5 mL) was added dropwise. The reaction mixture was kept with stirring for 40 minutes at 4° C. temperature and then centrifuged. The supernatant was added to a solution of the tributylammonium salt of 3'-azido-3'-deoxythymidine 5'-(difluoromethylene)diphosphonate (90.3 mg, 0.089 mmol) in DMF (1 mL). Similar work-up and purification as described for compound 44 gave 12.8 mg of the titled compound 45.

Example 31

3'-Azido-3',5'-dideoxythymidine 5'-(β,γ-difluoromethylene)triphosphate (55)

Step A. The Preparation of 1-(3-O-acetyl-2,5-dideoxy-5-iodo-β-D-threo-pentofuranosyl)thymine (49)

To a stirred solution of 1-(2,5-dideoxy-5-iodo-β-D-threo-pentofuranosyl)thymine (for preparation see ref. J. Org. Chem. 1964, 29, 2076) (5.1 g, 14.5 mmol) in anhydrous pyridine (50 mL) at 0° C. under argon was added acetic anhydride (7.0 ml, 75.4 mmol). The reaction mixture was stirred at room temperature for 17 h. The reaction mixture was cooled with ice bath and quenched by slow addition of water (15 mL). The reaction mixture was stirred for 30 min and concentrated to dryness, and co-evaporated with anhydrous toluene three times. The residue was re-dissolved in dichloromethane and chromatographed on silica gel with 1-3% methanol in ethyl acetate gave 4.4 g of 1-(3-O-acetyl-2,5-dideoxy-5-iodo-β-D-threo-pentofuranosyl)thymine (49).

Step B. The Preparation of 1-[3-O-acetyl-2,5-dideoxy-5-(di-O-ethylphosphono)-β-D-threo-pentofuranosyl]thymine (50)

To a stirred solution of 1-(3-O-acetyl-2,5-dideoxy-5-iodo-β-D-threo-pentofuranosyl) thymine (49) (4.4 g, 12.5 mmol) in freshly distilled triethyl phosphite (50 mL) under argon was heated at 180° C. for 30 h. The reaction mixture was concentrated to dryness and the residue left was re-dissolved in dichloromethane and chromatographed on silica gel with 2-4% ethanol in dichloromethane gave 2.4 g of 1-[3-O-acetyl-2,5-dideoxy-5-(di-O-ethylphosphono)-1-D-threo-pentofuranosyl]thymine (50) as light yellow foam.

Step C. The Preparation of 1-[2,5-dideoxy-5-(di-O-ethylphosphono)-3-O-mesyl-β-D-threo-pentofuranosyl]thymine (51)

To a stirred solution of 1-[3-O-acetyl-2,5-dideoxy-5-(di-O-ethylphosphono)-β-D-threo-pentofuranosyl]thymine (50) (1.08 g, 2.68 mmol) in anhydrous ethanol (75 mL) under argon at 0° C. was added sodium ethoxide, (0.28 g, 4.03 mmol) in one portion. Reaction mixture was stirred for 2 h at 0° C. Added more sodium ethoxide, (47.5 mg, 0.67 mmol) after it was stirred for 1 h at 0° C. The resulted yellow color solution was neutralized with DOWEX 50WX8-100 ion exchange resin. The resin was removed by filtration and washed with anhydrous ethanol (60 mL). The filtrate was evaporated to dryness and the residue left was re-dissolved in dichloromethane and chromatographed on silica gel with 3-3.5% ethanol in dichloromethane gave 0.62 g of as 1-[2,5-dideoxy-5-(di-O-ethylphosphono)-β-D-threo-pentofuranosyl]thymine.

To a stirred solution of 1-[2,5-dideoxy-5-(di-O-ethylphosphono)-β-D-threo-pentofuranosyl]thymine (1.3 g, 3.69 mmol) in anhydrous pyridine (30 mL) under argon at 0° C. was added 4-(dimethylamino)pyridine (0.225 g, 1.85 mmol) followed by methanesulfonyl chloride (0.42 mL, 5.54 mmol). The reaction mixture was stirred for 13 h at room temperature. The reaction mixture was cooled with ice bath and quenched by slow addition of water (15 mL). The reaction mixture was stirred for 20 min and concentrated to dryness, and co-evaporated with anhydrous toluene three times. The residue was re-dissolved in dichloromethane and chromatographed on silica gel with 2-3% ethanol in dichloromethane gave 1.5 g of 1-[2,5-dideoxy-5-(di-O-ethylphosphono)-3-O-mesyl-β-D-threo-pentofuranosyl]thymine (51)

Step D. The Preparation of 1-[3-azido-3,5-dideoxy-5-(di-O-ethylphosphono)-β-D-erythro-pentofuranosyl]thymine (52)

To a stirred solution of 1-[2,5-dideoxy-5-(di-O-ethylphosphono)-3-O-mesyl-β-D-threo-pentofuranosyl]thymine (51) (1.5 g, 3.41 mmol) in anhydrous DMF (25 mL) under argon at room temperature was added $NaN_3$ (0.44 g, 6.8 mmol). Reaction mixture was stirred for 14 h at 80° C. The reaction mixture was filtered and solvents were evaporated. The residue was re-dissolved in dichloromethane and chromatographed on silica gel with 3-3.5% ethanol in dichloromethane gave 0.73 g of 1-[3,5-dideoxy-3-azido-5-(di-O-ethylphosphono)-β-D-erythro-pentofuranosyl]thymine (52).

Step E. The Preparation of 3'-azido-3',5'-dideoxythymidine-5'-phosphonic acid (53)

To a stirred solution of 1-[3,5-dideoxy-3-azido-5-(di-O-ethylphosphono)-β-D-erythro-pentofuranosyl]thymine (52) (0.2 g, 0.52 mmol) in anhydrous $CH_3CN$ (5.5 mL) under argon was added $Me_3SiBr$ (0.5 mL, 3.65 mmol). The reaction mixture was stirred for 4 h at 40° C. The reaction mixture was concentrated to dryness, and co-evaporated with anhydrous acetonitrile twice. The residue was and then coevaporated with MeOH three times. The residue left was re-dissolved in water (3.0 mL) and washed with ether two times and combined aqueous solution was freeze-dried to afford 0.181 g of 3'-azido-3',5'-dideoxythymidine-5'-phosphonic acid (53) which was used without further purification.

Step F. The Preparation of 3'-azido-3',5'-dideoxythymidine 5'-(β,γ-difluoromethylene)-triphosphate (55)

To a solution of 3'-azido-3',5'-dideoxythymidine-5'-phosphonic acid (53) (0.181 g, 0.55 mmol) in water (2.5 mL) was added 1.34 ml of 1M triethylammoniumbicarbonate buffer and resulted solution was lyophilized to afford 263 mg of triethylammonium salt of compound 53. The triethylammonium salt of compound 53 (69.3 mg, 0.13 mmol) was dissolved in HMPA (2.5 mL) and 1,1'-carbonyldiimidazole (107 mg, 0.65 mmol) was added at room temperature and stirred for 2 h. Methanol (35 μl) was added and stirring was continued for 45 min. difluoromethylenediphosphonic acid bis(tri-n-butylammonium) salt (397 mg, 0.68 mmol) dissolved in HMPA (2.5 mL) was added and the resulting solution was stirred at room temperature for 4 h. The reaction mixture was cooled in ice-bath and ice/water (4 mL) was added. Purification by HPLC gave 16.6 mg of the titled compound 55.

Example 32

3'-Azido-3',5'-dideoxythymidine 5'-(β,γ-dichloromethylene)triphosphate (56)

The triethylammonium salt of compound 53 (59.1 mg, 0.11 mmol) was dissolved in HMPA (2 mL) and 1,1'-carbonyldiimidazole (93 mg, 0.57 mmol) was added at room temperature and stirred for 2 h. Methanol (30 μl) was added and stirring was continued for 55 min. Dichloromethylenediphosphonic acid tri-n-butylammonium salt (288 mg, 0.51 mmol) dissolved in HMPA (2.5 mL) was added with syringe to the solution of activated AZT monophosphate, and the combined solution was stirred at room temperature for 6 h. The reaction mixture was cooled in ice-bath and ice/water (5 mL) was added. Purification by HPLC gave 8.3 mg of the titled compound 56.

Example 33

3'-Azido-3',5'-dideoxythymidine 5'-β,γ-imidotriphosphate (57)

The triethylammonium salt of compound 53 (50.0 mg, 0.09 mmol) was dissolved in HMPA (2 mL) and 1,1'-carbonyldiimidazole (106 mg, 0.66 mmol) was added at room temperature and stirred for 2 h. Methanol (35 μL) was added and stirring was continued for 45 min. The tri-n-butylammonium salt of imidodiphosphate (427 mg, 0.46 mmol) dissolved in HMPA (2 mL) was added with syringe to the solution of activated AZT monophosphate, and the combined solution was stirred at room temperature for 4 h. The reaction mixture was cooled in ice-bath and water (5 mL) was added. Purification by HPLC gave 30.6 mg of the titled compound 57.

Example 34

1-[6,6-Difluoro-6-(β,γ-difloromethylene)triphosphono-2,3,5,6-tetradeoxy-α/β-D-allofuranosyl]thymine (62)

Step A. 6-Diethylphosphono-6,6-difluoro-1-O-methyl-2,3,5,6-tetradeoxy-D-allofuranose (59)

To an ice-cold mixture of trifluoromethanesulfonic anhydride (2.43 mL, 14.4 mmol) in anhydrous $CH_2Cl_2$ (100 mL) under argon was added 2,6-di-tert-butyl-4-methylpyridine (2.96 g, 14.4 mmol). The solution was cooled to −20° C. and 2,3-dideoxy-1-O-methyl-D-ribofuranose (for preparation, see for example: *Can. J. Chem.* 1969, 47: 4413) (1.9 g, 14.4 mmol) in anhydrous $CH_2Cl_2$ (75 mL) was added dropwise. The reaction mixture was stirred at −15 to −5° C. for 45 min, then poured into ice-cold aq. $NaHCO_3$ (1%, 1 L) and vigorously shaken. The layers were separated and aqueous layer extracted with $CH_2Cl_2$ (2×75 mL). Combined extract was dried ($Na_2SO_4$), concentrated and rapidly purified on silica gel column using hexanes and hexanes/$Et_2O$ as eluents. Product-containing fractions were concentrated and used immediately for the next step.

To a solution of diisopropylamine (6.05 mL, 43.2 mmol) and HMPA (7.52 mL, 43.2 mmol) in anhydrous THF (40 mL) at −78° C. under argon was added n-butyllithium (27 mL of 1.6 M in hexanes, 43.2 mmol). The mixture was stirred at 0° C. for 1 h and then cooled to −78° C. To this solution were added dropwise via transfer needles a cold (−78° C.) solution of diethyl (difluoromethyl)phosphonate (6.8 mL, 43.2 mmol) in THF (40 mL) and after 30 min a cold (−78° C.) solution of the triflate prepared above in THF (90 mL). The reaction mixture was stirred at −78° C. for 2 h and then poured into cold (−10° C.) sat. aq. $NH_4Cl$ (300 mL), diluted with $Et_2O$ (300 mL) and layers separated. Aqueous layer was further extracted with EtOAc (2×150 mL), combined extract dried ($Na_2SO_4$) and concentrated. Silica gel chromatography with hexanes and hexanes/EtOAc (10:1) as eluents yielded the titled compound 59 as colorless oil (1.33 g; 31% for 2 steps).

Step B. 1-[6-Diethylphosphono-6,6-difluoro-2,3,5,6-tetradeoxy-α/β-D-allofuranosyl]thymine (60)

The product 59 from Step A (1.33 g, 4.4 mmol) in acetonitrile (30 mL) was added to the solution of bis (trimethylsilyl)thymine in acetonitrile. The latter was prepared by refluxing thymine (1.11 g, 8.8 mmol) with bis (trimethyl)silyl acetamide (2.3 mL; 8.8 mmol) in acetonitrile (30 mL) for 15 min. The combined mixture was cooled to 0° C. when $SnCl_4$ (4.4 mL of 1M in $CH_2Cl_2$, 4.4 mmol) was added dropwise, and then heated at 75° C. for 45 min. After cooling in an ice-bath it was poured into ice-cold aq. $NaHCO_3$ (5%, 200 mL) and extracted with $CH_2Cl_2$ (200+2×100 mL). The combined extract was dried ($Na_2SO_4$), concentrated and purified on silica gel with $CH_2Cl_2$/MeOH (50:1) as eluent to yield the titled compound 60 as mixture of diastereomers (0.8 g, 46%; α/β 3/2).

Step C. 1-[6,6-Difluoro-6-phosphono-2,3,5,6-tetradeoxy-α/β-D-allofuranosyl]thymine (61)

To an ice-cold mixture of the product 60 from Step B (550 mg, 1.6 mmol) in anhydrous acetonitrile (15 mL) under argon was added dropwise TMSBr (4.2 mL, 20 equiv). The resulting mixture was stirred at room temperature for 1 day. The volatiles were removed in vacuo under anhydrous conditions and the residue coevaporated several times with toluene and finally partitioned between $Et_2O$ (20 mL) and water (100 mL). Aqueous layer was neutralized with TEAB buffer (1M, pH 8.5) washed with $Et_2O$ (2×20 mL) and evaporated to give the triethylammonium salt of 61 as a white solid (630 mg; 76%).

Step D. 1-[6,6-Difluoro-6-(β,γ-difluoromethylenetriphosphono)-2,3,5,6-tetradeoxy-α/β-D-allofuranosyl]thymine (62)

To a solution of product 61 from Step C (94 mg, 0.17 mmol) in HMPA (2.5 mL) under argon was added 1,1'-carbonyldiimidazole (110 mg, 4 equiv). The reaction mixture was stirred at room temperature for 4 h, when bis[tri (n-butyl)ammonium](difluoromethylene)bisphosphonate (400 mg, 4 equiv) in HMPA (2 mL) was added. After 8 h (24% of the target triphosphate in mixture with 56% of the imidazolyl phosphonate intermediate as judged by LCMS)

the reaction was quenched by pouring into 1M TEAB buffer (10 mL, pH 8.5) and the mixture purified by HPLC to yield 9.2 mg of the titled compound 62.

Example 35

1-[6,6-Difluoro-6-(β,γ-imidotriphosphono)-2,3,5,6-tetradeoxy-α/β-D-allofuranosyl]-thymine (63)

To a solution of product 61 from Step C (94 mg, 0.17 mmol) in HMPA (2.5 mL) under argon was added 1,1'-carbonyldiimidazole (CDI) (138 mg, 5 equiv). After 4 h stirring at room temperature the excess of CDI was quenched with MeOH (27.5 μL, 4 equiv). Tetrakis[tri(n-butyl)ammonium)]imidodiphosphate (270 mg, 1.2 equiv) in HMPA (2 mL) was added and stirring at room temperature continued. After 18 h (25% of the target triphosphate in mixture with 41% of the imidazolyl phosphonate intermediate as judged by LCMS) the reaction mixture was quenched by pouring into 1M TEAB buffer (10 mL, pH 8.5) and the mixture purified by HPLC to yield 7.3 mg of the titled compound 63.

Example 36

1-[6,6-Difluoro-2,3,5,6-tetradeoxy-6-triphosphono-α/β-D-allofuranosyl]thymine (64)

Following the procedure for the compound 63, starting from 102 mg (0.19 mmol) of the product 61 from Step C, using tri(n-butyl)ammonium pyrophosphate (246 mg), after 18 h (25% of the target triphosphate in mixture with 41% of the imidazolyl phosphonate intermediate as judged by LCMS) 12 mg of the titled compound 64 was isolated.

Example 37

3'-Azido-3'-deoxythymidine 5'-α,β,β-O-(tripivaloyloxymethyl-β,γ-imidodiphosphate (68)

Step A. The Preparation of Iodomethyl Pivalate

Chloromethyl pivalate (26 g, 25 mL, 0.17 mol) was added dropwise to a stirred solution of sodium iodide (52 g, 0.34 mol) in anhydrous acetone (170 mL) under argon. After stirring at room temperature for 24 h, 170 mL hexanes was added. The precipitated salt was filtered and washed with hexanes. The filtrate was concentrated and dissolved in 170 mL of hexanes, washed with 5% $NaHSO_3$, then water 2 times, and dried over $MgSO_4$. The solvent was evaporated under reduced pressure to yield a yellow liquid. After a flash chromatography on silica with hexanes fractions containing iodomethyl pivalate was combined and washed with $NaHSO_3$ to eliminate $I_2$. After drying and evaporation 34 g of iodomethyl pivalate were obtained as a slightly-yellow syrup.

Step B. 3'-Azido-3'-deoxythymidine 5'-α,β,β-O-(tripivaloyloxymethyl-β,γ-imidodiphosphate (68)

A mixture of 3'-azido-3'-deoxythymidine 5'-imidodiphosphate (5'-O-imidodiphosphate of AZT was prepared according to the literature. (Ma et al., *J. Med. Chem.* 1992, 35, 1938-1941) (H+ form, 57 mg, 0.13 mmol) and tributylstannyl methoxide (125 mg, 0.39 mmol) in methanol (3 mL) was stirred at 25° C. for 30 min. Methanol was removed by evaporation. To thoroughly remove methanol, the residue was coevaporated with acetonitrile three times. To the residue in acetonitrile (3 mL) were added tetrabutylammonium bromide (126 mg, 0.39 mmol) and iodomethyl pivalate (472 mg, 1.95 mmol). The mixture was refluxed for 1 h and then cooled to 25° C. The mixture was concentrated to a small volume (0.3 mL) under reduced pressure and then applied on a silica gel column. The column was eluted with chloroform and methanol to give 57 mg of the titled compound 68.

Example 38

3'-Azido-3'-deoxythymidine 5'-α-P-borano-γ-O-(pivaloyloxymethyl-β,γ-(difluoromethylene)triphosphate (69)

To a stirred solution of the triethylammonium salt of 3'-azido-3'-deoxythymidine 5'-α-P-borano-β,γ-(difluoromethylene)triphosphate (27) (186 mg, 0.196 mmol) in methanol (5 mL) under argon was added tributylstannyl methoxide (63 mg, 57 μL, 0.196 mmol). The reaction mixture was stirred for 45 minutes, concentrated, coevaporated with acetonitrile (3×3 mL), and dried under high vacuum. The residue was dissolved in acetonitrile (5 mL) under argon, to this solution were added tetrabutylammonium bromide (63.3 mg, 0.196 mmol) and POM (30.7 μL, 0.196 mmol). The reaction mixture was kept with stirring at room temperature for 5.5 hours, quenched by adding water (1 mL), and purified on reverse-phase HPLC to give 4.4 mg of the titled compound 69.

Example 39

3'-Azido-3'-deoxythymidine 5'-α-P-borano-γ-O—(S-pivaloyl-2-thioethyl)-β,γ-(difluoromethylene)triphosphate (70)

Step A. The Preparation of S-pivaloyl-2-thioethanol

To a solution of 2-mercaptoethanol (15.6 g, 14 mL, 0.2 mol) in anhydrous THF (200 mL), NaH (8 g, 0.2 mol, 60% dispersion in mineral oil) was added slowly with magnetic stirring at room temperature. After cooling to 0° C., pivaloyl chloride (28.9 g, 14.8 mL, 0.24 mol) was added dropwise. After 5 hours, it was quenched by adding a mixture of $CH_2Cl_2$ and water (500 mL, V/V 8:1). The organic layer was separated and washed by water (100 mL) 2 times, and dried by $MgSO_4$. It was filtrated and the solvent was evaporated under reduced pressure. Purification by a flash chromatography on silica with hexanes/EtOAc (10:1) gave 13.7 g of S-pivaloyl-2-thioethanol as a light-yellow liquid.

Step B. The Preparation of S-pivaloyl-2-thioethyl 4-nitrobenzenesulfonate

4-Dimethylaminopyridine (937 mg, 7.67 mmol) was added to a stirred solution of S-pivaloyl-2-thioethanol (1.038 g, 6.40 mmol) in $CH_2Cl_2$ (20 mL). Then a solution of 4-nitrobenzenesolfonyl chloride (1.70 g, 7.67 mmol) in $CH_2Cl_2$ (20 mL) was added dropwise at 0° C. under argon. After stirring for 2 hours, the reaction was quenched by adding ice-cooled mixture of water (50 mL) and $CH_2Cl_2$ (100 mL), and stirred for 5 minutes. It was diluted with $CH_2Cl_2$ (200 mL), and separated. The organic phase was washed by ice-cooled saturated $NaHSO_4$, brine and dried by $MgSO_4$. Chromatography on silica with 5% EtOAc in hexanes gave 1.09 g of S-pivaloyl-2-thioethyl 4-nitrobenzenesulfonate.

Step C. 3'-Azido-3'-deoxythymidine 5'-α-P-borano-γ-O—(S-pivaloyl-2-thioethyl)-β,γ-(difluoromethylene)triphosphate (70)

To a solution of the bis(tetrabutylammonium salt of 3'-azido-3'-deoxythymidine 5'-α-P-borano-β,γ-(difluoromethylene)triphosphate (27) (0.107 mmol) in anhydrous acetonitrile was added S-pivaloyl-2-thioethyl 4-nitrobenzenesulfonate (74 mg, 0.214 mmol) in acetonitrile (0.5 mL). The resulting solution stood at room temperature overnight, cooled with ice, quenched with water (3 mL). Most of the acetonitrile was evaporated and the remaining aqueous solution was subject to a reverse-phase HPLC purification to give 5.9 mg of the titled compound 70.

Example 40

3'-Azido-3'-deoxythymidine 5'-β,β-O-di(S-pivaloyl-2-thioethyl)imidodiphosphate (71) and 3'-azido-3'-deoxythymidine 5'-α,β,β-O-tri(S-pivaloyl-2-thioethyl)imidodiphosphate (72)

To a solution of 3'-azido-3'-deoxythymidine 5'-O-imidodiphosphate (128 mg, 0.3 mmol) in anhydrous pyridine (8 mL) at room temperature under argon were added S-pivaloyl-2-thioethanol (487 mg, 10 eqs.) and 1-(mesitylene-2-sulfonyl)-3-nitro-1,2,4-triazole (444 mg, 5 eqs.). After stirring at room temperature for 2 days, the reaction mixture was neutralized with 1 M aqueous triethylammonium hydrogencarbonate buffer (pH=7.5) and extracted with chloroform. The organic layer was dried over sodium sulfate, filtered, and evaporated to dryness under reduced pressure. The crude product was purified by reversed-phase HPLC (C18) to give 1.7 mg of 71 and 3.48 mg of 72.

Example 41

2'-Deoxy-2',2'-difluorocytidine 5'-β-O—(S-pivaloyl-2-thioethyl)-α,β-methylene-diphosphonate; 2'-deoxy-2',2'-difluorocytidine 5'-di-α, β-O-(S-pivaloyl-2-thioethyl)-α,β-methylenediphosphonate; and 2'-deoxy-2',2'-difluorocytidine 5'-tri-O-(S-pivaloyl-2-thioethyl)-α,β-methylenediphosphonate (75, 76 and 77)

2'-Deoxy-2',2'-difluorocytidine (0.5 g, 1.9 mmol) was dissolved in anhydrous trimethyl phosphate (10 mL) and stirred with molecular sieves under an argon atmosphere for 16 h. The mixture was cooled to −20° C. under an argon atmosphere and treated with methylenebis(phosphonic dichloride) (522 mg, 2.09 mmol). After stirring for 1 h a white precipitate developed. Tributylamine (6.8 mL, 29 mmol) was added followed by S-pivalyl-2-thioethanol (3.1 g, 19 mmol) and the mixture was stirred at room temperature for 1 h. The mixture was quenched using ice-cold TEAB solution (1.0 M, 15 mL) and stirred for 30 minutes. Purification by reverse-phase (C18) HPLC gave 36.5 mg of (75), 42.6 g of (76); and 64.3 g of (77).

Example 42

3'-Azido-3'-deoxythymidine 5'-α-P-borano-γ-O-[(2,3-O-dipalmitoylglyceroxy)carbonyl-3-propionoxy-]2-ethyl-β,γ-(difluoromethylene)triphosphate (79)

Step A. [(2,3-O-Dipalmitoylglyeroxy)carbonyl-3-propionoxy]-2-ethanol

A solution of 1,2-dipalmitoyl-rac-glyceral (844 mg, 1.49 mmol) in methylene chloride (15 mL) was added to a solution of succinyl chloride (1.38 g, 982 μL, 8.91 mmol) in methylene chloride (4 mL) at 0° C. under argon. Pyridine (940 mg, 961 ul, 11.9 mmol) was then added in five-portions with a 10 min interval between two additions. The reaction continued for 1.5 hours, then cooled down to −78° C. Ethylene glycol (1.85 g, 1.66 mL, 29.7 mmol) was added, and the resulting mixture warmed up to room temperature and stirred for 2.5 hours. A mixture of EtOAc (200 mL) and water (200 mL) was added, the aqueous layer was extracted with EtOAc. The combined organic phase was washed by water, saturated $NaHCO_3$ (2 times), dried over $MgSO_4$. Chromatography on Silica gel with 10-20% EtOAc in hexane yielded 0.68 g of [(2,3-O-Dipalmitoylglyeroxy)carbonyl-3-propionoxy]-2-ethanol.

Step B. [(2,3-O-Dipalmitoylglyeroxy)carbonyl-3-propionoxy]-2-ethyl p-nitrobenzenesulfonate (78)

In a stirred solution of [(2,3-O-dipalmitoylglyeroxy)carbonyl-3-propionoxy]-2-ethanol (516 mg, 0.685 mmol) in methylene chloride (5 mL) under argon, a 4-dimethylaminopyridine (210 mg, 1.72 mmol) was added. The solution was cooled to 0° C. and a solution of 4-nitrobenzenesulfonyl chloride (310 mg, 1.40 mmol) in methylene chloride (7 mL) was added. The reaction mixture was stirred at 0° C. for 0.5 h, warmed to room temperature. After stirring for another hour, the reaction was quenched by adding ice-cooled water (6 mL) and stirred for 5 minutes. The mixture was diluted with methylene chloride (200 mL), and washed with saturated ice-cooled $NaHCO_3$ 2 times (200 mL each), then ice-cooled water 2 times (200 mL each), dried over $MgSO_4$, purified by chromatography on silica with 20% EtOAc in hexanes to give 0.544 g of the titled product (78).

Step C. 3'-Azido-3'-deoxythymidine 5'-α-P-borano-γ-O-[(2,3-O-dipalmitoylglyceroxy)carbonyl-3-propionoxy]-2-ethyl)-β,γ-(difluoromethylene)triphosphate (79)

To a stirred solution of [(2,3-O-dipalmitoylglyeroxy)carbonyl-3-propionoxy]-2-ethyl p-nitrobenzenesulfonate (78) (480 mg, 0.527 mmol) in $CHCl_3$ (2.5 mL) under argon, tris(tetra-n-butylammonium) salt of 3'-azido-3'-deoxythymidine 5'-α-P-borano-β,γ-(difluoromethylene)triphosphate (27) (163 mg, 0.13 mmol) in $CHCl_3$ (1.8 mL) was added, followed by addition of tributylamine (185 mg, 62 μL, 0.259 mmol). The reaction mixture was stirred for 24 hours, extracted with 50% water/acetonitrile (3×6 mL), filtered, and concentrated to remove partial acetonitrile. The aqueous mixture was purified by reverse-phase HPLC to give 20 mg of the titled compound 79.

Example 43

(E)-2'-Deoxy-2'-(fluoromethylene)cytidine 5'-ethylenediphosphonate (80)

Ethylenediphosphonic acid (100 mg, 0.53 mmol) was treated with oxalyl chloride (2 mL, as solvent) and anhydrous DMF (0.1 mL, cat.). After heating at reflux for 10 minutes under an argon atmosphere a solution was obtained and after a further 3 h the reaction mixture was cooled to room temperature and concentrated in vacuo. The residue was coevaporated with anhydrous acetonitrile (3×10 mL). The residue was dissolved in anhydrous trimethyl phosphate (2 mL), cooled to −15° C. under an argon and (E)-2'-deoxy-2'-(fluoromethylene)cytidine (64 mg, 0.25 mmol) was added. After stirring for 2 h the reaction mixture was quenched with ice-cold TEAB solution (1.0 M, 5 mL) and stirred for 30 minutes. Purification by HPLC gave 2.9 mg of the titled compound 80.

Example 44

2'-Deoxy-2',2'-difluorocytidine 5'-ethylenediphosphonate (81)

Ethylenediphosphonic acid (173 mg, 0.91 mmol) was treated with oxalyl chloride (2 mL, as solvent) and anhydrous DMF (0.1 ml, cat.). After heating at reflux for 10 minutes under argon, a solution was obtained and after a further 3 h the reaction mixture was cooled to room temperature and evacuated in vacuo. The residue was co-evaporated with anhydrous acetonitrile (3×10 ml). The residue was dissolved in anhydrous trimethyl phosphate (2 mL), cooled to −15° C. and 2'deoxy-2',2'-difluorocytidine (93 mg, 0.46 mmol) was added under argon. After stirring for 2 h the reaction mixture was quenched with ice-cold TEAB solution (1.0 M, 5 mL) and stirred for 30 minutes. Purification by HPLC gave 7.8 mg of the titled compound 81.

B. Biological Assays

Example 45

HIV Reverse Transcriptase Inhibition Assays

The assays employed to measure inhibition of HIV Reverse Transcriptase (HIV RT) catalyzed/RNA-directed DNA polymerization are described below. The effectiveness of the compounds of the present invention as inhibitors of HIV RT-catalyzed DNA polymerization was measured in the following assays.

A. Assay for Inhibition of HIV Reverse Transcriptase-Catalyzed DNA Polymerization (Homopolymer RNA Template).

This assay was used to measure the ability of the nucleotide mimics of the present invention to inhibit the enzymatic synthesis of complementary strand DNA from a DNA-primed template of homopolymeric RNA. This assay is a modification of a published procedure (Seville, et al., “Fluorometric Assay for DNA Polymerases and Reverse Transcriptase”, *BioTechniques* 1996, 21, 664-72).

Procedure:

Assay Buffer Conditions: (50 µL-total/reaction)

50 mM Tris-HCl, pH 8.1

6.5 mM $MgCl_2$ 100 mM NaCl 10 mM DTT

5 µM dTTP (thymidine triphosphate)

1 ug/mL Primed-poly(A) RNA 2 nM purified HIV Reverse Transcriptase (Type B, 66 kDa subunit)

The compounds were tested at various concentrations up to 500 µM final concentration. DNA polymerase activity was measured in a reaction buffer containing primed-RNA template and dTTP diluted to appropriate concentrations in assay buffer. Nucleotide mimics of the present invention were diluted in buffer and pipetted into the wells of a 96-well plate. The reaction was initiated by addition of enzyme and allowed to proceed at 37° C. for 10 minutes. The reaction was quenched by addition of 5 µL 0.2 M EDTA, pH 8.0.

Blank reactions were prepared in parallel with the test reactions in which either enzyme or dTTP was omitted from the reactions, substituted by an appropriate volume of enzyme diluent or assay buffer, respectively.

200 µL of diluted PicoGreen dsDNA Quantitation Reagent (Molecular Probes, Inc, Eugene, Oreg.) was added to each well of a 96-well plate and incubated at room temperature for 5 minutes. Plate wells were read on a microplate fluorometer (Molecular Devices Corp., Sunnyvale, Calif.). The wells were excited at 480 nm and the fluorescence emission intensity (RFU) was measured at 520 nm. The percentage of inhibition was calculated according to the following equation:

$$\% \text{ Inhibition}=[1-(RFU \text{ in test reaction}-RFU \text{ in blank})/(RFU \text{ in control reaction}-RFU \text{ in blank})]\times 100.$$

Inhibition constants ($K_i$) were determined for representative compounds that exhibited ≧50% inhibition at 10 µM when tested in the HIV RT homopolymer polymerization assay. Each inhibitor was titrated over an appropriate range of concentrations, and inhibition constants were determined using the following equations:

Michaelis-Menten Equation:

$$v=V_m[S]/(K_m+[S])$$

Competitive Inhibition Equation:

$$v=V_m[S]/(K_m(1+[I]/K_i)+[S])$$

where v=initial velocity, $V_m$=maximal velocity, S=substrate, I=inhibitor, $K_m$=Michaelis constant, and $K_i$=inhibition constant.

Representative compounds of the present invention tested in the HIV RT-catalyzed DNA polymerization assay exhibited inhibition constants less than 100 µM.

B. Assay for Inhibition of HIV Reverse Transcriptase-Catalyzed DNA Polymerization (Heteropolymer RNA Template).

Certain compounds of the present invention were also tested to determine their ability to inhibit HIV RT-catalyzed DNA polymerization on a heteropolymeric primed-RNA template in the presence of all four natural deoxynucleotide triphosphate (dNTP) substrates. This assay is a modification of a published procedure (Parker et al., “Mechanism of Inhibition of Human Immunodeficiency Virus Type 1 Reverse Transcriptase and Human DNA Polymerases α, α, and γ by the 5'-Triphosphates of Carbovir,3'-Azido-3'-deoxythymidine,2'-3'-Dideoxyguanosine, and 3'-Deoxythymidine”, *J. Biol. Chem.* 1991, 266 (3), 1754-62).

Procedure:

Assay Buffer Conditions: (120 µL-total/reaction)

50 mM Tris-HCl, pH 8.1

6.5 mM $MgCl_2$ 100 mM NaCl 10 mM DTT

50 µM dNTPs (dATP, TTP, dGTP, dCTP)

5 ug/mL Primed-Ribosomal RNA (*E. Coli*)

10 Units HIV Reverse Transcriptase (purified, Type B, 66 kDa subunit)

HIV RT DNA polymerase activity was measured in a reaction buffer containing primed-ribosomal RNA template and dNTPs diluted to appropriate concentrations in assay buffer and pipetted into 1.5 mL microcentrifuge tubes. Nucleotide mimics of the present invention were diluted in buffer and tested at various concentrations up to 5 µM final concentration. The reaction was initiated by addition of enzyme and allowed to proceed at 42° C. for 60 to 90 minutes. The reaction was quenched by addition of 12 µL 0.2 M EDTA, pH 8.0.

Blank reactions were prepared in parallel with the test reactions in which either enzyme or dNTP was omitted from the reactions, substituted by an appropriate volume of enzyme diluent or assay buffer, respectively.

50 µL each of reaction was transferred to the well of a 96-well plate (in duplicate). 200 µL of diluted PicoGreen dsDNA Quantitation Reagent was added to each well of a 96-well plate and incubated at room temperature for 5 minutes. Plate wells were read on a microplate fluorometer. The wells were excited at 480 nm and the fluorescence emission intensity (RFU) was measured at 520 nm. The percentage of inhibition and inhibition constants ($K_i$) were determined for representative compounds as described above.

TABLE 1

Inhibition of HIV Reverse Transcriptase by Nucleotide Mimics

| Compound | $K_i$ (µM) |
|---|---|
| 8 | 4.4 |
| 17-isomer 1 | 0.009 |
| 17-isomer 2 | 0.048 |
| 27-isomer 1 | 0.008 |
| 27-isomer 2 | 0.061 |
| 26-isomer 1 | 0.093 |
| 26-isomer 2 | 0.074 |
| 23 | 0.105 |
| 25 | 0.027 |
| 29 | 0.090 |
| 42 | 0.113 |
| 40 | 0.069 |

Example 46

Ribonucleotide Reductase Inhibition Assay

The assays employed to measure inhibition of Ribonucleotide Reductase (RNR) activity are described below. The effectiveness of the compounds of the present invention as inhibitors of RNR enzyme was determined using the following assays.

A. Assay for Inhibition of RNR Activity

This assay was used to measure the ability of the nucleotide mimics of the present invention to inhibit the enzymatic reaction catalyzed by RNR enzyme. In the reduction of cytidine 5'-diphosphate (CDP) to 2'-deoxycytidine 5'-diphosphate (dCDP), stoichiometric amounts of oxidized thioredoxin are formed. This protein is reduced by NADPH in a reaction catalyzed by thioredoxin reductase. By coupling the two reactions, RNR activity was measured by spectrophotometric determination of NADPH oxidation at 340 nm using a UV/VIS spectrophotometer. This assay is a modification of a published procedure (van der Donk et al., "Inactivation of Ribonucleotide Reductase by (E)-2'-Fluoromethylene-2'-deoxycytidine 5'-Diphosphate: A Paradigm for Nucleotide Mechanism-Based Inhibitors," *Biochemistry* 1996, 35, 8381-91).

Procedure:

Irreversible Inactivaton Conditions: (50 µL-total/reaction)

50 mM HEPES, pH 7.6

15 mM $MgSO_4$ 1 mM EDTA 1.6 mM ATP 0.5 mM NADPH

20 µM Thioredoxin 0.5 µM Thioredoxin Reductase

1 µM RNR R1

2 µM RNR R2

Assay Conditions: (200 µL-total/reaction)

50 mM HEPES, pH 7.6

15 mM $MgSO_4$ 1 mM EDTA 1.6 mM ATP 0.5 mM NADPH

20 µM Thioredoxin 0.5 µM Thioredoxin Reductase 1 mM CDP

The compounds were tested at various concentrations up to 500 µM final concentration. The nucleotide mimics of the present invention were added to irreversible inactivation mixtures at the desired concentrations. An identical control was run in which the inhibitor was replaced with $H_2O$. After a 3-minute incubation, 20 µL was removed from the inactivation mixtures and assayed for activity.

The standard RNR assay is performed in a 96-well plate (Corning). Aliquots from the inactivation mixtures were added to an appropriate volume of assay buffer pipetted into the plate wells. The reactions were initiated by the addition of the substrate CDP. The reactions were allowed to proceed for 5 minutes at 25° C. The oxidation of NADPH was monitored at 340 nm on a microplate spectrophotometer (Molecular Devices Corp, Sunnyvale, Calif.). Initial velocity data (mA $min^-$) was collected and fit to the equations below.

Blank reactions were prepared in parallel with the test reactions in which substrate was omitted from the reactions, substituted by an appropriate volume of $H_2O$.

The percentage of inhibition was calculated according to the following equation:

$$\%\ \text{Inhibition}=[1-(\text{mA min}^{-1}\ \text{in test reaction}-\text{mA min}^{-1}\ \text{in blank})/(\text{mA min}^{-1}\ \text{in control reaction}-\text{mA min}^{-1}\ \text{in blank})]\times 100.$$

The inhibitor concentration values giving 50% inhibition ($IC_{50}$) were determined for representative compounds that exhibited ≧50% inhibition at 250 µM when tested in the RNR inhibition assay. Each inhibitor was titrated over an appropriate range of concentrations, and $IC_{50}$ values were determined using the equation:

$IC_{50}$ Equation:

$$v_i/v_o=1/(1+[I]/IC_{50})$$

where $v_i$=initial velocity in the presence of inhibitor at concentration I, $v_o$=initial velocity in the absence of inhibitor, and $IC_{50}$=inhibitor concentration giving 50% inhibition.

Representative compounds of the present invention tested in the RNR inhibition assay exhibited inhibition constants less than 250 µM.

TABLE 2

Inhibition of Ribonucleotide Reductase by Nucleotide Mimics

| | $IC_{50}$ (µM) |
|---|---|
| 3 | 8.9 |
| 6 | 12.6 |

Example 47

Tubulin Assays

The assays employed to measure the polymerization and stability of tubulin microtubule protein are described below. The effectiveness of the compounds of the present invention as modulators of tubulin microtubule protein dynamics was measured in the following assays.

A. Assay for Inhibition of Microtubule Polymerization.

This assay was used to measure the ability of the nucleotide mimics of the present invention to inhibit the polymerization of tubulin subunits and subsequent assembly of microtubule protein. This assay is a modification of a published procedure (Xu et al., "Interaction of Tubulin with Guanosine 5'-O-(1-Thiotriphosphate) Diastereoisomers: Specificity of the α-Phosphate Binding Region", *Biochemistry* 1994, 33, 11884-90).

Procedure:

Assay Buffer Conditions: (100 μL-total/reaction)

80 mM PIPES, pH 6.9

2 mM $MgCl_2$ 0.5 mM EGTA

10% glycerol

50 μM GTP (guanosine 5'-triphosphate)

300 ug purified bovine brain tubulin (Cytoskeleton, Denver, Colo.)

The compounds were tested at various concentrations up to 500 μM final concentration. Polymerization assays were performed in 96-well microplates (Costar), in assay buffer containing GTP and tubulin. The nucleotide mimics of the present invention were diluted in buffer and pipetted into the plate wells. Samples were kept on ice until the reactions were initiated by moving the plates into a 37° C. incubator. The polymerization reaction was allowed to proceed at 37° C. for 30 minutes, monitored at 340 nm using a microplate spectrophotometer with a temperature-controlled incubator (Molecular Devices, Sunnyvale, Calif.). Initial velocity data (mA $min^{-1}$) was collected and fit to the equations below.

Blank reactions were prepared in parallel with the test reactions in which either tubulin or GTP was omitted from the reactions, substituted by an appropriate volume of assay buffer.

The percentage of inhibition was calculated according to the following equation:

$$\% \text{ Inhibition}=[1-(\text{mA min}^{-1} \text{ in test reaction}-\text{mA min}^{-1} \text{ in blank})/(\text{mA min}^{-1} \text{ in control reaction}-\text{mA min}^{-1} \text{ in blank})]\times 100.$$

Inhibition constants ($K_i$) were determined for representative compounds that exhibited >50% inhibition at 250 μM when tested in the tubulin polymerization assay. Each inhibitor was titrated over an appropriate range of concentrations, and inhibition constants were determined using the following equations:

Michaelis-Menten Equation:

$$v=V_m[S]/(K_m+[S])$$

Competitive inhibition equation:

$$v=V_m[S]/(K_m(1+[I]/K_i)+[S])$$

where v=initial velocity, $V_m$=maximal velocity, S=substrate, I=inhibitor, $K_m$=Michaelis constant, and $K_i$=inhibition constant.

Representative compounds of the present invention tested in the tubulin polymerization assay exhibited inhibition constants less than 200 μM.

B. Assay for Disruption of Microtubule Dynamics

This assay was used to measure the ability of the nucleoside derivatives of the present invention to interfere with normal microtubule protein dynamics, including the rate of polymerization, the rate of depolymerization, and stabilization of microtubule protein. This assay is a modification of the method described in O. Monasterio and S. N. Timasheff, "Inhibition of Tubulin Self-Assembly and Tubulin-Colchicine GTPase Activity by Guanosine 5'-(γ-Fluorotriphosphate)", *Biochemistry* 26: 6091-99 (1987).

Procedure:

Assay Buffer Conditions: (100 μL-total/reaction)

80 mM PIPES, pH 6.9

2 mM $MgCl_2$ 0.5 mM EGTA

10% glycerol 300 ug purified bovine brain tubulin (Cytoskeleton, Denver, Colo.)

The compounds were tested at various concentrations up to 500 μM final concentration. Polymerization assays were performed in 96-well microplates (Costar), in assay buffer containing tubulin. The nucleotide mimics of the present invention were diluted in buffer and pipetted into the plate wells. Samples were kept on ice until the reactions were initiated by moving the plates into a 37° C. incubator. The polymerization reaction was allowed to proceed at 37° C. for 30 minutes, monitored at 340 nm using a microplate spectrophotometer with a temperature-controlled incubator (Molecular Devices, Sunnyvale, Calif.).

Depolymerization of the microtubule protein was achieved by transferring the plates from 37° C. to a 0-4° C. incubator for 20 minutes. Plates were then returned to the 37° C. incubator, and the second cycle of polymerization was allowed to proceed for 15 minutes. Initial velocity data (mA $min^{-1}$) for both polymerization cycles was collected and fit to the equations described above.

Blank reactions were prepared in parallel with the test reactions in which tubulin was omitted from the reactions, substituted by an appropriate volume of assay buffer.

The degree of disruption of microtubule dynamics was determined relative to control reactions containing 50 μM GTP and tubulin.

C. Phosphate Assay for Tubulin-GTP Hydrolysis

This assay was used to measure the ability of the nucleotide mimics of the present invention to inhibit hydrolysis of GTP by tubulin. The enzymatic conversion of GTP to GDP+ inorganic phosphate ($P_i$) is monitored in a coupled-spectrophotometric assay using the EnzChek Phosphate Assay Kit (Molecular Probes, Inc, Eugene, Oreg.). This assay is a modification of a published procedure (Vandecandelaere et al., "Phosphate Release during Microtubule Assembly: What Stabilizes Growing Microtubules?", *Biochemistry* 1999, 38, 8179-88).

Procedure:

Assay Buffer Conditions: (100 μL-total/reaction)

80 mM PIPES, pH 6.9

2 mM $MgCl_2$ 0.5 mM EGTA

10% glycerol

50 μM GTP 50 ug purified bovine brain tubulin

The compounds were tested at various concentrations up to 500 μM final concentration. GTP hydrolysis assays were performed in 96-well microplates (Costar), in assay buffer containing tubulin, GTP, MESG, and PNP. The nucleotide mimics of the present invention were diluted in buffer and pipetted into the plate wells. Samples were kept on ice until the reactions were initiated by moving the plates into a 37° C. incubator. The hydrolysis reaction was initiated by addition of GTP, and allowed to proceed at 37° C. for 10 minutes. The reaction was monitored at 360 nm using a microplate spectrophotometer with a temperature-controlled incubator (Molecular Devices, Sunnyvale, Calif.). Initial velocity data (mA $min^{-1}$) was collected and fit to the equations described above.

Blank reactions were prepared in parallel with the test reactions in which GTP was omitted from the reactions, substituted by an appropriate volume of assay buffer.

TABLE 3

Inhibition of Tubulin Polymerization by Nucleotide Mimics

| Compound Name | $K_i$ (μM) |
|---|---|
| Guanosine 5'-diphosphate | 15.3 |
| Guanosine 5'-imidodiphosphate | 5.7 |
| 2'-Deoxy-2'-fluoromethylenecytidine 5'-diphosphate | 19.4 |
| 2'-Deoxy-2'-fluoromethylenecytidine 5'-ethylenediphosphonate (81) | 15.7 |

Example 48

Mammalian Cell Growth Inhibition Assay

The assays employed for determining the cytotoxicity of the nucleotide mimics of the present invention to mammalian cells are described below.

Mammalian Cells and Growth Conditions

Human CCRF-CEM cells were obtained from American Tissue Culture Collection (ATCC) and grown according to ATCC specifications. Briefly, CCRF-CEM, a lymphoblastoid cell line, was grown and maintained as a suspension culture in RPMI 1640 medium containing 2 mm L-glutamine, 10 mM HEPES, 1 mM sodium pyruvate, 4.5 g/L glucose, 1.5 g/L sodium bicarbonate and supplemented with 10% (v/v) dialyzed and heat-inactivated fetal bovine serum. CEM cells were grown at 37° C. in a 95% humidified environment and 5% $CO_2$ atmosphere.

Cytotoxicity Assays: MTT Assay.

The cytotoxicity of the nucleotide mimics of the present invention to mammalian cells was determined by measuring cell survival using 3-(4,5-dimethylthiazol-2-yl)-2,5-diphenyltetrazolium bromide (MTT) (Slater T. F. et al., *Biochim. Biophys. Acta* 1963, 77, 383; Mossman T. *J. Immunol. Methods* 1983, 65, 55; M. E. et al., 1999, *J. Biol. Chem.* 28505-13). MTT is a water soluble tetrazolium salt that is converted to an insoluble purple formazan by active mitochondrial dehydrogenases of living cells. Dead cells do not cause this change. Conversion of MTT into the insoluble formazan by non-treated control or treated cells was monitored at 540 nm.

CCRF-CEM cells ($3\times10^4$) were plated in 96-well plates in RPMI media. The next day, cells were incubated with different concentrations (0-200 μM) of the nucleotide mimics of the present invention for 72 hr. Following treatment, MTT (2 mg/ml in PBS) dye was added to each well so that the final concentration was 0.5 mg/ml and then incubated for 4 hr at 37° C. Media and MTT dye were removed without disturbing the cells and 100% DMSO was added to dissolve the precipitate. After a 10 minute incubation at room temperature, the optical density values were measured at 540 nm, using the Spectra Max Plus plate reader. Survival was expressed as the percentage of viable cells in treated samples relative to non-treated control cells.

TABLE 4

Antiproliferative effect of nucleotide mimics and their prodrugs

| Compound | Cytotoxicity IC50 (μM) |
|---|---|
| Gemcitabine | 0.035 |
| 5 | 4.8 |
| 75 | 0.025 |
| 76 | 0.025 |
| 77 | 0.1 |

Example 49

Antimicrobial Assays

To examine the antimicrobial potential of the nucleotide mimics of the present invention an assay was employed that allowed the screening of a large number of compounds simultaneously. The type of bacteria chosen to screen the compounds are organisms associated with human disease and represent major groups of bacteria based on their structure and metabolism.

Lawn Screening Assay:

Bacterial cultures of *Escherichia coli* and *Staphylococcus aureus* were incubated overnight at 37° C. in a shaker incubator. A lawn of each overnight bacterial culture was made by plating 200 μl of bacteria on agar plates containing Nutrient Broth. Immediately after plating, sterile blank paper discs were put on top of the lawn and a compound was applied to each blank paper disc. Plates were then incubated overnight and examined for the inhibition of bacterial growth the following day.

Minimal Inhibitory Concentration Determination

Bacterial cells ($2\times10^4$) growing in exponential phase were plated in 96-well plates and treated with different concentrations (0-200 μg/ml) of the nucleotide mimics of the present invention. The plates were incubated overnight at 37° C. and then examined spectrophotometrically at 600 nm to determine the minimum concentration of each compound that inhibited replication of bacteria as determined by no increase in absorbance at 600 nm.

TABLE 5

Antibacterial activity of nucleotide mimics and their prodrugs

| Compound | *E. coli* MIC μg/ml (uM) | *S. aureus* MIC μg/ml (μM) |
|---|---|---|
| AZT | 2 (7.5 uM) | NA* |
| 27-isomer 1 | 60 (111) | NA |
| 27-isomer 2 | 50 (93) | NA |
| 26-isomer 1 | 12 (21) | NA |
| 26-isomer 2 | 10 (17.5) | NA |
| 25-isomer 1 | 25-50 (48-96) | NA |
| 25-isomer 4 | 25-50 (48-96) | NA |
| 23 | 50-100 (99-198) | NA |
| 69 | 0.75 (1) | NA |
| 70 | 6 (8.8) | NA |
| 71 | 20 (28) | NA |
| 41 | 25-50 (33-66) | 5-10 (6.5-13) |
| 40 | 25-50 (40-80) | NA |
| 5 | NA | >200 (>475) |
| 75 | NA | 15 (26) |
| 76 | NA | 25 (35) |

NA*. Not active

Example 50

Serum Stability Assessment

The stability of nucleotide mimics was assessed in fetal calf serum generally following the procedure outlined by Arzumanov et al., (*J. Biol. Chem.* 1996, 271(40), 24389-24394). Fetal calf serum purchased from HyClone Corporation was mixed 1:1 with each compound containing Tris-HCl buffer and $MgCl_2$. Typically the total volume used for the experiment was 500 μl. The final concentrations of the reaction components were as follows:

50 mM Tris-HCl, pH 7.4

0.1 mM $MgCl_2$

500 μM nucleotide mimic

50% (v/v) fetal calf serum

The reaction mixtures were made up and incubated at 37° C. At appropriate times aliquots of 25 μl were removed and added to 65 μl ice-cold methanol. These solutions were incubated for at least one hour at −20° C. and typically overnight. After incubation samples were centrifuged for at least 20 minutes at high speed in a microcentrifuge. The supernatant was transferred to a clean tube and the extract was dried under vacuum in a LabConco Centrivap Concentrator. The dried extracts were resuspended in $dH_2O$ and filtered to remove particulate before analysis on reverse phase HPLC.

The reverse phase HPLC columns used for the analysis were either a Phenomenex C18 Aqua column (2×100 mm) or the Phenomenex C18 Aqua column (3×150 mm) used with the appropriate guard column. The HPLC was run at 0.2 ml/min (for the 2×100 mm column) or at 0.5 ml/min (for the 3×150 mm column) with the following buffer system: 5 mM tetrabutylammonium acetate, 50 mM ammonium phosphate, and an acetonitrile gradient running from 5% up to as high as 60%. The amount of remaining parent compound at each time point was used to determine the half-life of the compound. Time points were only taken through 48 hours so that if greater than 50% of a compound was still intact after 48 hours incubation the half-life was expressed as >48 hours. Unmodified nucleoside triphosphates were used as positive controls. Under these conditions unmodified nucleoside triphosphates had half-lives of approximately two hours.

TABLE 6

Serum Half-Lives of NTPs and AZT Triphosphate Mimics

| Compound | Half-Life (hours) |
|---|---|
| Adenosine Triphosphate | 2 |
| Thymidine Triphosphate | 2 |
| AZT Triphosphate | 2 |
| AZT α-P-Boranotriphosphate (Rp) | 6 |
| AZT α-P-Boranotriphosphate (Sp) | 6 |
| 27-Isomer 1 | >48 |
| 27-Isomer 2 | >48 |
| 26-Isomer 1 | 45 |
| 26-Isomer 2 | 48 |
| 23 | 36 |

TABLE 7

Serum Half-Lives of AZT Triphosphate Mimic Prodrugs

| Compound Name | Half-Life (hours) |
|---|---|
| Adenosine Triphosphate | 1.5 |
| 27-Isomer | >48 |
| 69 | >48 |
| 70 | >48 |
| 42 | >48 |

TABLE 8

Serum Half-Lives of Gemcitibine Diphosphate Mimics and Their Prodrugs

| Compound | Half-Life (hours) |
|---|---|
| Adenosine Triphosphate | 2.5 |
| 6 | 15 |
| 75 | >48 |
| 76 | >48 |
| 5 | >48 |

Example 51

Stability Assessment Using Cell Extracts

The stability of compounds in cell extracts was examined as follows:

Cell lysis buffer was added to cell pellets and the cells frozen and thawed 3× using dry ice. The lysis buffer (LB) was composed of the following: 50 mM Tris-HCl, pH 7.4 (100 μl/ml 10× stock), 20% glycerol (200 μl/ml), and 0.5% Triton X-100 (5 μl/ml). 100 μl of LB was added to each microfuge tube containing $10^7$ frozen CEM cells. After the cells were lysed the extracts were centrifuged at high speed in a microcentrifuge for 5 minutes and the clarified cell extract transferred to a new tube. The cell stability reaction mixtures contained concentrations of buffer, magnesium, nucleotide, and cell extract as shown below:

50 mM Tris-HCl, pH 7.4

0.1 mM $MgCl_2$

500 μM nucleotide mimic (or control nucleotide)

50% cell extract (v/v)

The reaction mixtures were incubated at 37° C. At each time point, including at time zero, 12.5 μl aliquots were added to 40 μl ice-cold methanol. Typically, time points were taken after 30 and 60 minutes, and 2, 3, 8, 24, and 48 hours. The samples were incubated in methanol for at least 60 minutes and typically overnight at −20° C. prior to further processing. The cell extracts were centrifuged at high speed in refrigerated microcentrifuge for 20 minutes and the supernatant transferred to a new tube. The extract was then dried under vacuum in a LabConco Centrivap Concentrator. The samples were then resuspended in 40 or 50 μl $dH_2O$, filtered to remove any particulate, and analyzed by reverse phase HPLC.

The reverse phase HPLC columns used for the analysis were either a Phenomenex C18 Aqua column (2×100 mm) or the Phenomenex C18 Aqua column (3×150 mm) used with the appropriate guard column. The HPLC flow rate was either 0.2 ml/min (for the 2×100 mm column) or 0.5 ml/min (for the 3×150 mm column) with the following buffer system: 5 mM tetrabutylammonium acetate, 50 mM ammonium phosphate, and an acetonitrile gradient running from 5% up to as high as 60%. The amount of remaining parent compound at each time point was used to determine the half-life of the compound. Time points were only taken through 48 hours so that if greater than 50% of a compound was still intact after 48 hours incubation the half-life was expressed as >48 hours. Unmodified nucleoside triphosphates were used as positive controls. Under these conditions unmodified nucleoside triphosphates had half-lives of approximately ten minutes.

TABLE 9

Cell extract Half-Lives of AZT Triphosphate Mimics

| Compound Number | Half-Life (hours) |
|---|---|
| Adenosine Triphosphate | .25 |
| 27-Isomer 1 | >48 |
| 27-Isomer 2 | >48 |
| 26-Isomer 1 | >48 |
| 26-Isomer 2 | >48 |

TABLE 10

Cell Extract Half-Lives of AZT 5'-α-P-borano-β,γ-(difluoromethylene)triphosphate Prodrugs

| Compound Number | Half-Life (hours) |
|---|---|
| Adenosine Triphosphate | .25 |
| 69 | 8 |
| 70 | 15 |
| 41 | >48 |

TABLE 11

Cell Extract Half-Lives of Gemcitibine 5'-Methylendiphosphonate and its Prodrugs

| Compound Number | Half-Life (hours) |
|---|---|
| Adenosine Triphosphate | .25 |
| 75 | 19 |
| 76 | 37 |
| 5 | >48 |

Example 52

Cell Uptake Procedure

CEM cells were resuspended in RPMI at $1\times10^7$ cells/mL. The appropriate amount of each compound was added to well and then 0.5 ml of the cells was aliquoted into the appropriate number of wells of a 24-well plate and incubated the cells at 37° C. Cells were harvested after 24 hours of incubation. To harvest cells they were transferred to a microfuge tube and spun for one minute at high speed. The samples were washed in PBS containing 1 mg/ml BSA and re-centrifuged. The PBS was then aspirated and 200 μL of ice-cold 60% methanol was added to extract the nucleotides. The extracts were incubated overnight at −20° C. The next day the samples were spun at high speed in a microfuge for 20 minutes and the supernatant transferred to clean tubes and dried in the speed vac. After drying the samples were resuspended in 50 μl, filtered, and the samples then directly injected onto the HPLC. The nucleotides were analyzed using reverse phase HPLC with ion-pairing agents for separation of the nucleotides. The procedure was adapted from the following paper: Furman, et al., *Proc. Natl. Acad. Sci. USA* 1986, 83, 8333-8337.

TABLE 12

Results from 24 hour incubation with AZTTP prodrug mimics

| Compound Number | Incubation Concentration (μM) | Intracellular levels of 27 (pmol/$10^6$ cells) |
|---|---|---|
| 27-isomer 1 | 25 | BLD |
| | 50 | 5.6 |
| | 100 | 10.6 |
| 69 | 25 | 33.1 |
| | 50 | 51.1 |
| | 100 | 70.8 |
| 70 | 25 | 10.5 |
| | 50 | 15.6 |
| | 100 | 19.7 |

The limit of detection was estimated to be 5 pmol/$10^6$ cells.

Example 51

In Vitro Anti-HIV Activity Assay

The procedure was adapted from the following paper: Structure-Activity and Cross-Resistance Evaluations of a Series of Human Immunodeficiency Virus Type 1-Specific Compounds Related to Oxathiin Carboxanilide. Buckheit, Jr. et al., *Antimicrobial Agents and Chemotherapy,* 1995, 39,?2718-2727.

CEM-SS/MTS Anti-HIV Assays

The antiviral efficacy of test compounds were evaluated in CEM-SS cell cultures infected with the lymphocyte-tropic virus strain HIV-$1_{RF}$ at an MOI of approximately 0.01. At assay termination, assay plates were stained with the soluble tetrazolium-based dye MTS (CellTiter 96 Reagent, Promega) to determine cell viability and quantify compound toxicity. MTS is metabolized by the mitochondria enzymes of metabolically active cells to yield a soluble formazan product, allowing the rapid quantitative analysis of cell viability and compound cytotoxicity.

Efficacy Evaluation in CEM-SS Cells Anti-HIV-1 Cytoprotection Assay

Cell Preparation—CEM-SS cells were passaged in T-75 flasks prior to use in the antiviral assay. On the day preceding the assay, the cells were split 1:2 to assure they were in an exponential growth phase at the time of infection. Total cell and viability quantification was performed using a hemacytometer and trypan blue exclusion. Cell viability was greater than 95% for the cells to be utilized in the assay. The cells were resuspended at $5\times10^4$ cells/ml in tissue culture medium and added to the drug-containing microtiter plates in a volume of 50 μl.

Virus Preparation—The virus used for these tests was the lymphocytropic virus strain HIV-$1_{RF}$. This virus was obtained from the NIH AIDS Research and Reference Reagent Program and was grown in CEM-SS cells for the production of stock virus pools. For each assay, a pre-titered aliquot of virus was removed from the freezer (−80° C.) and allowed to thaw slowly to room temperature in a biological safety cabinet. The virus was resuspended and diluted into tissue culture medium such that the amount of virus added to each well in a volume of 50 μl was the amount determined to give between 85 to 95% cell killing at 6 days post-infection. $TCID_{50}$ calculations by endpoint titration in CEM-SS cells indicated that the multiplicity of infection of these assays was approximately 0.01.

MTS Staining for Cell Viability

At assay termination, the assay plates were stained with the soluble tetrazolium-based dye MTS (CellTiter Reagent Promega) to determine cell viability and quantify compound toxicity. MTS is metabolized by the mitochondrial enzymes of metabolically active cells to yield a soluble formazan product, allowing the rapid quantitative analysis of cell viability and compound cytotoxicity. The MTS is a stable solution that does not require preparation before use. At termination of the assay, 20 μL of MTS reagent was added per well. The microtiter plates were then incubated 4-6 hrs at 37° C. for the HIV cytoprotection assay; the incubation intervals were chosen based on empirically determined times for optimal dye reduction. Adhesive plate sealers were used in place of the lids, the sealed plate was inverted several times to mix the soluble formazan product and the plate was read spectrophotometrically at 490 nm with a Molecular Devices Vmax plate reader.

TABLE 13

Anti-HIV Screening

| Compound Number | CEM-SS $IC_{50}$ | CEM-SS $TC_{50}$ | Therapeutic Index |
|---|---|---|---|
| 27-isomer 1 | 1.64 μM | >200.0 μM | 122.32 |
| 69 | 1.13 μM | 45.9 μM | 40.75 |
| 70 | 0.95 μM | >200.0 μM | >210.89 |
| 41 | 1.41 μM | 12.0 μM | 8.53 |
| 43 | 6.43 μM | 125.0 μM | 19.43 |
| 40 | 4.00 μM | >200.0 μM | >50.03 |
| 42 | 2.54 μM | 32.1 μM | 12.64 |

What is claimed is:

1. A compound of Formula (I) which may be a D- or L-nucleotide:

(I)

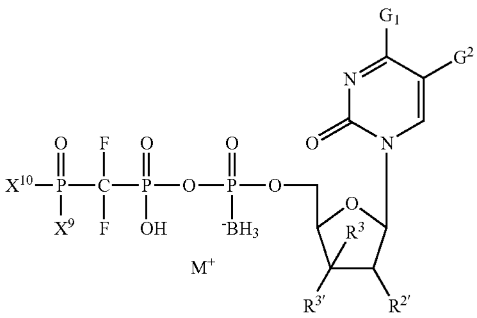

wherein $R^{2'}$ is H, F, OH, or OMe;

wherein $R^3$ is methyl, ethyl, vinyl, ethynyl, or hydroxymethyl;

wherein $R^{3'}$ is H, F, OH, or $N_3$;

wherein $G^1$ is OH or $NH_2$;

wherein $G^2$ is H or Me; and wherein $X^9$ and $X^{10}$ are selected independently from the group consisting of OH, alkoxy, aryloxy, acylthioethoxy, acyloxymethoxy, 1,2-O-diacylglyceryloxy, 1,2-O-dialkylglyceryloxy, and 1-O-alkyl-2-O-acylglyceryloxy.

2. A compound of Formula (II) which may be a D- or L-nucleotide:

(II)

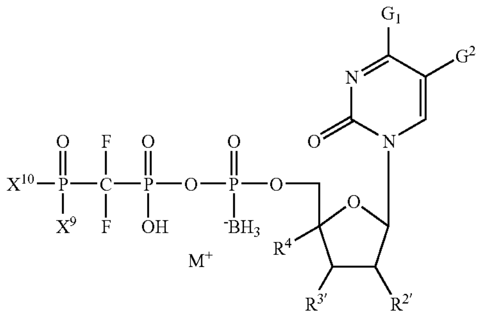

wherein $R^{2'}$ is H, F, OH, or OMe;

wherein $R^{3'}$ is H, F, OH, or $N_3$;

wherein $R^4$ is methyl, ethyl, vinyl, ethynyl, or hydroxymethyl;

wherein $G^1$ is OH or $NH_2$;

wherein $G^2$ is H or Me; and wherein $X^9$ and $X^{10}$ are selected independently from the group consisting of OH, alkoxy, aryloxy acylthioethoxy, acyloxymethoxy, 1,2-O-diacylglyceryloxy, 1,2-O-dialkylglyceryloxy, and 1-O-alkyl-2-O-acylglyceryloxy.

3. A compound of Formula (III) which may be a D- or L-nucleotide:

(III)

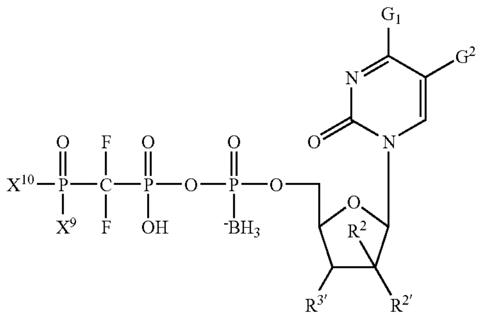

wherein $R^2$ is methyl, ethyl, vinyl, ethynyl, or hydroxymethyl;

wherein $R^{2'}$ is H, F, OH, or OMe, alkyl, methoxyethoxy, or $NH_2$;

wherein $R^{3'}$ is H, F, OH, or $N_3$;

wherein $G^1$ is OH or $NH_2$;

wherein $G^2$ is H or Me; and wherein $X^9$ and $X^{10}$ are selected independently from the group consisting of OH, alkoxy, and aryloxy.

4. A compound of Formula (IV) which may be a D- or L-nucleotide:

(IV)

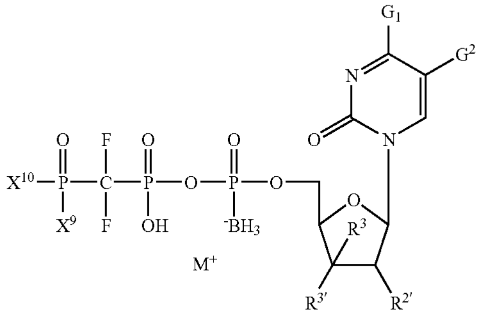

wherein $R^{2'}$ is H, F, OH, or OMe;

wherein $R^3$ is methyl, ethyl, vinyl, ethynyl, or hydroxymethyl;

wherein $R^{3'}$ is H, F, OH, or $N_3$;

wherein $G^1$ is OH or $NH_2$;

wherein $G^2$ is H or Me; and wherein $X^9$ and $X^{10}$ are selected independently from the group consisting of OH, alkoxy, and aryloxy.

5. A compound of Formula (V) which may be a D- or L-nucleotide:

(V)

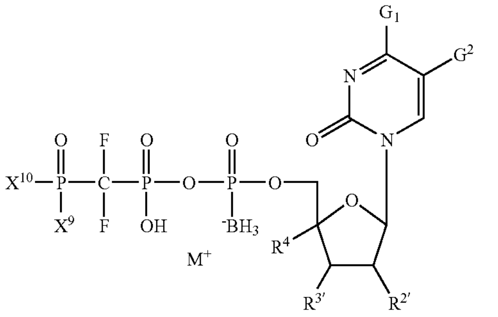

wherein $R^{2'}$ is H, F, OH, or OMe;

wherein $R^{3'}$ is H, F, OH, or $N_3$;

wherein $R^4$ is methyl, ethyl, vinyl, ethynyl, or hydroxymethyl;

wherein $G^1$ is OH or $NH_2$;

wherein $G^2$ is H or Me; and wherein $X^9$ and $X^{10}$ are selected independently from the group consisting of OH, alkoxy, and aryloxy.

6. A pharmaceutical composition comprising a therapeutically effective amount of the compound according to claim 1, a pharmaceutically acceptable salt thereof, optionally in combination with one or more other active ingredients and/or with a pharmaceutically acceptable carrier.

7. A pharmaceutical composition comprising a therapeutically effective amount of the compound according to claim 2, a pharmaceutically acceptable salt thereof, optionally in combination with one or more other active ingredients and/or with a pharmaceutically acceptable carrier.

8. A pharmaceutical composition comprising a therapeutically effective amount of the compound according to claim 3, a pharmaceutically acceptable salt thereof, optionally in combination with one or more other active ingredients and/or with a pharmaceutically acceptable carrier.

9. A pharmaceutical composition comprising a therapeutically effective amount of the compound according to claim 4, a pharmaceutically acceptable salt thereof, optionally in combination with one or more other active ingredients and/or with a pharmaceutically acceptable carrier.

10. A pharmaceutical composition comprising a therapeutically effective amount of the compound according to claim 5, a pharmaceutically acceptable salt thereof, optionally in combination with one or more other active ingredients and/or with a pharmaceutically acceptable carrier.

* * * * *

UNITED STATES PATENT AND TRADEMARK OFFICE

CERTIFICATE OF CORRECTION

PATENT NO. : 7,285,658 B2
APPLICATION NO. : 10/376654
DATED : October 23, 2007
INVENTOR(S) : Phillip D. Cook et al.

It is certified that error appears in the above-identified patent and that said Letters Patent is hereby corrected as shown below:

Col. 3, line 66, after "α,β:β,γ-bismethylenetriphosphates," insert --β,γ-dihalomethylenetriphosphates,--

Col. 3, line 66 to Col. 4, line 1, "α,β-dihalomethylenetriphosphates, α,β-dihalomethylenetriphosphates," should read --α,β-dihalomethylenetriphosphates,--

Col. 4, line 7, "considerable" should read --considerably--; line 17, "*J. boil*" should read --*J. biol*--; line 20 "γ-P-aryltriphosphate" should read --α-P-aryltriphosphate--

Col. 24, after line 24 and before line 25 insert a new line:
--2',3'-dideoxyuridine,--

Col. 25, line 8, "2'-P-fluorothymidine" should read --2'β-fluorothymidine--

Col. 37, line 56, delete "2',3-dideoxy-5-fluorouridine"

Col. 64, line 61, "tri(tetrabutylamomonium)" should read --tri(tetrabutylammonium)--

Col. 65, line 46, Col. 66, line 6, Col. 67, line 2, and Col. 68, lines 8 and 58 the word "bis(tributylammunium)", each occurrence, should read --bis(tributylammonium)--

Col. 74, line 66, "waster" should read --water--

Col. 75, lines 53-55, "of 1-[3-*O*-acetyl-2,5-dideoxy-5-(di-*O*-ethylphosphono)-1-D-threo-pentofuranosyl]thymine (50)" should read -of 1-[3-*O*-acetyl-2,5-dideoxy-5-(di-*O*-ethylphosphono)-β-D-pentofuranosyl]thymine (50)--

Col. 84, line 43, "Polymerases α, α," should read --Polymerases α, β,--

Col. 86, line 25, "(mA min $^{-}$)" should read --(mA min $^{-1}$)--

Col. 89 lines 46-47, "M.E. et al. 1999, *J. Biol Chem.* 28505-13" should read --Marie E. Ariza, et al. 1999, *J. Biol Chem.* 274, 28505-13--

UNITED STATES PATENT AND TRADEMARK OFFICE

CERTIFICATE OF CORRECTION

PATENT NO. : 7,285,658 B2
APPLICATION NO. : 10/376654
DATED : October 23, 2007
INVENTOR(S) : Phillip D. Cook et al.

It is certified that error appears in the above-identified patent and that said Letters Patent is hereby corrected as shown below:

Col. 94, line 25, “Example 51” should read --Example 53--; line 34, “39,?2718-2727” should read --39, 2718-2727--

Signed and Sealed this

Twenty-third Day of September, 2008

JON W. DUDAS
*Director of the United States Patent and Trademark Office*